（12) United States Patent
Ise et al.

(10) Patent No.: US 11,170,624 B2
(45) Date of Patent: Nov. 9, 2021

(54) SYSTEM AND PROCESS FOR DISPLAYING MEDICAL ALARMS

(71) Applicant: Drägerwerk AG & Co. KGaA, Lübeck (DE)

(72) Inventors: Edgar Ise, Lübeck (DE); Michael Gömann, Lübeck (DE); Sebastian Fischer, Lübeck (DE); Andi Kern, Lübeck (DE); Konradin Windhorst, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 17/109,984

(22) Filed: Dec. 2, 2020

(65) Prior Publication Data

US 2021/0174662 A1    Jun. 10, 2021

(30) Foreign Application Priority Data

Dec. 4, 2019   (DE) .................... 10 2019 008 406.3

(51) Int. Cl.
| | |
|---|---|
| *A61B 1/00* | (2006.01) |
| *G08B 21/02* | (2006.01) |
| *A61B 5/00* | (2006.01) |
| *G08B 5/22* | (2006.01) |
| *G08B 21/18* | (2006.01) |

(52) U.S. Cl.
CPC ................ *G08B 21/02* (2013.01); *A61B 5/72* (2013.01); *A61B 5/742* (2013.01); *A61B 5/746* (2013.01); *A61B 5/7475* (2013.01); *G08B 5/22* (2013.01); *G08B 21/182* (2013.01)

(58) Field of Classification Search
CPC .................................. A61B 1/00; G16H 10/00
See application file for complete search history.

(56) References Cited

U.S. PATENT DOCUMENTS

| | | |
|---|---|---|
| 2003/0200117 A1 | 10/2003 | Manetta et al. |
| 2005/0038332 A1 | 2/2005 | Saidara et al. |
| 2006/0081244 A1 | 4/2006 | Bouillon et al. |

(Continued)

FOREIGN PATENT DOCUMENTS

| | | |
|---|---|---|
| DE | 102016001139 A1 | 1/2017 |
| EP | 2777488 A1 | 9/2014 |

(Continued)

*Primary Examiner* — Shirley Lu
(74) *Attorney, Agent, or Firm* — McGlew and Tuttle, P.C.

(57) ABSTRACT

A system includes a medical device, a patient sensor, an output unit and a signal processing unit that receives measured values from patient sensors and generates signals by analyzing received measured values. The signal processing unit decides whether an alarm criterion, relating to the generated signal, is met and detects an alarm and an alarm time and actuates the output unit. The actuated output unit displays an overall alarm sequence (16) in an overall time period (T) and an alarm reference sequence in a reference section (26) time window (T1) temporally positioned relative to the overall alarm sequence. At least one of a signal curve display (10) and an alarm reference sequence (18) are displayed as a portion of the overall time period. Time scales for the signal curve display and the alarm reference sequence are finer than time scales for the overall alarm sequence and the alarm reference section.

13 Claims, 47 Drawing Sheets

(56) References Cited

U.S. PATENT DOCUMENTS

| | | |
|---|---|---|
| 2008/0078390 A1 | 4/2008 | Milne et al. |
| 2008/0214904 A1 | 9/2008 | Saeed et al. |
| 2009/0005655 A1 | 1/2009 | Frank et al. |
| 2011/0138311 A1 | 6/2011 | Palmer |
| 2013/0032149 A1 | 2/2013 | Robinson et al. |
| 2013/0044111 A1 | 2/2013 | Vangilder et al. |
| 2013/0246089 A1 | 9/2013 | Gross et al. |
| 2014/0275819 A1 | 9/2014 | Kassem et al. |
| 2015/0234993 A1 | 8/2015 | Detzler et al. |
| 2017/0039319 A1 | 2/2017 | Manetta et al. |
| 2018/0174683 A1 | 6/2018 | Franz et al. |
| 2018/0277243 A1* | 9/2018 | Qing .................. A61B 5/339 |
| 2018/0300919 A1 | 10/2018 | Muhsin et al. |
| 2020/0097715 A1 | 3/2020 | Henninger |

FOREIGN PATENT DOCUMENTS

| | | |
|---|---|---|
| WO | 2013158625 A1 | 10/2013 |
| WO | 2016188741 A1 | 12/2016 |

* cited by examiner

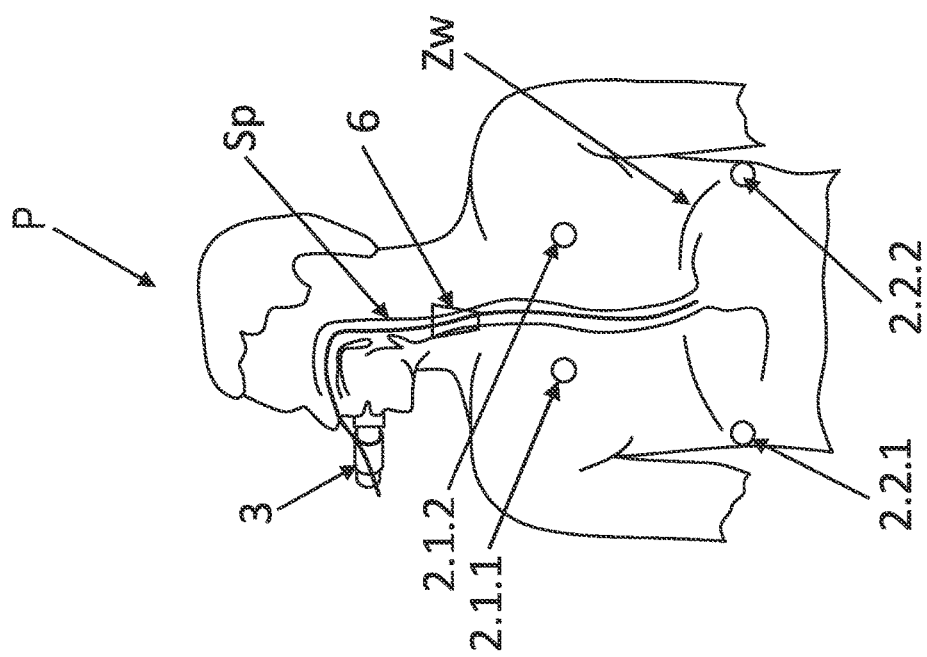
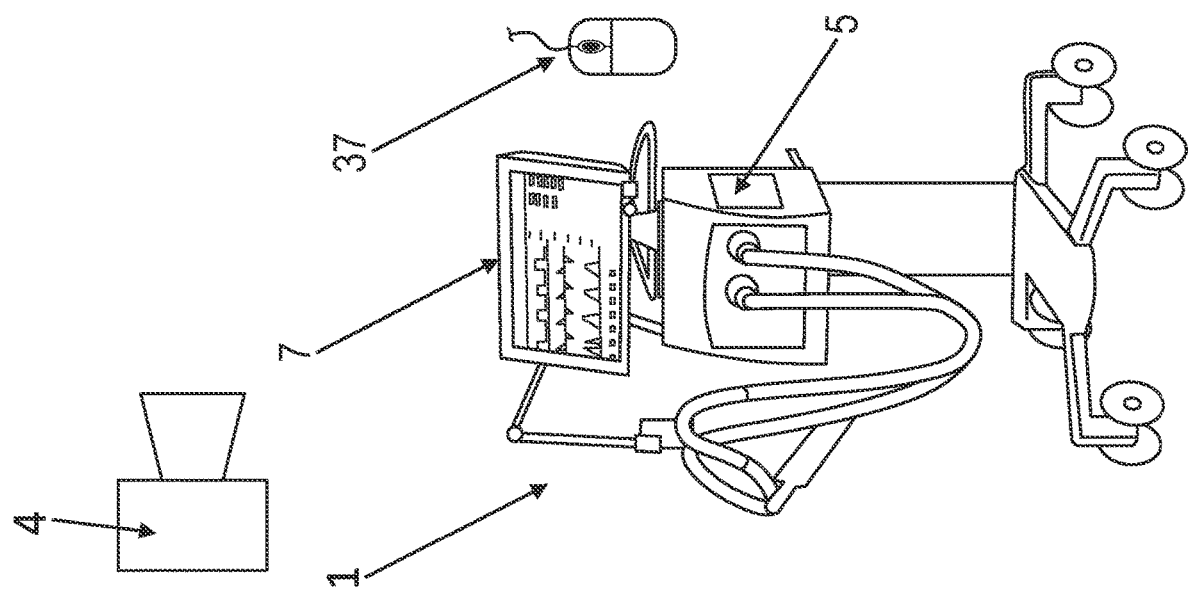
FIG. 1

SYSTEM AND PROCESS FOR DISPLAYING MEDICAL ALARMS

CROSS REFERENCE TO RELATED APPLICATIONS

This application claims the benefit of priority under 35 U.S.C. § 119 of German Application 10 2019 008 406.3, filed Dec. 4, 2019, the entire contents of which are incorporated herein by reference.

TECHNICAL FIELD

The present invention pertains to a system with a medical device, with a signal processing unit, with an output unit and preferably with an input unit, wherein the signal processing unit receives measured values from at least one patient sensor, detects alarms and actuates the output unit, wherein the actuated output unit is capable of outputting information visually to a user and wherein the optional input unit is capable of detecting user inputs. The present invention further pertains to a process for displaying medical information with the use of such a system.

TECHNICAL BACKGROUND

A ventilation system with a supply unit and with a display unit 15 is described in DE 10 2016 001 139 A1. A generator marker 23 is displayed along a time axis 19 for consecutive times. The generator marker 23 is positioned such that the ratio of its distance from the time axis 19 to the distance between the time axis and a boundary line 21 is equal to the ratio of a first generator parameter to the sum of the first generator parameter and a second generator parameter minus a first user parameter.

US 2014/0 275 819 A1 shows a patient monitoring device (medical monitoring device) with a plurality of sensors, which monitor each a respective physiological parameter of a patient. A signal processing unit (processing circuitry 204) receives measured values from the sensors and actuates an output unit (device 200 with displays 202) as well as an alarm generation unit (alarm mechanism 216). The respective time curve of different signals, which describe each a physiological parameter of the patient, as well as alarm marker shadings and alarm marker lines at the respective times in case of values deviating from a normal value, are displayed on the display screen. A user can shift the displayed time period and enlarge a display.

Devices and processes for monitoring a patient (patient monitoring) and for displaying medical alarms are also described in US 2003/0 200 117 A1, US 2005/0 038 332 A1, US 2008/0 078 390 A1, US 2011/0 138 311 A1, US 2013/0 246 089 A1, US 2018/0 277 243 A1 and US 2018/0 300 919 A1.

SUMMARY

An object basic object of the present invention is to provide a system comprising a medical device, an output unit and a signal processing unit as well as a process for displaying alarms on an output unit, wherein it shall be possible to display a plurality of alarms ergonomically even if a display surface of the output unit is small compared to the number of detected alarms.

The object is accomplished by a system having the features of the invention. Advantageous embodiments of the system according to the present invention are also advantageous embodiments of the process according to the present invention and vise versa, insofar as practical.

The system according to the present invention comprises a medical device, especially a ventilator or an anesthesia device. The medical device comprises at least one patient sensor, preferably a plurality of patient sensors, or it can be connected at least from time to time to at least one patient sensor. The patient sensor or each patient sensor is capable of measuring at least one respective variable, which occurs at or in a patient, preferably at least one vital parameter of the patient.

The system according to the present invention further comprises an output unit, which is capable of outputting information visually to a user, for example, on a display screen. The system further comprises a data-processing signal processing unit, which is capable of actuating the output unit and is preferably capable of detecting a user input.

The signal processing unit is capable of receiving measured values, which the patient sensor or the at least one patient sensor has generated. By the signal processing unit analyzing received measured values, the signal processing unit is capable of generating at least one signal. This signal is correlated with a variable, which is variable over time, and which occurs at or in the patient, for example, with a variable for the spontaneous breathing or for the heartbeat or for the oxygen level in the blood or for the $CO_2$ level in the exhaled breathing air of the patient. The signal processing unit is preferably capable of generating a plurality of signals and preferably of processing for this purpose measured values from different patient sensors.

At least one alarm criterion is predefined. The predefined alarm criterion or each predefined alarm criterion refers to the signal or to at least one signal, which the signal processing unit is capable of deriving from measured values of the patient sensor or of each patient sensor.

The signal processing unit is capable of automatically deciding whether the predefined alarm criterion or at least one predefined alarm criterion is met. The signal processing unit is capable of analyzing for this decision the generated signal or at least one respective generated signal. It is possible that different predefined alarm criteria refer to different signals or also to the same signal.

When the signal processing unit has decided that the alarm criterion or an alarm criterion is met, it has automatically detected an alarm. An alarm is present if at least one signal meets a predefined alarm criterion at a defined time. The signal processing unit is capable of detecting this alarm as well as the time at which the alarm criterion is met and has thus occurred. The same alarm criterion may be met several times, namely, at different times. At least two different alarm criteria may be predefined and therefore met for the same signal simultaneously or at different times. Every time the alarm criterion or an alarm criterion is met and this event is detected, the signal processing unit has again detected an alarm. Each alarm criterion defines a type of alarm. Each alarm belongs to one respective alarm type. It is possible that the same alarm criterion is met several times, namely, at different times. A plurality of identical alarm types have thus occurred one after another.

The signal processing unit is capable of actuating the output unit such that the actuated output unit displays different displays simultaneously at least from time to time, namely, simultaneously at least the following displays:
 an overall alarm sequence,
 an alarm reference section,
 a positioning display and a signal curve display or an alarm reference sequence or both a signal curve display and an alarm reference sequence.

The overall alarm sequence shows a time sequence of alarms, which were detected during a predefined overall time period. The overall alarm sequence preferably shows all the alarms that were detected during an overall time period, doing so preferably graphically.

The alarm reference section shows a time sequence of alarms that were detected in a predefined and preferably variable reference time window. This reference time window is a detail, i.e., a part of the overall time period. At least one other part of the overall time period is not located in the reference time window. The alarm reference section is a section of the overall time sequence.

Both the overall alarm sequence and the alarm reference section extend, on the output unit, in the same time axis display direction. In many applications, this is a horizontal display direction on the display screen, namely, from left to right or also from right to left. A vertical display direction is possible as well.

The alarm reference section shows alarms in the reference window and it additionally provides a positioning display. This positioning display shows how the reference time window is positioned over time relative to the overall time period.

The signal curve display shows the time curve of the generated signal or of at least one generated signal, showing the respective time curve of the signal in the reference time window.

The alarm reference sequence shows a sequence of alarms that were detected in the reference time window, preferably each alarm that was detected in the reference time window.

The actuated output unit displays the overall alarm sequence, the alarm reference section together with the positioning display provided as well as the signal curve display and/or the alarm reference sequence simultaneously at least from time to time.

Both the overall alarm sequence and the signal curve display as well as the alarm reference sequence extend in the same time axis display direction.

The time scale for the signal curve display is finer than the time scale for the overall alarm sequence and finer than the time scale for the alarm reference section. The time scale for the alarm reference sequence is also finer than the time scale for the overall alarm sequence and finer than the time scale for the alarm reference section.

Both the alarm reference section and the alarm reference sequence refer to the reference time window. However, the alarm reference sequence shows alarms in the reference time window with a finer time scale than does the alarm reference section. The alarm reference section makes it easier for a user to compare the alarms that occurred in the reference time window with those that occurred in the overall time window.

It is possible that a single, finer time scale is used for the signal curve display and for the alarm reference sequence and a single, coarser time scale is used for the overall alarm sequence and for the alarm reference section. More than two different times scales are possible as well.

The term "finer time scale" will be defined below. It corresponds to the term "finer display scale" for geographic representations, e.g., for maps and street maps. The opposite of "finer time scale" is "coarser time scale."

Both the signal curve display and the alarm reference sequence assume a certain extension in space in the time axis display direction on a display surface of the display unit. The term "time scale" is defined as the ratio of the extension in space to the displayed time period, for example, in [mm] per [sec] or [inch] per [minute] or in [cm] or [inch] per [h]. In a display with a finer time scale, the same time period is displayed with a greater extension in space in the time axis display direction than in case of a coarser time scale. In other words: A time scale A is finer than a time scale B if a display with the time scale A displays the same time period with a greater extension in space than does a display with the time scale B.

On the one hand, it is frequently desirable precisely in medical settings to display a large number of alarms on an output unit in a single display. A viewer can use this global display to have an overview of a change over time of alarms and over increases in the frequency of alarms over time. On the other hand, a user wants to be able to recognize what is displayed, and the maximum possible extension, which the display surface of the output unit can have, is often limited to meet the requirements imposed on medical procedures and/or because no more space is available. The present invention shows a way of making it possible to display the internal status of the medical device of the system according to the present invention on the output unit relatively clearly and ergonomically.

At least one finer time scale and at least one coarser time scale, namely, a finer time scale for the signal curve display and for the alarm reference sequence, and a coarser time scale for the overall alarm sequence and for the alarm reference section are used according to the present invention. Each display with the finer time scale or with a finer time scale is still capable in many cases of displaying a fact in a rapidly perceivable manner and/or in sufficient detail if the output unit being used has relatively small dimensions and/or a relatively low resolution, for example, relatively few pixels. Each display with the coarser time scale or with a coarser time scale is capable in many cases of displaying a larger number of alarms simultaneously. A large number of alarms, which refer to a patient and which shall be displayed in a single display, are frequently detected in a relatively short time period precisely by the signal processing unit in a medical system. Each situation, which may be hazardous for a patient or is an indicator of a possible hazard, should be displayed precisely in a medical context.

According to the present invention, at least one display with the finer time scale and at least one display with the coarser time scale are displayed according to the present invention on the output unit. This feature eliminates the need to switch over between different time scales and thus it eliminates a user interaction, work time and attention of the user and in some cases it additionally also eliminates disinfection of the output unit, which would be necessary because of the user interaction, as well as computing time in some embodiments. In particular, it is not necessary to "zoom" into the reference time window and then "zoom" out of the reference time window back into the overall time period. A plurality of displays with at least two different time scales are rather displayed, instead, simultaneously with at least two different time scales. In addition, the positioning display, which is provided by the alarm reference section, shows how the reference time window is positioned relative to the overall time period. Such a positioning display would not be present in case of a simple switching between two different time scales.

The actuated output unit displays at the same time a sequence of alarms, which occurred during the overall time period, and a sequence of alarms in the reference time window. The overall alarm sequence preferably shows at least each alarm that is shown during the overall time period. The alarm reference section displays alarms, preferably all alarms, that were detected in the reference time window. It can be rapidly recognized hereby whether extraordinarily many or extraordinarily few alarms or an average number of alarms occurred during the alarm reference section compared to the overall time period.

The output unit displays according to the present invention by means of the positioning display how the reference time window is positioned in time relative to the overall time period. This positioning display is provided by means of the alarm reference section and of the overall alarm sequence, preferably by the alarm reference section being displayed as being positioned in a correctly timed manner relative to the overall alarm sequence, especially preferably by the section of the overall alarm sequence that refers to the reference time window being highlighted. For example, a box is placed around the section of the overall alarm sequence that falls within the reference time window, and it thus displays the alarm reference section. The positioning display provided according to the present invention makes it easier for a viewer to classify in time the display or each display that refers to the reference time window and/or to compare it to the overall alarm sequence. In addition, the alarm reference section shows alarms in the reference time window, preferably all alarms. Thanks to the alarm reference section, it is possible, but not necessary, to display the relative positioning in time in a separate display in addition to the displayed alarms or to display numerical time data. This saves space compared to a separate display of the positioning in time.

According to the present invention, the signal processing unit is capable of actuating the output unit such that the actuated output unit displays a signal curve display and/or an alarm reference sequence as well as an overall alarm sequence. The signal curve display shows the curve of at least one signal over time in the reference time window. The overall alarm sequence shows a sequence of alarms in the overall time period. These simultaneously displayed displays make it easier for a user to find an explanation for an alarm and for the occurrence thereof, doing so without switching between different displays by a user interaction. The alarm reference sequence shows a sequence of alarms over time in the reference time window. The extension of the signal curve display and the extension of the alarm reference sequence—viewed in the time axis display direction—are preferably at least as great as the extension of the overall alarm sequence.

In summary, the system according to the present invention and the process according to the present invention offer a higher level of ergonomics compared to systems and processes in which all alarms and signal curves over time are displayed with the same time window, and also compared to systems and processes in which a user must switch between different displays having different time scales by a user interaction. This higher level of ergonomics is especially relevant in case of a relatively small output unit. The system according to the present invention and the process according to the present invention eliminate the need to switch between different displays, especially between displays with different time scales. This effect improves the ergonomics as well.

According to the present invention, the reference time window is a detail of the overall time period. In one embodiment, the length of the reference time window is at most 70%, preferably at most 50%, especially preferably at most 35% and especially at most 10% of the length of the overall time period. This embodiment makes it possible, on the one hand, to display alarms and/or signal curves, which have occurred in the reference time window, in a relatively detailed form, and, on the other hand, to display all alarms in the overall alarm sequence. In addition, it is possible to display the positioning over time of a reference time window that is relatively short compared to the overall time period. All this is displayed simultaneously on the output unit without a user interaction for switching being necessary. Such numerical data cannot be detected as rapidly as graphic data.

The positioning over time of the reference time window relative to the overall time period is preferably variable. In particular, the reference time window can be shifted such that a time distance is formed between the reference time window and the current time. The alarm reference section, the alarm reference sequence and the signal curve display are preferably adapted automatically to a change in the reference time window.

According to the present invention, the signal processing unit is capable of actuating the output unit such that the actuated output unit displays the signal curve display and/or the alarm reference sequence. In one embodiment, the actuated output unit displays both the signal curve display and the alarm reference sequence. The signal curve display and the alarm reference sequence preferably refer to the same finer time scale and are preferably positioned in a correctly timed manner in relation to one another. It is also possible that the actuated output unit displays only the signal curve display or only the alarm reference sequence. In another embodiment, the actuated output unit displays optionally the signal curve display or the alarm reference sequence, for example, depending on a corresponding user input.

The signal curve display and the alarm reference sequence are preferably displayed with the same finer time scale and they extend in the same time axis display direction. The signal curve display on the output unit is especially preferably positioned in a correctly timed manner relative to the alarm reference sequence. This common positioning, which is preferably a correctly timed positioning, makes it easier for a user rapidly to detect which signal values have led to an alarm that is being displayed in the alarm reference sequence, and where this alarm and the signal values that have led to the alarm are positioned in time.

The overall alarm sequence and the alarm reference section are preferably displayed with the same coarser time scale. The alarm reference section is preferably displayed such that it is positioned in a correctly timed manner relative to the overall alarm sequence. This makes it easier for a user to detect the positioning in time of the reference time window relative to the overall time period and the positioning in time of the alarms in the reference time window relative to the alarms in the overall time period.

According to the present invention, the actuated output unit displays how the alarm reference section is positioned in time relative to the overall alarm sequence, doing so by means of the positioning display. In one embodiment, the alarm reference section is displayed as a part of the overall alarm sequence and is preferably highlighted in this sequence the overall alarm sequence, and the relative positioning is displayed hereby. This embodiment does not require any additional place on the output unit to display the positioning in time.

In another embodiment, the alarm reference section is displayed separately from the overall alarm sequence, but it is preferably also displayed in a correctly timed manner in this other embodiment as well, and both displays are displayed during simultaneously and together. The relative positioning in time is shown by the correctly timed positioning. It is also possible for the actuated output unit to display a time axis for the overall time period on the output unit and to mark the reference time window in a marked form in this time axis.

According to the present invention, the output unit shows how the alarm reference section is positioned in time relative to the overall alarm sequence. This display of the positioning in time is preferably a graphic display. This makes it unnecessary for a user to read numerical time data and to have to mentally analyze and/or assess them. The positioning in time of the alarm reference section relative to the overall alarm sequence can be detected by a user by means of the graphic positioning display more rapidly and more intuitively than can other conceivable displays.

According to the present invention, the signal processing unit is capable of actuating the output unit such that the actuated output unit displays at least two time sequences of alarms, namely, an overall alarm sequence and an alarm reference section. The overall alarm sequence shows the alarms that have occurred during the overall time period, and the alarm reference section shows the alarms of the overall alarm sequence that have occurred in the reference time window. The overall alarm sequence and the alarm reference section are preferably displayed with the same coarser time scale. The actuated output unit especially preferably displays the alarm reference section as a section of the overall alarm section, for example, highlighted in the overall alarm sequence. This embodiment saves space on the output unit compared to a display in which the alarm reference section is displayed separately in space from the overall alarm sequence. It is, however, also possible that the alarm reference section is displayed separately from the overall alarm sequence.

The system preferably comprises, furthermore, an input unit, which is capable of detecting user inputs, for example, a touchscreen. By means of this input unit the user is capable especially of selecting a displayed alarm and of changing the reference time window. In particular, the user is capable of shifting the reference time window in the overall time period back and forth and of positioning it at a desired time.

In a variant of this embodiment, the signal processing unit is capable of detecting the selection of a displayed alarm by a user. It is possible that this displayed alarm is located within the overall time period, but not in the reference time window. After selection of an alarm, the signal processing unit is capable of actuating the output unit such that the reference time window is automatically shifted and the selected alarm is located now in the reference time window.

The user is capable of selecting an alarm that is displayed in the alarm reference section or in the alarm reference sequence. After selecting an alarm, the actuated output unit is capable of displaying at least one piece of information via the selected alarm. For example, at least one of the following pieces of information is displayed:
 a textual description of an alarm criterion, which has been detected as having been met and has led to the alarm,
 the time at which the alarm was detected,
 a time period during which this alarm was present,
 a marking of the relevance of the alarm,
 at least one signal value, which has led to the alarm, and
 a predefined desired range for the signal, which has led to the alarm, wherein the alarm is preferably triggered by a signal value outside this desired range.

At least one alarm criterion is predefined according to the present invention. At least two different alarm criteria are preferably predefined. Each alarm criterion defines an alarm type. The same alarm criterion may be met repeatedly, namely, at different times. A plurality of alarms of the same type are detected one after another in this case. On the whole, at least two different alarm types are consequently defined. When a predefined alarm criterion is met and detected, an alarm of the associated alarm type has occurred and has been detected.

The signal processing unit is capable of detecting a selection of an alarm by a user. After the signal processing unit has detected the selection of an alarm, it is capable of actuating the output unit such that the actuated output unit will display the following: Each additional alarm, which belongs to the same alarm type as the selected alarm, is displayed compared to the other displayed alarms in a highlighted form in the overall alarm sequence and/or in the alarm reference section and/or in the alarm reference sequence.

In a preferred embodiment, the signal processing unit retains the selection of an alarm until it has detected the selection of another alarm. This selection of the alarm is, in particular, preferably also retained when the reference time window or a reference time described below is changed based on a user input, especially preferably also if the selected alarm is located prior to the shifting of the reference time window in the reference time window and is not located there any longer thereafter.

The signal processing unit actuates the output unit according to the present invention such that the actuated output unit displays a signal curve display, an alarm reference section and/or an alarm reference sequence, all of which refer to the reference time window. This reference time window is a section, i.e., a part of the overall time period. The displayed overall alarm sequence refers to the overall time period. The overall alarm sequence refers to the overall time period. In a preferred embodiment, the signal processing unit is capable of detecting a user input in order to change, especially in order to shift the reference time window or in order to change the length thereof. By the user prompting a change the length in time of the reference time window by a user input, the finer time scale or each finer time scale is preferably changed as well. In case of a simple shift of the reference time window, the finer time scale or each finer time scale will, by contrast, remain unchanged. After the signal processing unit has detected the required change in the reference time window, the signal processing unit actuates the output unit. The correspondingly actuated output unit adapts the alarm reference section as well as the signal curve display and/or the alarm reference sequence automatically to the changed reference time window.

The actuated output unit leaves the displayed overall alarm sequence unchanged at least when the changed reference time window is completely within the overall time period. If the changed reference time window is not completely within the overall time period, the signal processing unit does, by contrast, change the overall time period and/or the reference time window such that the reference time window will then again be located completely within the overall time period, and it will adapt the overall alarm sequence displayed correspondingly.

In a preferred embodiment, the actuated output unit additionally displays a reference time, which is within the reference time window. This reference time is displayed in the signal curve display and/or in the alarm reference section and/or in the alarm reference sequence. The actuated output unit preferably displays additionally the value of at least one signal at this reference time, especially preferably the respective value of at least one or even each signal displayed in the signal curve display.

The signal processing unit is capable of detecting a user input, with which a user changes, especially shifts the displayed reference time. This user input may comprise the numerical input of a time or also the step of shifting a symbol displayed for the reference time on a display screen. As a response to such a user input, the signal processing unit is capable of actuating the output unit. The output unit actuated as a response displays in the signal curve display and/or in the alarm reference section and/or in the alarm reference sequence the changed reference time and preferably the signal value or each signal value at the changed reference time.

If the changed reference time is outside the reference time window that was used before the change of the reference time, the signal processing unit preferably additionally changes the reference time window such that the reference time changed corresponding to the user input will be in the changed reference time window. In another embodiment, it places the reference time at a boundary of the reference time window, which has been left unchanged. In another embodiment, the signal processing unit prompts the outputting of an error message. The user can then change the reference time window or the reference time.

In a variant of this embodiment, the signal processing unit checks whether an alarm has occurred and has been detected at the changed reference time. If an alarm has occurred and been detected at the changed reference time, the signal processing unit uses this alarm as the selected alarm. It is not necessary to select this alarm directly.

In a variant of this embodiment, a user is capable of selecting at first an alarm. The system according to the present invention is capable of detecting this selection of an alarm by the user. The step of selecting an alarm triggers the step that the time at which this alarm has occurred is used as the reference time. If the selected alarm was previously located outside the reference time window, the reference time window is shifted such that the selected alarm is now in the reference time window. In addition, the respective value of at least one signal of the signal curve display is displayed at this reference time. This embodiment makes it possible for a user to have a view over a situation at the time of the alarm with a single interaction. The embodiment in which an alarm can be selected may be combined with the embodiment in which a reference time can be selected.

The embodiment in which an alarm can be selected may be combined with the embodiment in which a reference time can be selected. As a result, two different possibilities of interaction become available to the user.

According to the present invention, the actuated output unit displays an overall alarm sequence, which refers to an overall time period, as well as an alarm reference section and optionally an alarm reference sequence, which refer to a reference time window. The actuated output unit preferably displays each alarm by means of a symbol each in the overall alarm sequence and/or in the alarm reference section and/or in the alarm reference sequence. This embodiment saves space compared with a textual description of the alarm and makes it possible for a user to detect the displayed situation more rapidly.

In a variant of this embodiment, a predefined symbol is assigned to each predefined alarm criterion and thus to each possible alarm type. The actuated output unit displays as a symbol for an alarm the symbol that is assigned to the alarm criterion and hence to the alarm type of this alarm. A plurality of identical alarms differ by the respective time at which they occur.

In one embodiment, a different symbol is assigned to each alarm type. A different embodiment, which is more clear in many cases, is this: A respective relevance is associated with each alarm criterion. A respective symbol is assigned to each relevance; by contrast, different symbols are assigned to different relevance. The same symbol is therefore assigned in this preferred embodiment to different alarm criteria of equal relevance. The alarms are displayed on the output unit by the symbols of the alarm types in a correctly timed manner. This embodiment reduces the number of necessary symbols compared to an embodiment in which a special symbol of its own is assigned to each alarm criterion and hence to each alarm type. In addition, relevant alarms can be recognized more rapidly. In one embodiment, the actuated output unit displays, depending on a user input, either the symbols for the relevance or the symbols for the alarm types.

The actuated output unit displays according to the present invention an overall alarm sequence, which refers to an overall time period, as well as an alarm reference section and optionally an alarm reference sequence, which refer to a reference time window. The actuated output unit preferably displays additionally an alarm description sequence. This alarm description sequence comprises a textual alarm description per alarm of a sequence of alarms. This alarm sequence belongs to the time sequence of alarms that is displayed in the overall alarm sequence, preferably to a sequence of the alarm reference sequence. The textual alarm description extends in a list direction. This list direction is preferably at right angles to the time axis display direction, for example, from top to bottom. The respective writing direction of each textual alarm description in the alarm description sequence is at right angles to the list direction and is therefore parallel in a two-dimensional display to the time axis display direction.

The textual description of an alarm preferably comprises at least one of the following pieces of information:
  a textual description of an alarm type, to which this alarm belongs,
  a symbol for this alarm type,
  the time at which the alarm was detected,
  a time period, during which this alarm was present,
  a marking of the relevance of the alarm, and
  at least one signal value, which has led to the alarm.

According to the embodiment just described, the alarm description sequence displayed comprises a textual alarm description per alarm of a sequence of alarms. The signal processing unit is preferably capable of detecting a user input, according to which the sequence of alarms, whose alarm descriptions are displayed in the alarm description sequence, shall be changed, i.e., in order for another alarm sequence to be displayed. After detecting such a change, the signal processing unit is capable of actuating the output unit such that the actuated output unit displays the alarm descriptions for the alarms of the changed sequence, preferably again in the list direction.

In a variant of the embodiment with the alarm description sequence, the signal processing unit is capable of detecting the selection of an alarm description, wherein the selected alarm description is displayed in the alarm description sequence. This selected alarm description belongs to an alarm that was detected during the overall time period, preferably to an alarm in the reference time window. The signal processing unit preferably uses the alarm, to which the selected alarm description refers, as the selected alarm.

In particular, it displays each additional alarm, which belongs to the same alarm type as the selected alarm, in a highlighted form compared to the other displayed alarms.

In another variant of the embodiment with the alarm description sequence, the signal processing unit displays the alarm reference sequence with alarms that have been detected in the reference time window as well as a correlation indicator. The correlation indicator comprises a leading element and a led element.

In a first alternative of this variant, the leading element refers to an alarm description in the alarm description sequence. The led element (guided element) refers to the alarm in the alarm reference sequence and/or in the alarm reference section to which this alarm description refers. In a second alternative of this variant, the leading element refers to an alarm in the alarm reference sequence and/or in the alarm reference section and the led element (guided element) refers to the alarm description in the alarm description sequence that refers to this alarm.

This embodiment makes it easier to find the corresponding alarm description for an alarm in the alarm reference sequence or conversely, the corresponding alarm for an alarm description in the alarm reference sequence. If, for example, the leading element points towards another alarm description or to another alarm on the basis of a user input, the led element is carried along correspondingly.

According to the present invention, the actuated output unit displays a signal curve display and/or an alarm reference sequence, both of which refer to the reference time window. The signal processing unit checks automatically whether a predefined alarm criterion is met. In a preferred embodiment, the signal processing unit actuates the output unit such that the output unit will display the following: If a signal curve displayed in the signal curve display meets at least one predefined alarm criterion in the reference time window, the output unit highlights in the display the section of the displayed signal curve and/or the time section in the overall time period and/or in the reference time window that causes this alarm criterion to be met. For example, the output unit displays in a highlighted form the section of the signal curve that is outside a predefined desired range for this signal, and or the section of the reference time window in which the values of the signal are outside the desired range. This desired range may have been predefined in advance or have been changed over time and have been calculated by the signal processing unit in advance.

This embodiment makes it easier for a user to examine a displayed alarm more closely, without a textual description having necessarily to be displayed on the display unit.

Contrary to a textual description, this embodiment does not in many cases require any additional space on the display unit.

The system according to the present invention comprises a signal processing unit and an output unit. In one embodiment, this signal processing unit is split between two signal processing devices, which are preferably located at remote locations in space from one another and are connected to one another by a data link. The first signal processing device is configured to receive measured values from the patient sensors, to generate at least one signal, to check whether an alarm criterion is met, and to detect alarms. The second signal processing device is configured to receive the information on the signals and on alarm histories from the first signal processing device and to actuate the output unit.

The signal processing device is preferably a part of a medical device or is associated with this medical device, and the detected alarms refer to a patient, who is connected to this medical device from time to time. The second signal processing device is separated in space from the medical device and from the first signal processing device and is in a data link with the first signal processing device at least from time to time. It is possible that the first signal processing device additionally actuates an output unit of the medical device, preferably such that the output unit of the medical device operates as was described above. It is possible that the second signal processing device is connected to a plurality of first signal processing devices, especially preferably to such of different medical devices. The second signal processing device and/or the output unit actuated by the second signal processing device are arranged, for example, in a center.

In a variant of this embodiment, the system belongs to a system with at least two medical devices, which are connected to one another at least from time to time via a data network. At least two of these medical devices comprises a first signal processing device each, which is configured as was just described. Each first signal processing device causes messages on alarms and the times at which they occur to be transmitted to the second signal processing device. For example, each first signal processing device has write access at least from time to time to the same central memory and it writes information on the alarms, which it has detected, into this central memory.

The second signal processing device is in a respective data link with these two first signal processing devices, for example, by the second signal processing device having read access to the central memory at least from time to time and reading information on alarms into the memory. The second signal processing device actuates the output unit such that the output unit optionally displays inputted alarms and optionally further patient data from one medical device or from the other medical device. It is also possible that the actuated output unit displays alarms from both medical devices at the same time. The second signal processing device and the output unit thus operate as a central system in order to monitor a plurality of first medical devices.

The present invention will be described below on the basis of a plurality of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view showing a patient, who is being mechanically ventilated at least from time to time, a ventilator and the patient sensors used;

DESCRIPTION OF PREFERRED EMBODIMENTS

Figure 2:
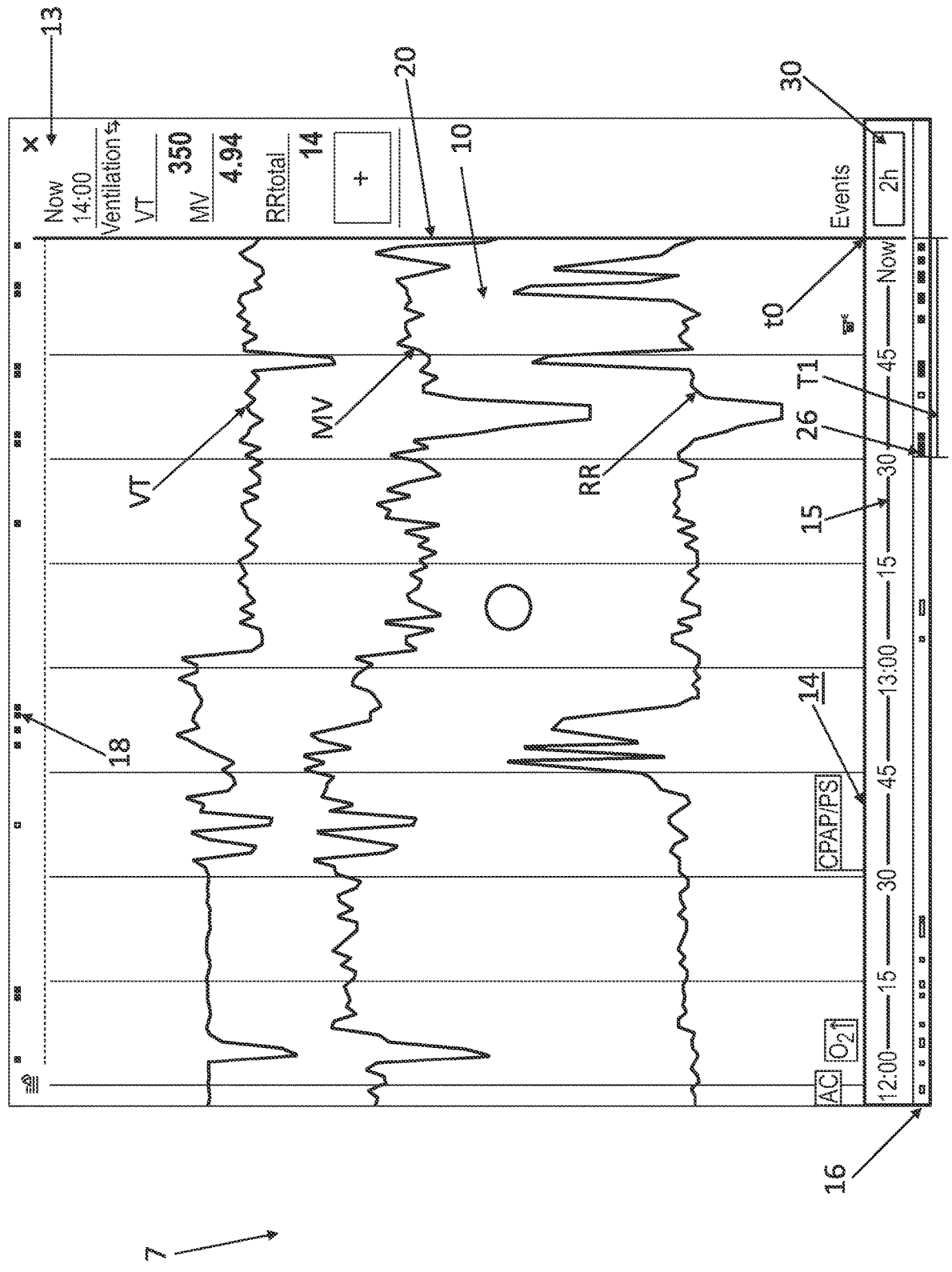
FIG. 2 is a display view showing an initial splitting of the display screen of the medical device.

Referring to the drawings, the present invention is used in the exemplary embodiment for a ventilator with a display screen and with a signal processing unit.

FIG. 1 shows a patient P with an esophagus Sp and with a diaphragm Zw, wherein said patient P is ventilated mechanically by a ventilator 1 and is connected to a connection piece 3 in front of his mouth.

A first set 2.1.1 and 2.1.2 of measuring electrodes located close to the heart of the patient P as well as a second set 2.2.1 and 2.2.2 of measuring electrodes located close to the diaphragm and additionally a ground electrode, not shown, are positioned on the skin of the patient P. An electrical respiratory signal and/or an electrical cardiogenic signal, which describe the activity of the respiratory muscles and the activity of the heart muscles of the patient P, can be derived from the measured values of the measuring electrodes 2.1.1 through 2.2.2.

A pneumatic sensor 6, e.g., a probe or a balloon, is optionally located in the esophagus Sp and close to the diaphragm Zw. A pneumatic signal, which describes the pressure Pes (pressure in esophagus) in the esophagus Sp and is correlated with the pressure in the airways, can be derived from the measured values of this pneumatic sensor 6. The airway pressure Paw (pressure in airway) at the connection piece 3 can be derived from measured values of another, preferably pneumatic sensor, which is arranged, for example, in the ventilator 1. An optical sensor 4 optionally measures the geometry of the body of the patient P. An indicator of the filling level of the lungs of the patient P, which varies over time, can be derived from measured values of the optical sensor 4, i.e., from the measured body geometry.

FIG. 1 shows a ventilator 1 comprising a connection piece 3 and an output unit with a touch-sensitive display screen 7, which is capable of outputting information in a visual form to a user. This ventilator 1 carries out the mechanical ventilation of the patient P. In addition, an optional, additional input unit with a computer mouse 37 is shown.

A data-processing signal processing unit 5 of the ventilator 1 receives measured values from the sensors 2.1.1 through 2.2.2, 3, 4, 6, calculates patient-related signals from these measured values and prompts the display of selected signals on the display screen 7. The signal processing unit 5 actuates a processor for the display screen 7 and prompts thereby the display of the time curves of different signals and additional pieces of information. The display screen 7 and this processor belong to an output unit of the exemplary embodiment.

Examples of such patient-related signals are the following signals:
  VT ("ventilation," tidal volume, which is the quantity of breathing air that flows into the lungs of the patient P during a breath during inhalation, in [mL],
  MV ("minute volume," the quantity of breathing air fed into the lungs per unit of time, in [L/minute]),
  RR (Respiratory Rate, the breathing frequency of the patient P, which is predefined at the ventilator 1 in the case of an exclusive mechanical ventilation and/or is measured and it is preferably measured when the patient P is breathing himself by counting how often the breath flow changes its direction),
  HR (Heart Rate, heartbeat frequency, measured, for example, as the number of R peaks of an electrical cardiogenic signal or EMG signal per minute, in [1/minute]), and
  SpO2 (the oxygen level in the blood; it is measured by pulsometry).

The signal processing unit 5 receives measured values from sensors, for example, from the sensors 2.1.1 through 2.2.2, 3, 4, 6 shown in FIG. 1 and generates patient-related signals from measured values. The signal VT (quantity of breathing air) is calculated by the signal processing unit 5 integrated over a plurality of measured values, which describe the flow of breathing air at different times during a breath. The signal MV (quantity of fed breathing air) is calculated from the signal VT, for example, by a suitable averaging or from a signal section of this signal VT of a 1-minute duration.

The display screen 7 may be a part of the ventilator 1 or also be separated in space from the ventilator 1 and it may belong, for example, to a smartphone or another portable device. The signal processing unit 5 may also be separated in space from the ventilator 1 and belong, e.g., to the portable device.

A user can make inputs and thereby change the display on the display screen 7, which will be described below. The display screen 7 is preferably configured as a touch-sensitive display screen (touchscreen), and the user can touch and move an element displayed on the display screen 7, e.g., by a movement with a finger over the display screen 7. It is also possible that the ventilator 1 or the portable device located separately in space comprises an additional input unit, for example, a mouse 37 and/or a keyboard or a unit that recognizes speech inputs.

The signal processing unit 5 is capable of detecting alarms. Each detected alarm refers to at least one signal, which the signal processing unit 5 has generated by analyzing measured values. An alarm is present and is detected automatically if this signal meets a predefined alarm criterion at at least one scanning time and/or for a time period that is longer than a predefined minimum time period.

A desired range, in which the signal values shall be located, is preferably predefined for each patient-related signal, which can be generated as a function of measured vales of the sensors 2.1.1 through 2.2.2, 3, 4, 6 positioned at the patient P. This desired range may be constant over time or is calculated during the use depending on measured values and may therefore be variable over time. An alarm criterion for this signal is met if the value of a signal is below the lower limit of the desired range at at least n1 scanning times. Another alarm criterion is met if the value of a signal is above the upper limit of the desired range at at least n2 scanning times. The numbers n1 and n2 are predefined and may be equal or differ from one another. An alarm criterion may also be met if the change over time or the rate of change of a signal is above a predefined change limit.

The signal processing unit 5 checks continuously, e.g., at a predefined scanning frequency, whether at least one patient-related signal meets a predefined alarm criterion. The signal processing unit 5 preferably checks preferably for each signal, whether an alarm criterion predefined for that signal is met. If yes, the signal processing unit 5 has detected an alarm of a defined alarm type. The alarm criterion detected as having been met specifies the alarm type of the detected alarm. The signal processing unit 5 detects the alarm type and the time or the earliest time at which this alarm occurred. An alarm of the same alarm type may, of course, occur several times one after another. Each alarm is characterized by the alarm type and by a time of occurrence.

The signal processing unit 5 compares especially the patient-related signals with predefined limit values, for example, with the limits of a desired range, and generates a patient-related alarm when a signal value is above an upper limit value or below a lower limit value.

An example of an alarm on the basis of a deviating patient-related signal is "Pressure high"—the airway pressure Paw (pressure difference from the ambient pressure) is above a predefined upper limit value—is above a predefined upper limit value, equaling, for example, 27 mbar. Another example is "MV low"—the quantity of breathing air fed into the lungs is below a lower limit value, equaling, e.g., 3.65 L/minute. Another alarm is present if the respiratory rate is above an upper limit ("RR high").

The signal processing unit 5 is also capable of monitoring system states of the ventilator 1 and of generating an equipment-related alarm, for example, the alarm "battery state of charge low". This alarm is triggered when the state of charge of the battery of the ventilator 1 is so low that this battery could not override a temporary failure of a stationary power supply grid or the disconnection of the ventilator 1 from the power supply grid for a sufficiently long time. Another equipment-related alarm is generated, e.g., when a sensor cannot supply a valid measured value.

The signal processing unit 5 is capable of detecting and processing inputs of a user. The signal processing unit 5 actuates the display screen 7 as a function of detected user inputs and prompts the display screen 7 to display in response to the user input different displays, which will be described below.

FIG. 2 shows an exemplary initial splitting of a partial area of the display screen 7. The present invention is preferably not used for the display in the rest of the display screen 7. The following areas of the display screen 7 will be shown as an example:
  The time curves of three signals VT, MV and RR are displayed in the situation being shown in a central signal curve area 10 of the display screen 7. The user can specify the signals whose time curves will be displayed.

A reference time t0 (here: 02:00 pm) as well as the values of the three signals VT (350 mL), MV (4.94 L/minute) and RR (14/minute) are displayed at this reference time t0 in a signal value area 13 to the right of the central signal curve area 10. In the situation being shown, the current time (now) is the reference time t0, and the current time is therefore shown, and it changes with the advancement of time.

An alarm overview display 14 is shown in a lower area of the display screen 7. This alarm overview display 14 comprises a reference time axis 15 and an overall alarm sequence 16 of alarms as well as an alarm reference section 26, which will be described in more detail below.

The three time curves of three signals VT, MV, RR, which are displayed in the signal curve area 10, refer to a reference time window T1, which runs from 12:00 pm to 02:00 pm in this case. The reference time axis 15 in the alarm overview display 14 refers to this reference time window T1. The three signal time curves VT, MV, RR shown likewise refer to the reference time axis 15 and show the respective curve of the signal in the reference time window T1.

A reference time line 20 on the display screen 7 is at right angles to the reference time axis 15 and displays the variable and changeable reference time t0; it is the current time 02:00 pm in the situation being shown in FIG. 2. This reference time line 20 likewise refers to the reference time axis 15. The reference time t0 is initially the current time, i.e., 02:00 pm here. A user can predefine an earlier time as the changeable reference time t0, which will be described below.

A plurality of different alarms are displayed under the reference time axis 15 in the alarm overview display 14. Each alarm refers to a signal in the example being shown to the signal MV or to the signal VT or to the signal RR, and it is detected when a predefined alarm criterion is met. Each predefined alarm criterion specifies a respective alarm type, for example, the alarm types "Signal MV too low" ("MV low") or "Signal RR too high:" ("RR high").

A time sequence of alarms is displayed in an overall alarm sequence 16, which is located under the reference time axis 15. This overall time sequence 16 refers to an overall time period T during the therapy of the patient P, wherein the overall time period T is longer than the reference time window T1 displayed by the reference time axis 15. The reference time window T1 is consequently a section of the overall time period T. The time scale of the reference time axis 15 is finer than the time scale of the overall time sequence 16. The overall alarm sequence 16 does not use the reference time axis 15, but an overall time axis, which is not displayed and is not described by numerical time data in one embodiment in order to save space on the display screen 7. This overall time axis displays the same time period with a smaller space than does the reference time axis 15, and the overall time axis for the overall time period T is therefore preferably just as long as the reference time axis 15 for the reference time window T1, even though the overall time period T is longer than the reference time window T1. The overall time axis inevitably has a coarser time scale than the reference time axis 15.

The overall alarm sequence 16 is always displayed in one embodiment. It offers an overview over the entire time period of the therapy and makes it possible for a user to directly select another reference time window T1. In another embodiment, the overall alarm sequence 16 is faded in or faded out depending on a user input.

An alarm reference section 26 of this overall alarm sequence 16 indicates when and which alarm types have occurred in the reference time window T1 and how the reference time window T1 is positioned in the time period T. The alarm overview display 14 consequently shows by the alarm reference section 26 and by the overall alarm sequence 16 the section of the overall time period T that the reference time window T1 currently occupies, i.e., a positioning display. This section is variable. The overall time axis is used for the alarm reference section 26 in the exemplary embodiment.

In the embodiment shown, the alarm reference section 26 is a section of the overall alarm sequence 16, which saves space on the display screen 7. It is also possible that the alarm reference section 26 is displayed separated in space from the overall alarm sequence 16. Each alarm occurring in the reference time window T1 is consequently displayed twice in this deviating embodiment, namely, once in the overall alarm sequence 16 and once in the alarm reference section 26.

The time period of the reference time window T1, here 2 hr., is displayed in a time period window 30. An initial duration in time is predefined. A user can change the time period of the reference time window T1 and also change the reference time window T1 in this manner. For example, the user touches the time period window 30 and can then predefine a new time period, e.g., by means of a slide control and/or by means of faded-in keys "+" and "−" and/or by entering a numerical value. The alarm types of this alarm reference section 26 and hence the alarm types, which were detected in the reference time window T1, are additionally displayed in an alarm reference sequence 18 above the signal curve area 10.

Each alarm, which was detected in the reference time window T1, is displayed in the overall alarm sequence 16 and in the alarm reference sequence 18 by the symbol for the corresponding alarm type. The times of the alarms displayed in the alarm reference sequence 18 refer to the reference time window T1, which is displayed with the use of the reference time axis 15. The reference time axis 15 is consequently also used for the alarm reference sequence 18. The alarm reference sequence 18 is likewise related to the reference time axis 15 and uses the same time finer scale as the signal curve display 10.

In one embodiment, a separate symbol is predefined for each alarm type, and each alarm is displayed in the overall alarm sequence 16, in the alarm reference sequence 18 and in the alarm reference section 26 by means of the symbol for the alarm type.

However, a sufficient number of symbols, which can be displayed in different manners, are not available in many applications. A plurality of possible relevance levels, for example, "low," "medium" and "high," are therefore predefined for an alarm in the exemplary embodiment. A relevance is assigned to each alarm type, and a symbol, for example, a green circle for "low," a yellow circle for "medium" and a red circle for "high" (i.e., a traffic light display), is assigned to each relevance. Each alarm is displayed in the sequences 16, 18 and 26 by means of a circle or another symbol, and the color and/or the shape of this symbol depends on the relevance of the alarm type. The relevance "high," which is displayed with a red circle 17.1, is assigned to the alarm type "MV low," and the relevance "medium," which is displayed with a yellow circle 17.2, is assigned to the alarm type, cf. FIG. 11.

Figure 3:
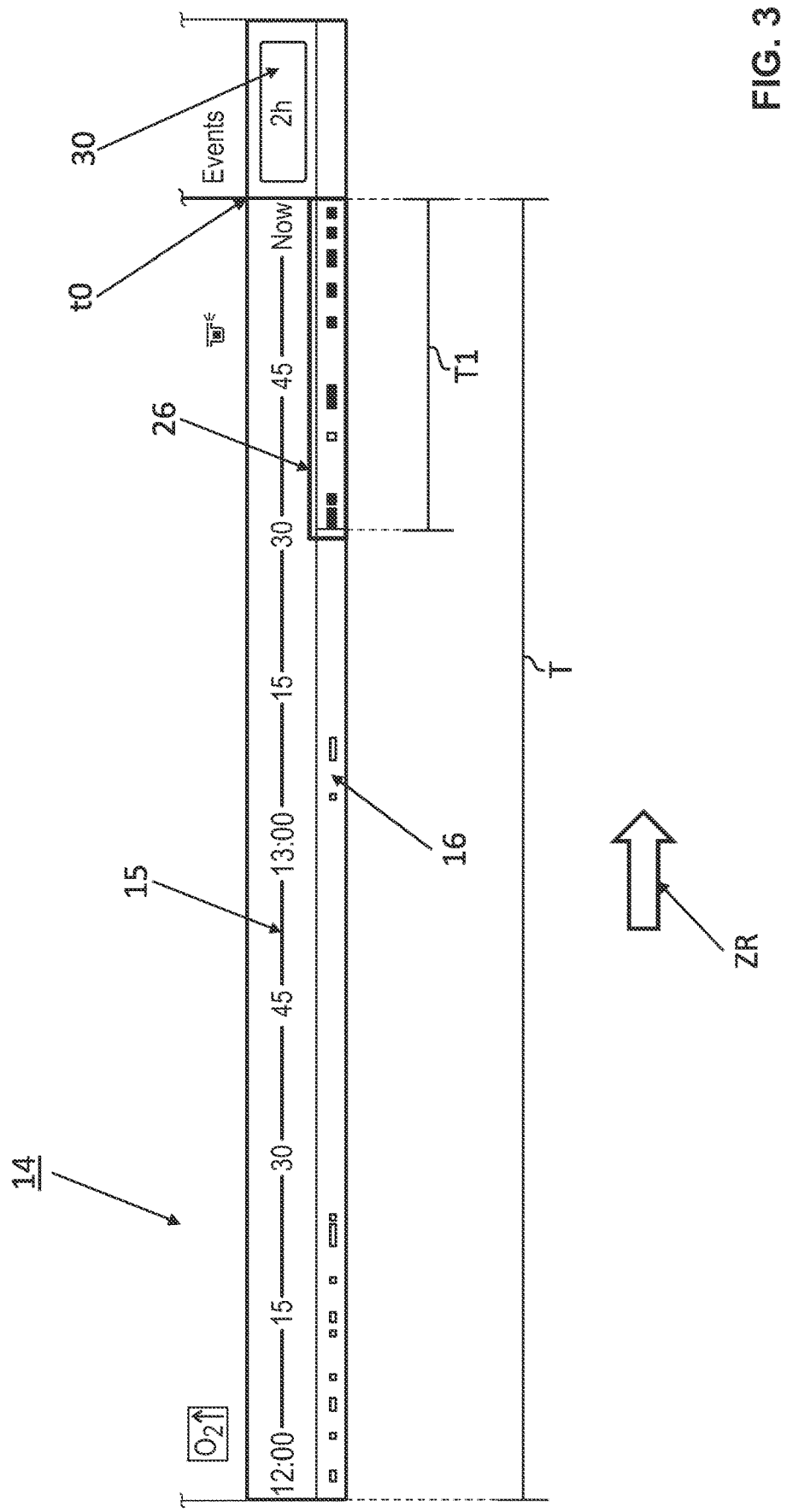
FIG. 3 is a display view showing the alarm overview display in the lower area of the display screen in an enlarged form prior to the selection of an alarm.

FIG. 3 shows the alarm overview display 14 of FIG. 2 in an enlarged form. It shows
- the overall alarm sequence 16, which covers the overall time period T,
- the alarm reference section 26, which covers the reference time window T1, wherein a rectangular frame shown in black is placed around the alarm reference section 26 for illustration,
- how the alarm reference section 26 is arranged in time in the overall alarm sequence 16 and hence how the reference time window T1 is arranged in the overall time period T, i.e., the positioning display of the exemplary embodiment,
- the reference time axis 15, which refers to the reference time window T1 and which is used for the alarm reference section 26 but not for the overall alarm sequence 16,
- the time period window 30, which shows the time period of the reference time window T1, and
- the reference time t0 on the reference time axis 15.

Furthermore, the time axis display direction ZR is shown in FIG. 3. The reference time axis 15, the overall alarm sequence 16 and the alarm reference section 26 extend in this time axis display direction ZR. The time axis display direction ZR points from older towards more recent times. The x axis of the signal curves, which are displayed in the signal curve area 10, is parallel to this time axis display direction ZR. The time axis display direction ZR points to the right in the example being shown; another orientation is possible as well.

Figure 4:
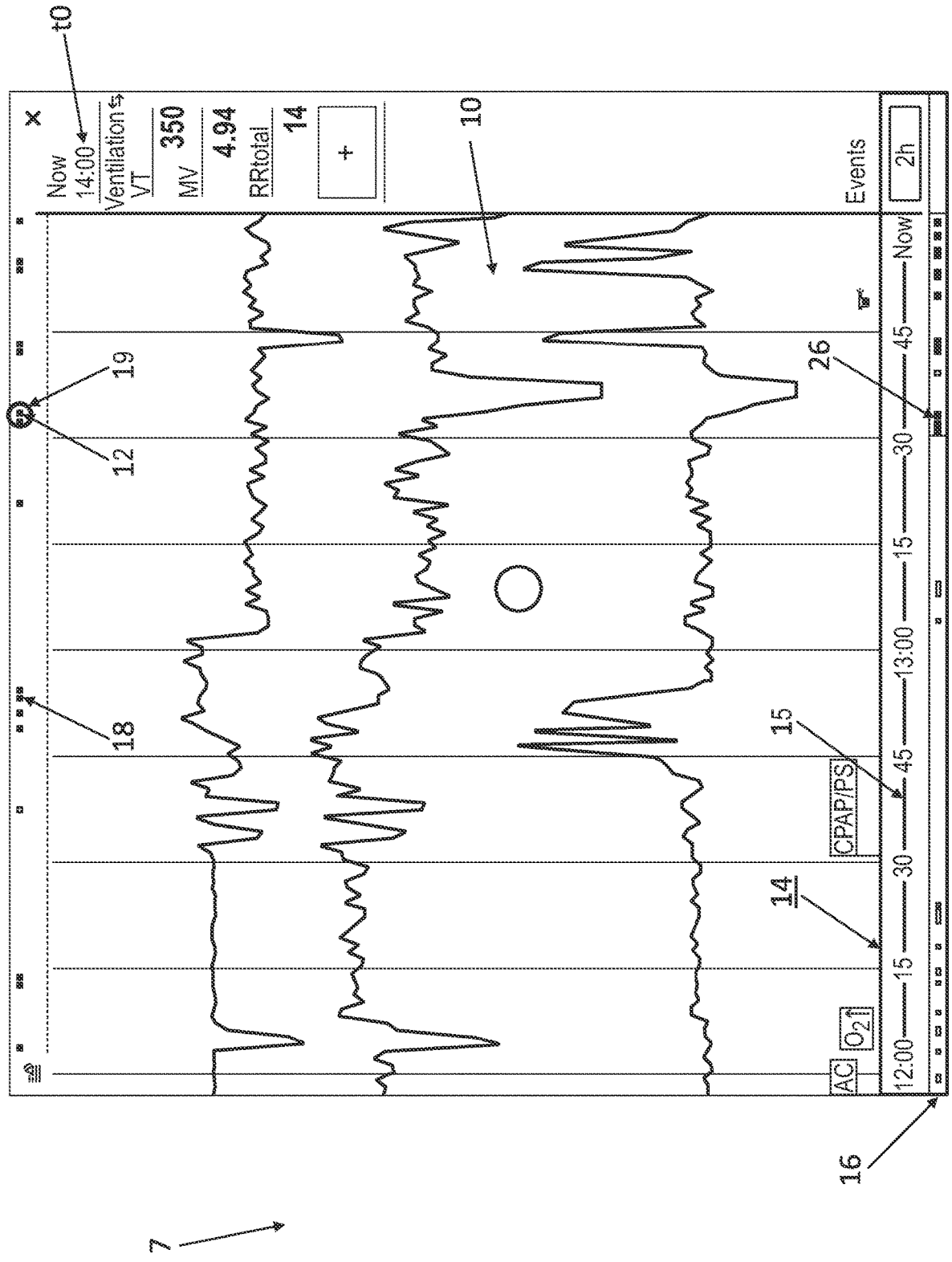
FIG. 4 is a display view showing a response to the selection of an alarm located in the reference time window.

A user selects a displayed alarm 12. The user can do this in different manners. One possibility is shown in FIG. 4: The user selects an alarm 12, which is displayed in the alarm reference sequence 18, for example, by touching the display for this alarm 12 with a finger. The circle 19 illustrates in FIG. 4 and in the figures following it the respective selection and interaction by a user. Further possibilities of how a user can select a displayed alarm 12 will be shown below.

The selection of the alarm 12 in the alarm reference sequence 18 is illustrated by FIG. 4. This selected alarm 12 belongs to the alarm type "MV low."

Figure 5:
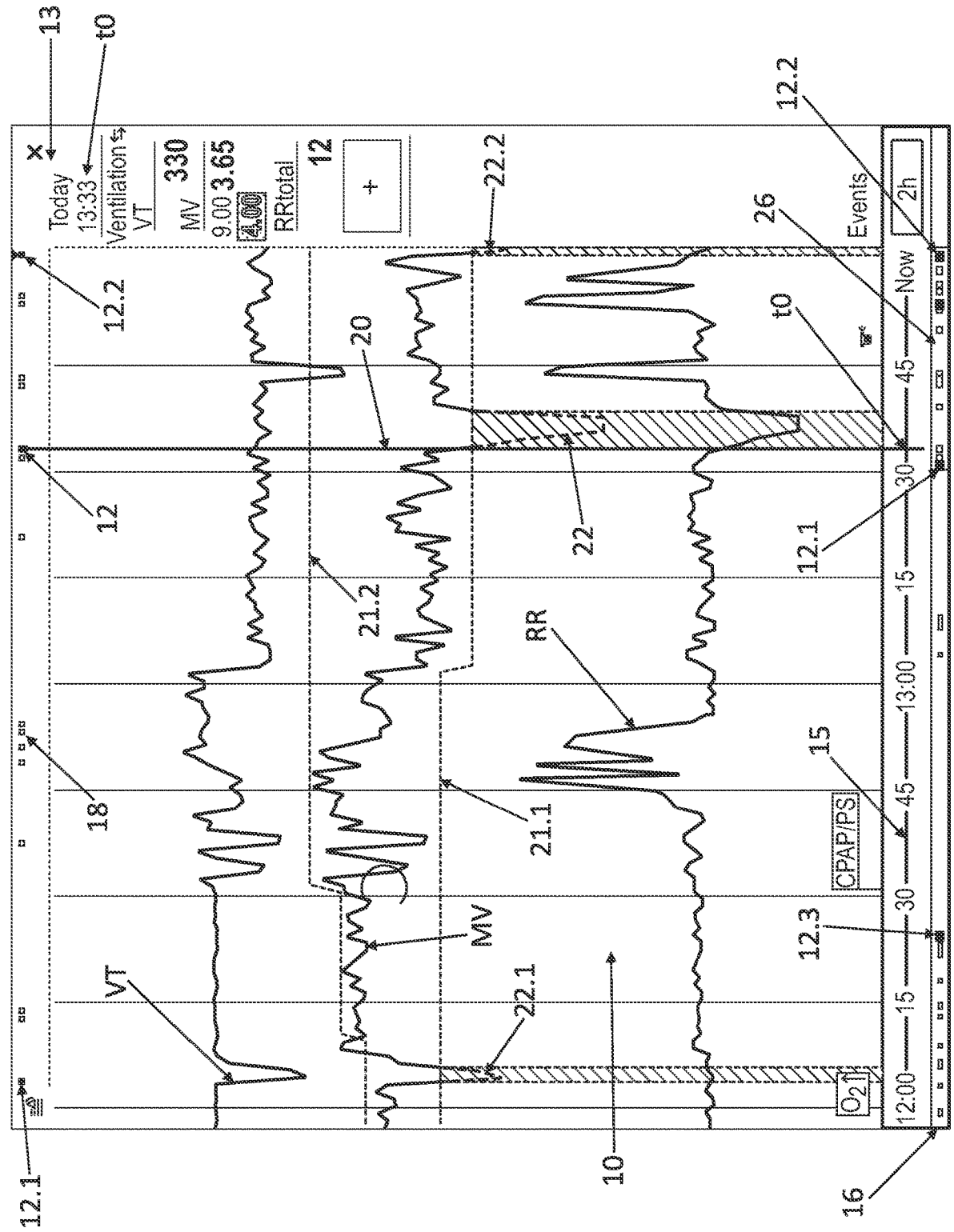
FIG. 5 is a display view showing an alarm reference sequence and a response to this selection.

FIG. 5 shows which responses are triggered by this selection of the alarm 12:
- The reference time line 20 jumps to the time 01:33 pm of the selected alarm 12. This time is now the reference time t0.
- The time of the selected alarm 12 (the new reference time t0, i.e., 01:33 pm) as well as the respective signal values of the three signals MV, VT and RR at this time t0 (330 mL, 3.65 L/minute and 12/minute) are displayed in the signal value area 13.
- A sequence each of the alarms detected in the reference time window T1 is displayed in the alarm reference sequence 18 as well as in the alarm reference section 26 of the overall alarm sequence 16. In response to the selection of the alarm 12, the additional alarms, which belong to the same alarm type as the selected alarm 12 are displayed in a highlighted form—highlighted compared to the other displayed alarms. The alarm 12.1 at the time 12:03 pm as well as the alarm 12.2 at the time 01:59 pm belong in this example to the same alarm type "MV low" as the selected alarm 12. For example, all the alarms that do not belong to the same alarm type "MV low" are displayed in FIG. 5 as an example in black and the others in white with a black border.
- The alarms 12, 12.1, 12.2 of the alarm type "MV low," which were detected in the reference time window T1, are, in addition, displayed in the overall alarm sequence 16, along with an additional alarm 12.3, which was detected outside the reference time window T1.
- A desired range for the signal MV is predefined or is calculated during the operating time by the signal processing unit 5. The lower limit 21.1 and the upper limit 21.2 of this desired range are displayed. As can be seen, the lower limit 21.1 and/or the upper limit 21.2 may be variable over time.
- The sections of the signal MV which are below the lower limit 21.1 and therefore lead to an alarm of the alarm type "MV low" are marked by highlighting. In the example shown, these are the section 22 for the alarm 12, the section 22.1 for the alarm 12.1 and the section 22.2 for the alarm 12.2. For example, the three sections 22, 22.1 and 22.2 are displayed with highlighting by a different background color in the signal curve area 10. It is always shown how long the state deviating from the desired state has lasted. The time of the selected alarm 12 and hence the selected reference time t0 represent in the example shown the first time of the section 22 at which the signal MV drops below the lower limit 21.1.

Figure 6:
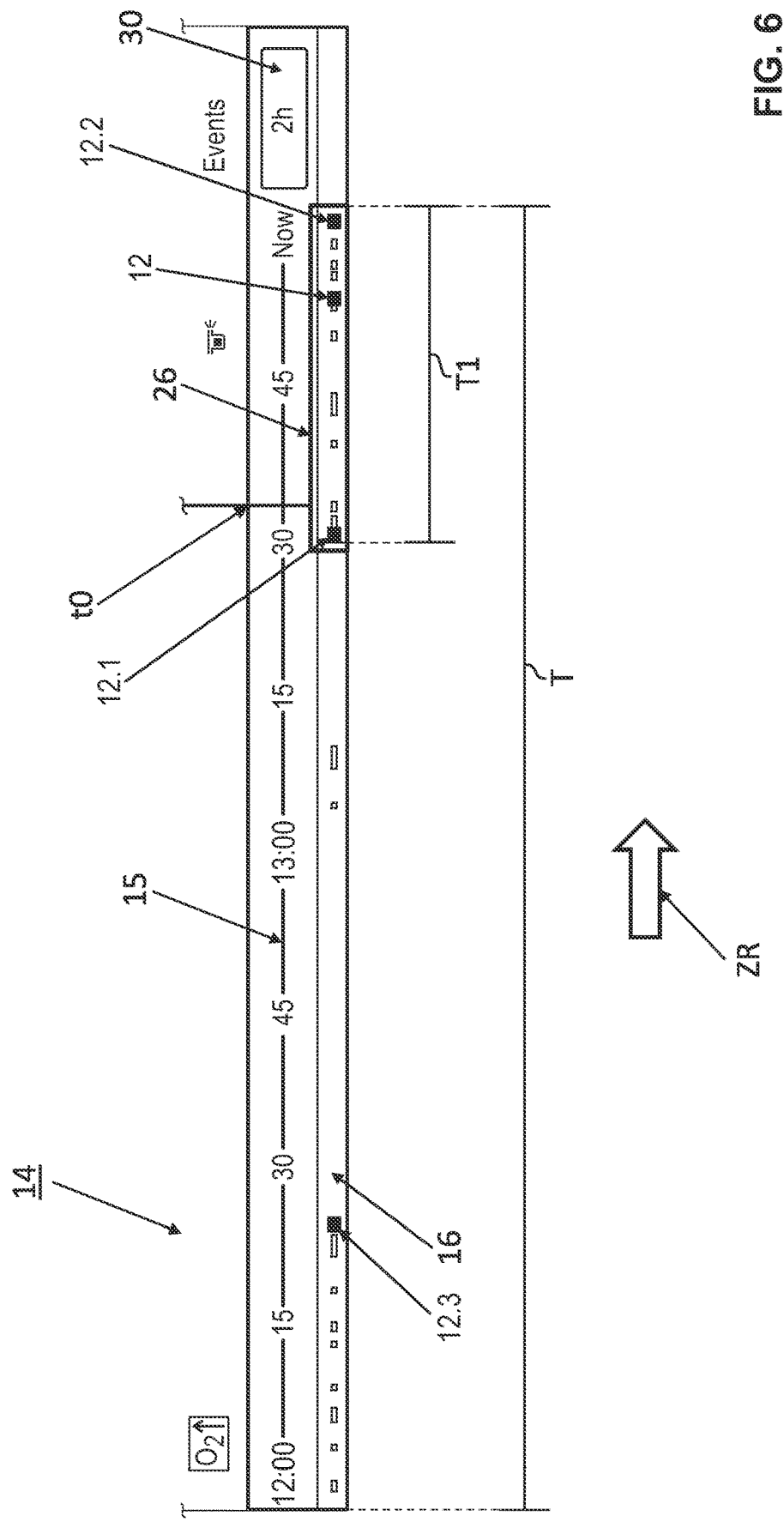
FIG. 6 is a display view showing the alarm overview display of FIG. 3 after selection of an alarm.

In a detail view of FIG. 5, FIG. 6 shows how the alarm overview display 14 from FIG. 3 changes after the alarm 12 was selected. Only the alarms 12.1, 12.2 and 12.3 of the alarm type "MV low" are displayed with highlighting in the overall alarm sequence 16 and hence also in the alarm reference section 26 and the others are not highlighted (here: in white with a black frame. This embodiment makes it possible to display all alarms of the alarm type "MV low" with highlighting, without using a special symbol for the alarm type "MV low," doing so by only the alarms "MV low" being highlighted. It can be seen where the selected alarm 12 is located in the alarm reference section 26. The alarm overview display 14 also shows where the selected alarm 12 is located in time in the overall time period T. Furthermore, the alarm 12.3, which is located outside the reference time window T1, can be seen.

Figure 7:
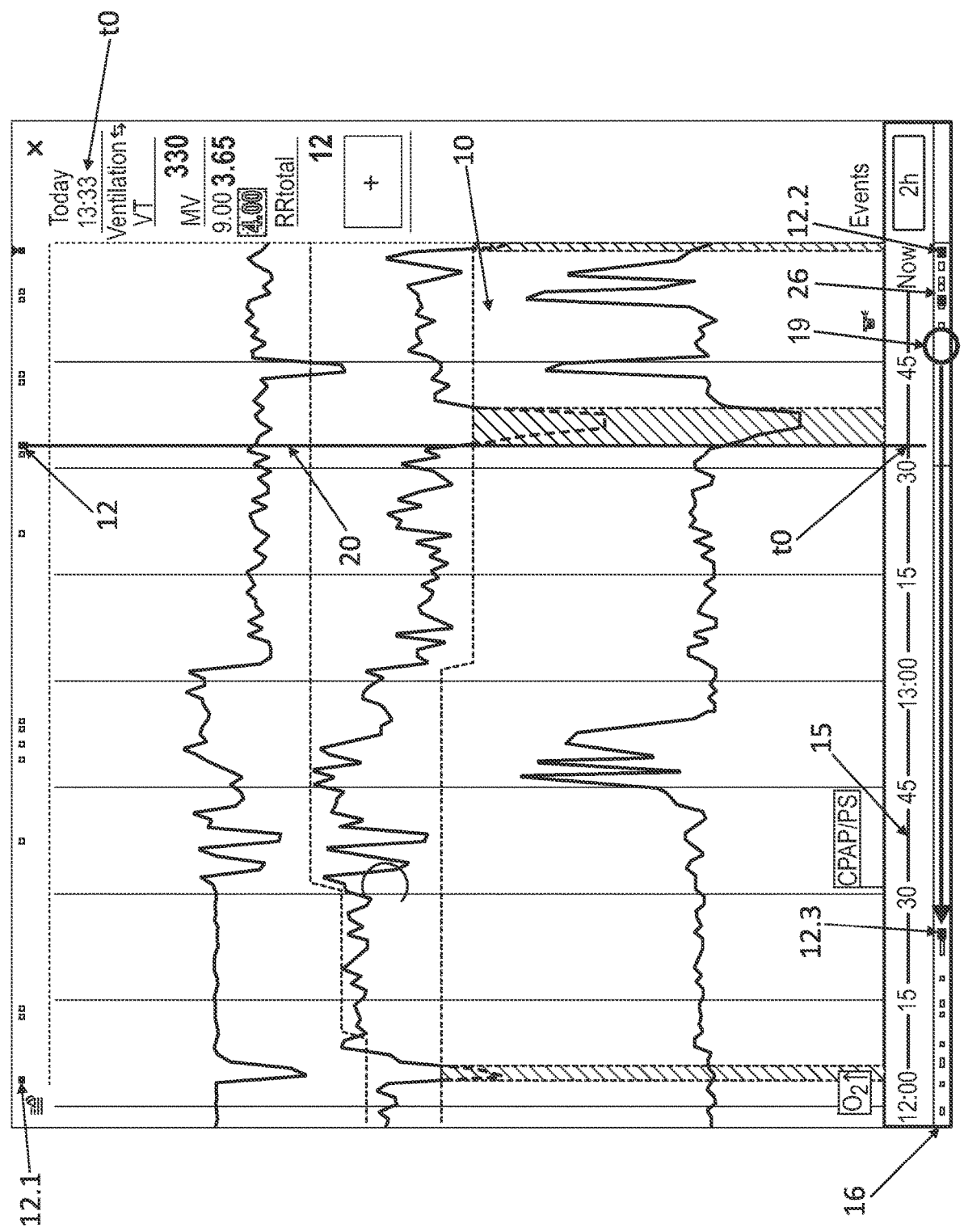
FIG. 7 is a display view showing aspects of how the reference time window is shifted and an alarm before the reference time window is selected.
Figure 8:
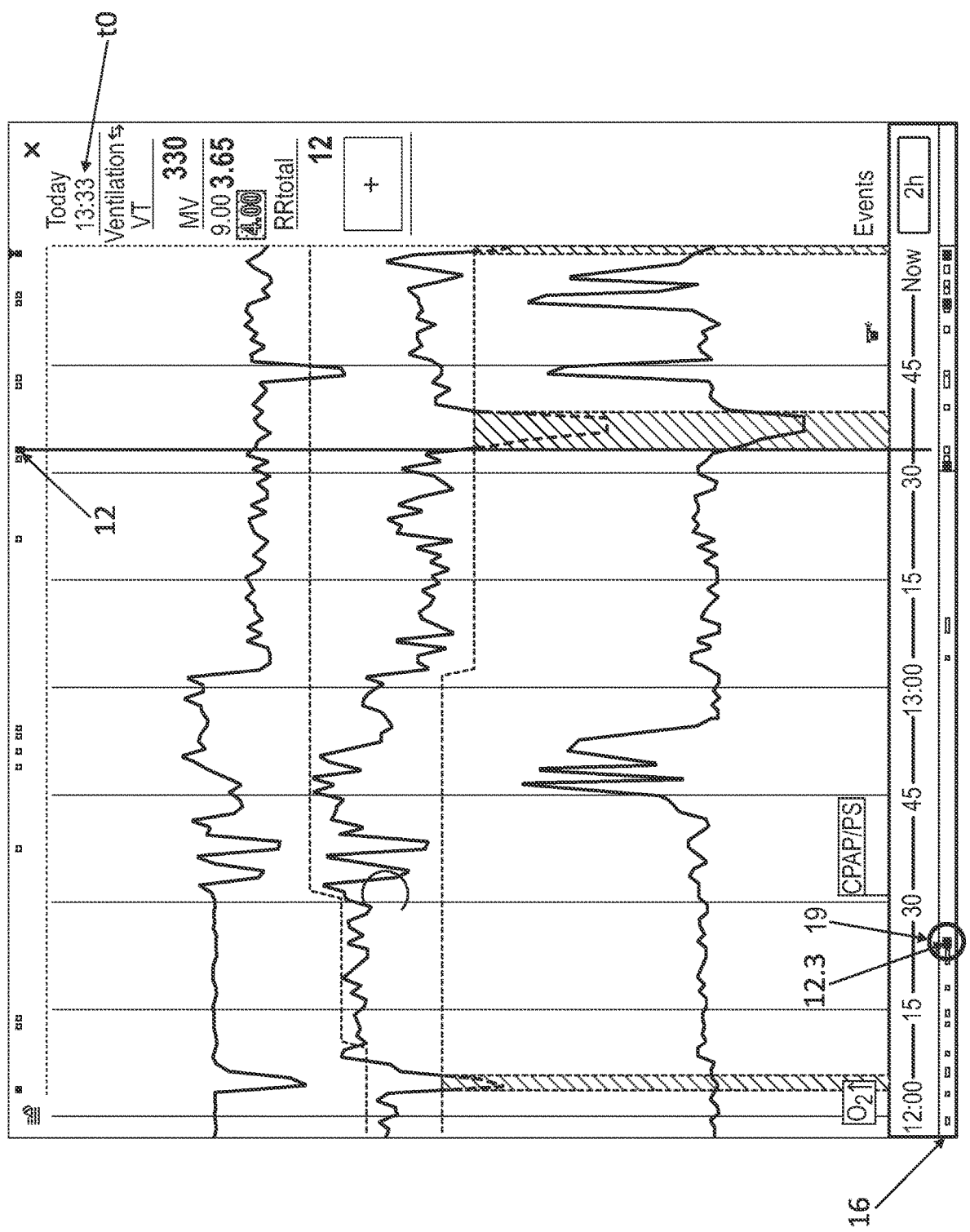
FIG. 8 is a display view showing further aspects of how the reference time window is shifted and an alarm before the reference time window is selected.

FIG. 7 and FIG. 8 show how the user predefines a chronologically earlier reference time window T1 and selects an alarm of the same type in the earlier time window T1. The overall time period T remains unchanged. The predefined earlier reference time window T1 shall comprise the time at which the alarm 12.3 of the same type was detected. The user touches the alarm reference section 26 and pulls it to the left over the time of the alarm 12.3, cf. circle 19 and the arrow pointing to the left in FIG. 7. The user selects the alarm 12.3, for example, by touching the display in the overall alarm sequence 16 with a finger, cf. FIG. 8.

Figure 9:
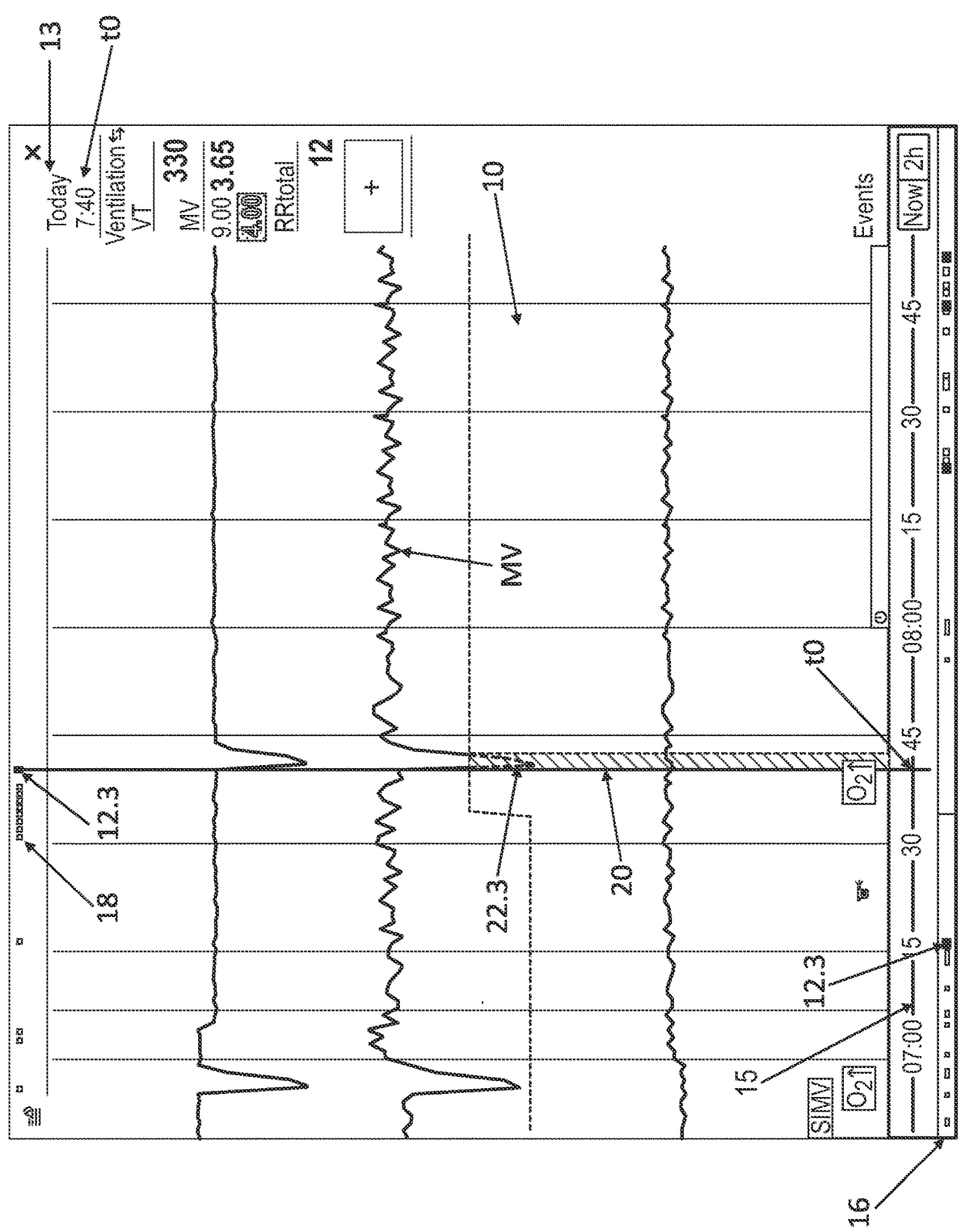
FIG. 9 is a display view showing further aspects of how the reference time window is shifted and an alarm before the reference time window is selected.

The response to this user input is shown in FIG. 9:
- The reference time t0 is now the time at which the alarm 12.3 occurred, namely, 07:40 am.
- Section 22.3 of the signal MV, which has led to the alarm 12.3, is displayed with highlighting.
- The reference time line 20 shows now as the reference time t0 the time of the alarm 12.3, i.e., 07:40 am.
- The new reference time t0 and the values of the three signals VT, MV and RR at this reference time t0 are displayed in the signal value area 13.
- The earlier reference time window T1 is displayed on the reference time axis 15.
- The signal curve area 10 shows now the three signal curves VT, MV and RR in the earlier reference time window T1.
- The overall alarm sequence 16 remains unchanged.

Figure 10:
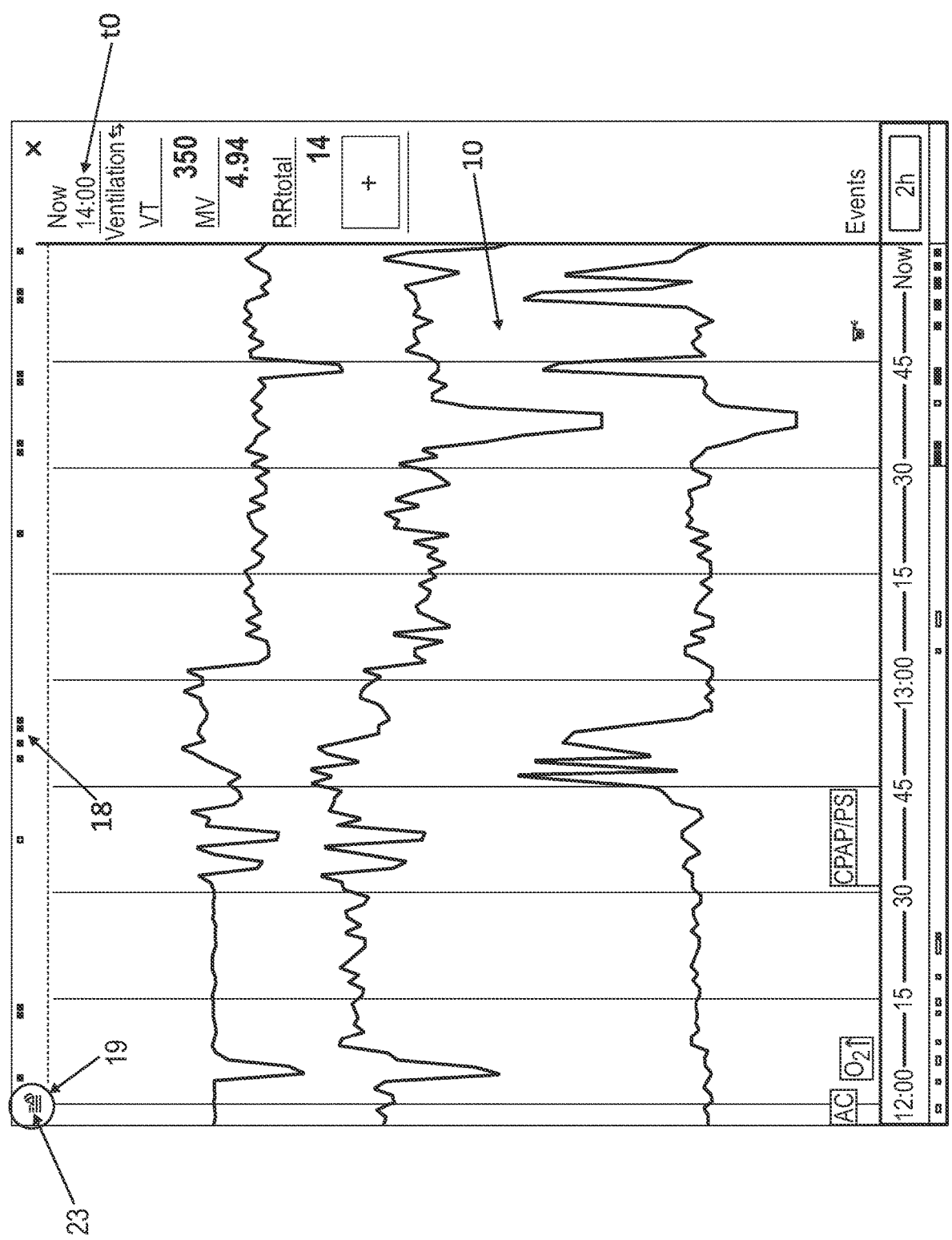
FIG. 10 is a display view showing how the alarm descriptions are faded in or superimposed.

In the examples shown so far, the user has selected an alarm by selecting a symbol for the alarm type and the arrangement in time in the overall alarm sequence 16 or in the alarm reference section 26. Another manner of selecting an alarm will be shown below. The starting point is again the initial situation, which is shown in FIG. 2. The user clicks on the symbol 23 or performs a corresponding user input in another manner. This is suggested in FIG. 10 by the circle 19 around the symbol 23.

Figure 11:
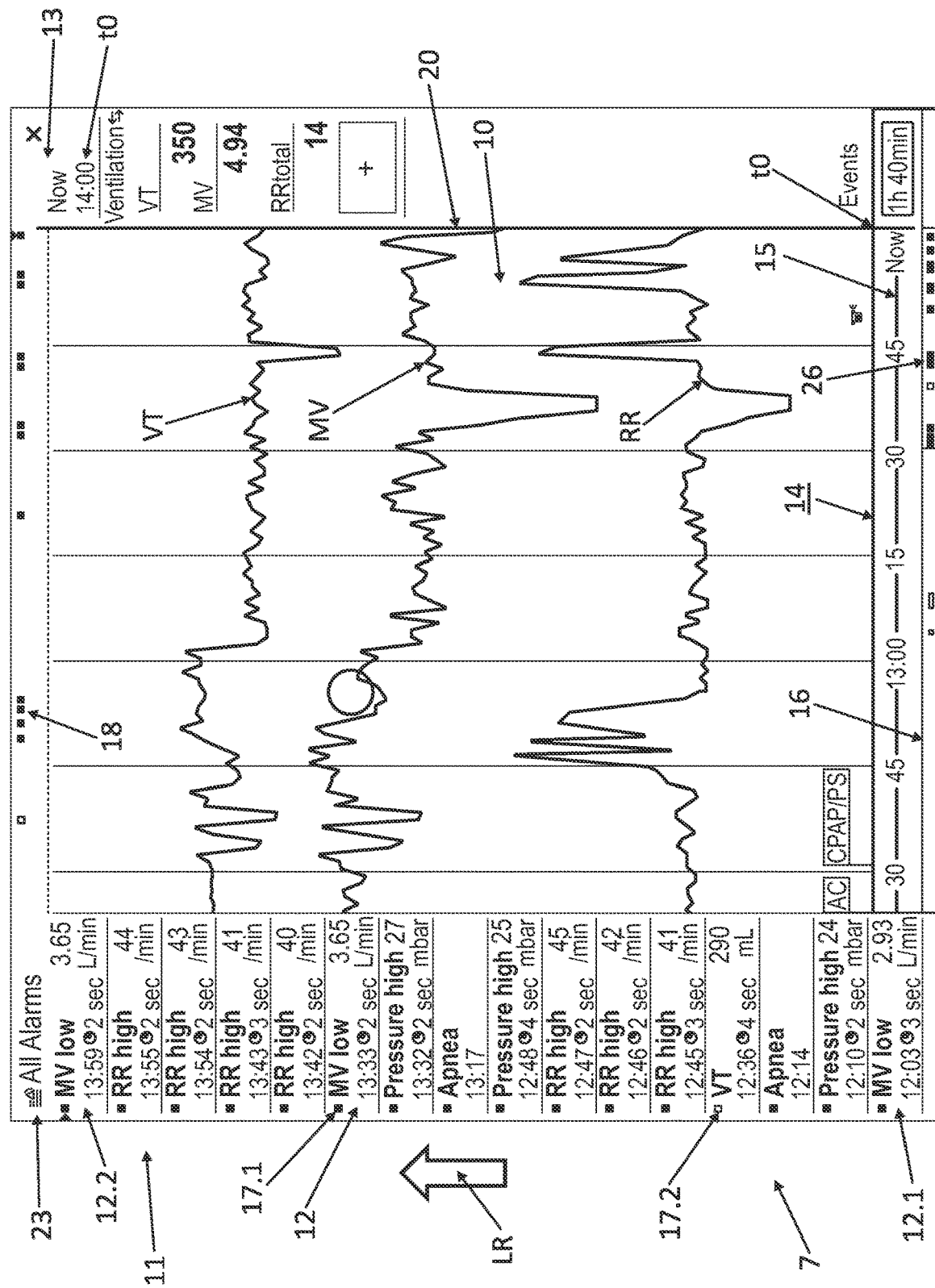
FIG. 11 is a display view showing how the alarm descriptions are faded in or superimposed.

As is shown in FIG. 11, an alarm description sequence 11 is additionally displayed as a response to this, doing so on the left next to the signal curve area 10. In the example shown, this alarm description sequence 11 shows textual descriptions of a sequence of at most N alarms following one another directly over time, the number N preferably depending on the vertical dimension of the display screen 7 and on the preferably variable font size. The alarm description sequence 11 shows these N alarm descriptions in an order from top to bottom, the alarm description of the alarm of the sequence that is the most recent one in time being shown at the top. Each alarm description occupies the same vertical space in the alarm description sequence 11, assuming that the alarm descriptions are displayed in a horizontal writing direction SR.

The alarm description sequence 11 is a list of textual alarm descriptions, which is ordered chronologically, this list referring to a sequence of at most N alarms, and these alarms having been detected during the overall time period T. In the example shown, some alarms were detected in the reference time window T1, for example, the alarm 12 at the time 01:33 pm and the alarm 12.2 at the time 01:59 pm.

The list extends in the list direction LR. This list direction LR is preferably at right angles to the time axis display direction ZR. In the example being shown, the list direction LR is vertical. The more recent an alarm is, the farther up is its alarm description in this ordered list 11. The writing direction SR of an individual alarm description is at right angles to the list direction LR and hence—in case of a two-dimensional display—parallel to the time axis display direction ZR. A perspective, i.e., two-dimensional display is possible as well.

One consequence of the step of displaying the alarm description sequence 11 is that the reference time window T1 is shortened in terms of time in the exemplary embodiment. The time scale and hence the scale of the display remain unchanged, but less space is available for the reference time window T1. The finer time scale remains unchanged. After the alarm description sequence 11 has been displayed, the shortened reference time window T1 extends from 12:20 pm to 02:00 pm, i.e., it is shorter by about 20 minutes. The portion that the alarm reference section 26 occupies in the overall alarm sequence 16 becomes correspondingly shorter. The positioning display is consequently changed automatically.

The alarms that are displayed in the alarm description sequence 11 were detected in the original reference time window T1, which lasts from 12:00 pm to 02:00 pm. It is possible in one embodiment that an alarm displayed in the alarm description sequence 11, for example, the alarm 12.1 at the time 12:03 pm, is not located any longer in the shortened reference time window T1, which lasts from 12:20 pm to 02:00 pm.

The above-described embodiment is meaningful if the textual descriptions are displayed in a language that provides for a horizontal writing direction, for example, from left to right in case of English or German or from right to left in Hebrew or in Arabic. If the textual descriptions are displayed in a language with a vertical writing direction, for example, traditional Chinese or Japanese, the display is preferably adapted correspondingly. For example, the time axis display direction ZR and the writing direction SR of a textual alarm description extend vertically and the list direction LR is horizontal. The configuration can preferably be selected according to the language in which text outputs are to be generated and the writing direction and hence the time axis display direction ZR and the list direction LR are set thereby.

It is also possible to display on the display screen a perspective display, wherein the time axis display direction ZR, the list direction LR and the writing direction SR define a three-dimensional Cartesian system of coordinates, which is displayed in a perspective form.

The alarm description sequence 11 extends in the list direction LR in the example being shown, and an alarm description of an alarm of the sequence is displayed the farther up the more recent the alarm is.

The following pieces of information are displayed for each displayed alarm:
  a textual description of the alarm type, e.g., "MV low" or "RR high,"
  the symbol for the relevance of this alarm type,
  the respective time of the alarm—more precisely, the first time at which this alarm occurred,
  optionally the respective duration of the alarm, preferably in [sec] and
  optionally the respective value or the maximum value of the signal in question, which value deviates from a desired range, at the time or during the time period of the alarm.

A plurality of alarms of the same alarm type may occur in the time range shown; an alarm of the type "MV low" three times and an alarm of the type "RR high" seven times in the example shown in FIG. 11.

Figure 12:
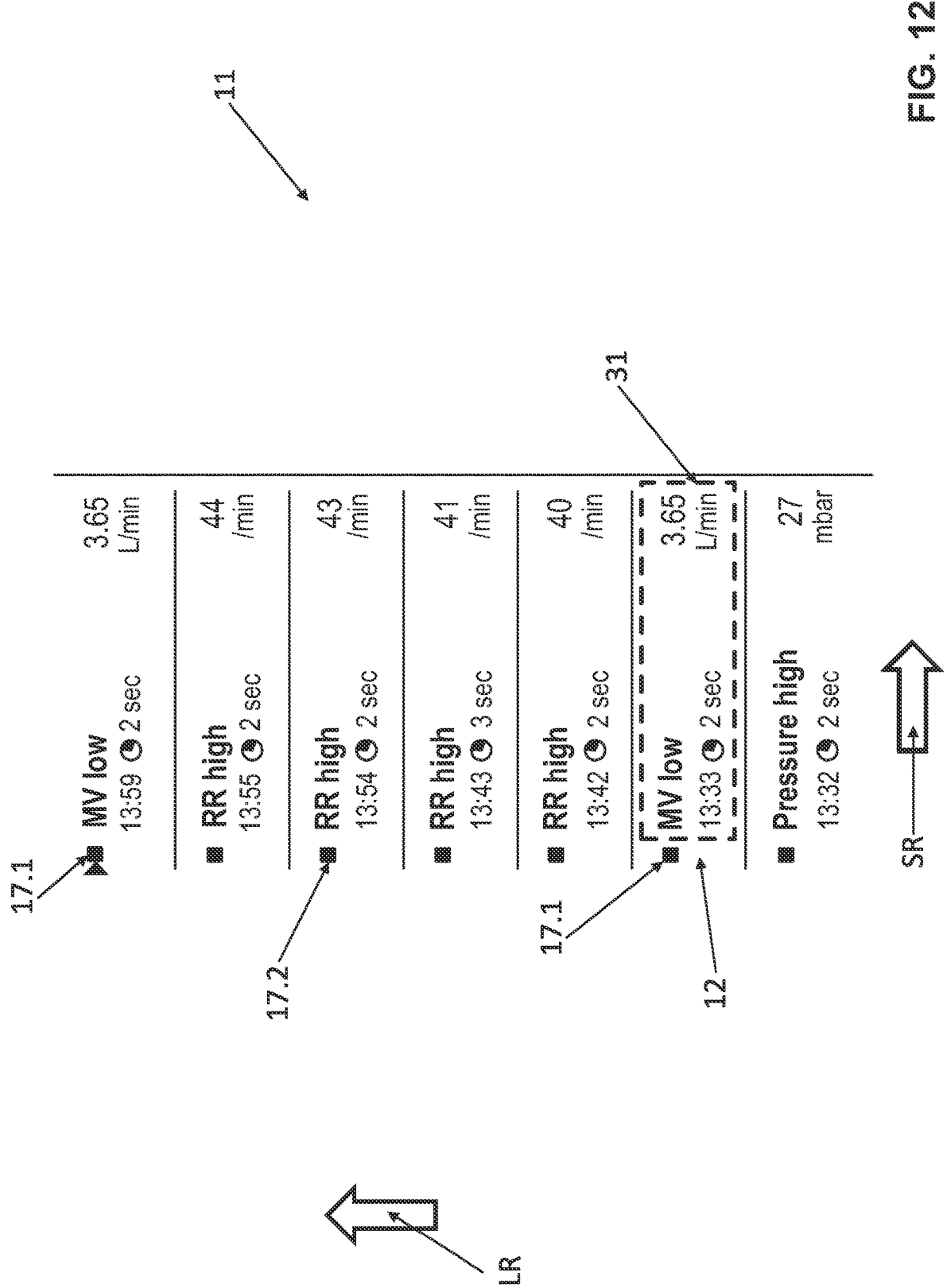
FIG. 12 is a display view showing a plurality of alarm descriptions in an enlarged display.

FIG. 12 shows a plurality of alarm descriptions in an enlarged display. The exemplary alarm description 31 for the alarm 12 comprises the following pieces of information:
  the textual description "MV low" of the alarm type "MV low" of alarm 12,
  the time 01:33 pm,
  the duration 2 sec,
  the signal value of 3.65 L/minute at the time of the alarm 12, and
  the symbol 17.1 for the relevance "high" of the alarm type "MV low."

Furthermore, the list direction LR of the alarm description sequence 11 as well as the writing direction SR of the textual alarm description are shown in FIG. 12. The writing direction SR is at right angles to the list direction LR.

Figure 13:
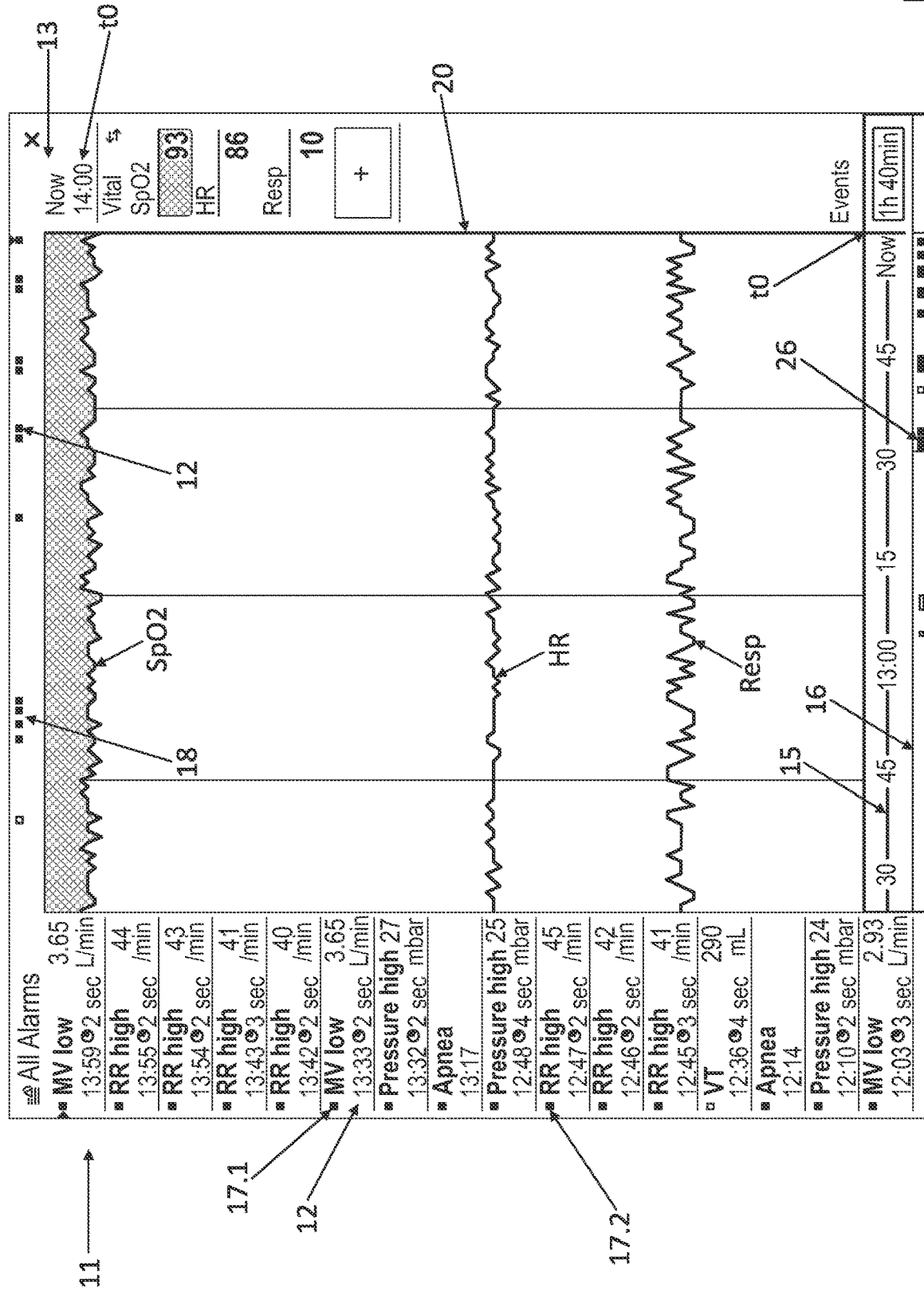
FIG. 13 is a display view showing how an alarm is selected when the time curve of the signal to which the alarm refers is not displayed.

FIG. 13 shows another starting point for the selection of an alarm of the alarm type "MV low." Curves of the three signals SpO2, HR and Resp are shown in the signal curve area 10, but the curve of the signal MV is not. The user can select the alarm 12 in the alarm reference sequence 18 or proceed as described below.

Figure 14:
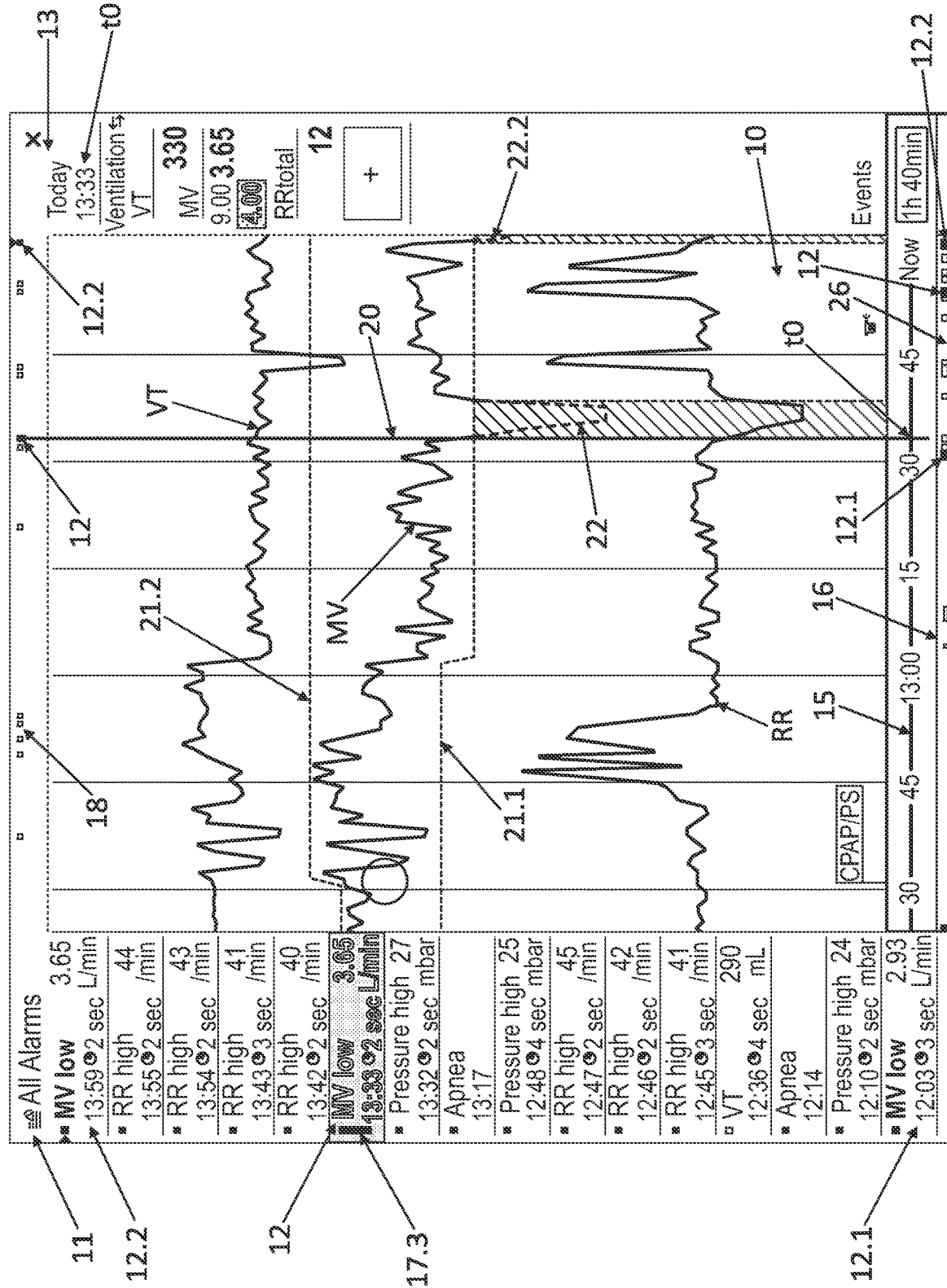
FIG. 14 is a display view showing a response to the selection of an alarm located in the reference time window in the alarm description sequence.

The user selects a displayed alarm description, for example, that of the alarm 12, in the alarm description sequence 11. FIG. 14 shows as an example the responses the selection of the alarm 12 has:
  The curves of the signals VT, MV and RR are displayed in the signal curve area 10 in the reference time window T1.
  The reference time line 20 jumps to the time 01:33 pm of the selected alarm 12, and this time is used now as the reference time t0.

The time t0 of the selected alarm 12 (01:33 pm) as well as the signal values of the three signals MV, VT and RR at this reference time t0 (330 mL, 3.65 L/minute and 12/minute, respectively) are displayed in the signal value area 13.

All alarms 12, 12.1, 12.2 of the selected alarm type "MV low" are displayed with highlighting compared to the other alarms in the alarm description sequence 11, for example, by the other alarms being displayed with light-face lines and only the alarms 12, 12.1 and 12.2 continuing to be displayed in bold.

In the sequence of the alarms in the time window, which are displayed by the symbols for the respective alarm types in the alarm reference sequence 18, i.e., the alarms of the alarm type "MV low" here, the selected alarm is displayed with highlighting compared to the other alarms.

The selected alarm 12 is also marked by highlighting, for example, by a different background color, in the alarm description sequence 11 compared to the alarms 12.1, 12.2 of the same alarm type "MV low."

The alarm type "MV low," in this case the relevance for the alarm type, of the alarm 12 is displayed with a different symbol, for example, with a rectangle instead of with a circle.

The overall alarm sequence 16 remains unchanged.

Figure 15:
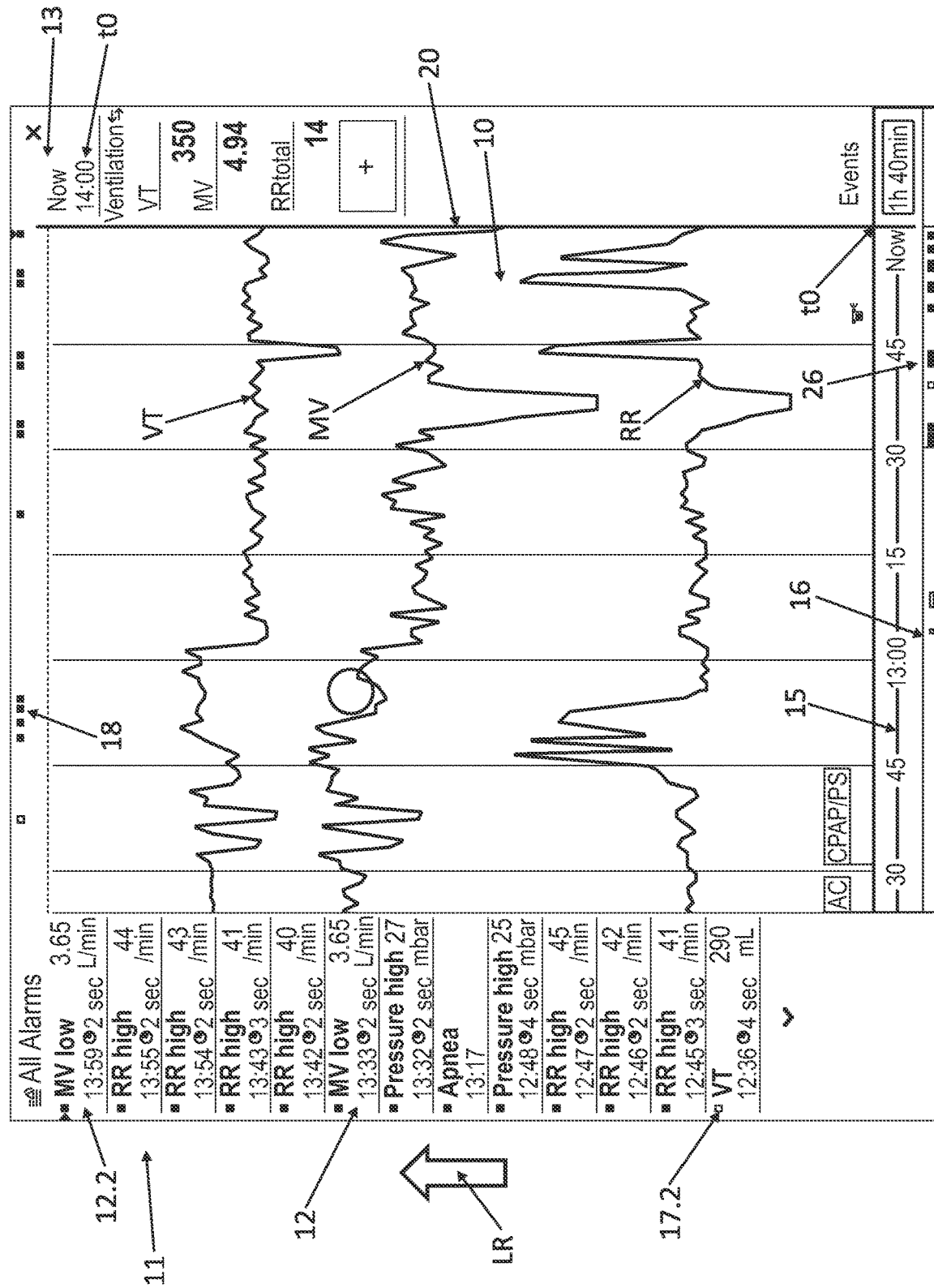
FIG. 15 is a display view showing a different embodiment of the alarm description sequence.
Figure 16:
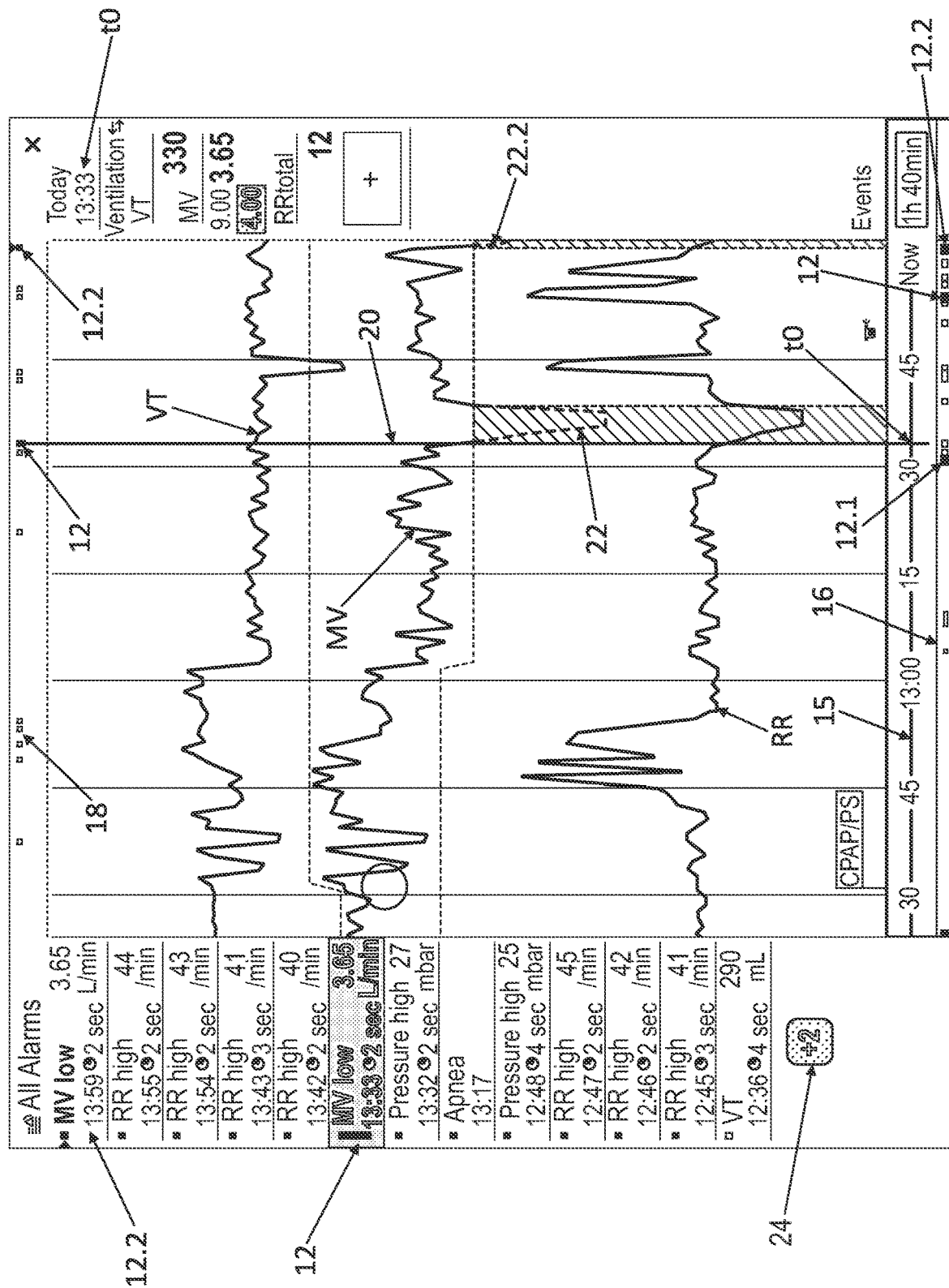
FIG. 16 is a display view showing the different embodiment of the alarm description sequence.
Figure 17:
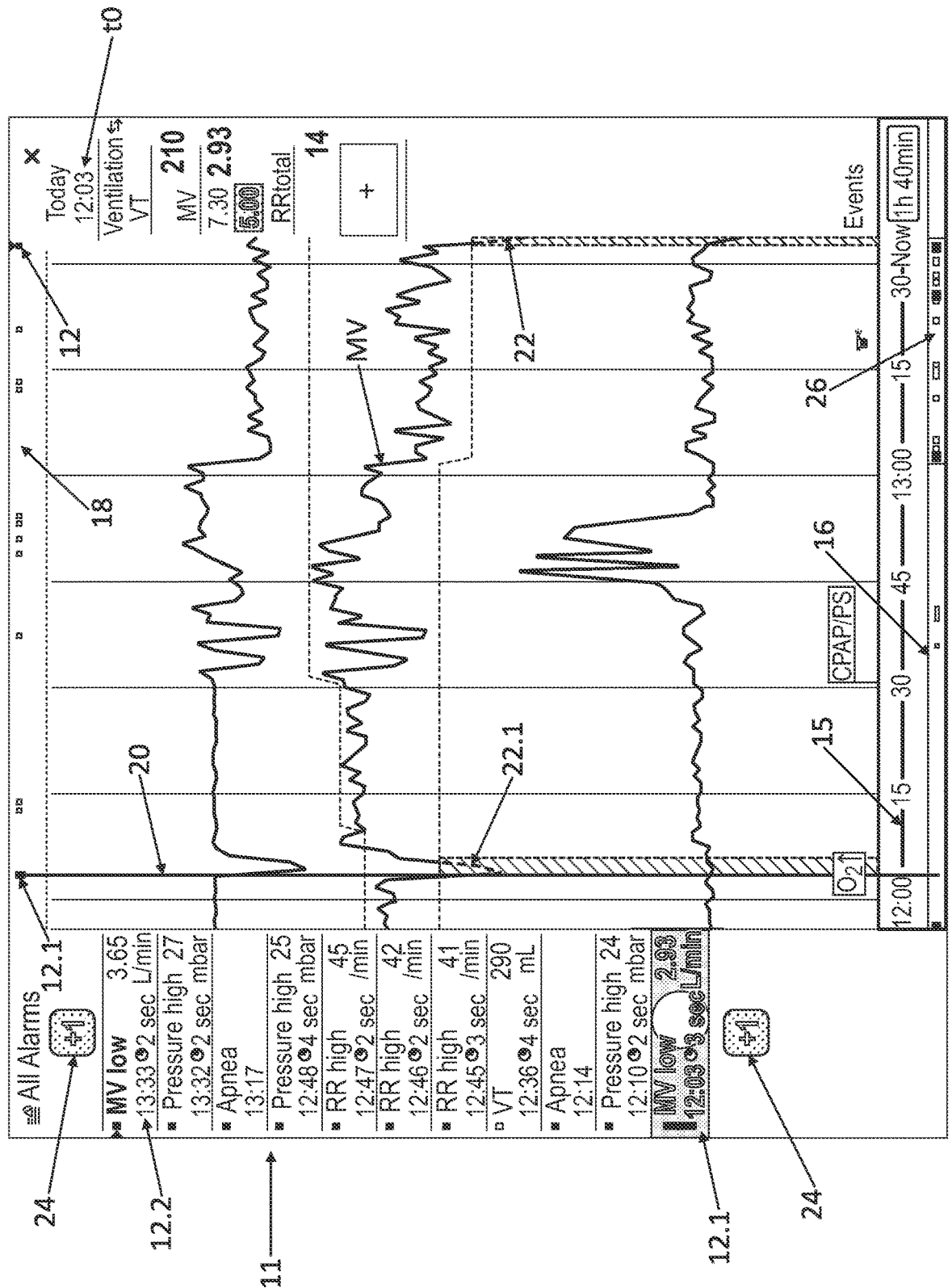
FIG. 17 is a display view showing the different embodiment of the alarm description sequence.

In the different embodiment shown in FIG. 15 through FIG. 17, the alarm description sequence 11 shows only alarms that are located in the shortened reference time window T1. FIG. 15 shows the situation before the selection of an alarm in the alarm description sequence 11. FIG. 16 shows the response after the user has selected the alarm 12.

A place 24 under the alarm description sequence 11 has remained free because the alarm description sequence 11 is correspondingly short. This place 24 shows the number of alarms in the overall time period T that are located before the reference time window T1 and which are therefore not displayed in the alarm description sequence 11 and are of the same alarm type as the selected alarm 12, in this case two alarms (+2), cf. FIG. 16.

The user may click on the display of this number, for example, with a finger. As a result, alarms earlier in time are displayed, see FIG. 17. The reference time window T1 changes, in this case to the time period from 11:50 am to 01:35 pm, which becomes visible in the reference time axis 15. The finer time scale remains unchanged. The reference time t0 is now 12:03 pm. The alarm reference sequence 18 is displayed in a correspondingly shifted manner. Furthermore, it is shown in two places 24 that an earlier alarm and a later alarm, which was detected in the overall time period T before and after the reference time window T1 and is of the same alarm type as the selected alarm 12 (+1), are not displayed in the changed alarm description sequence 11, cf. FIG. 17.

Figure 18:
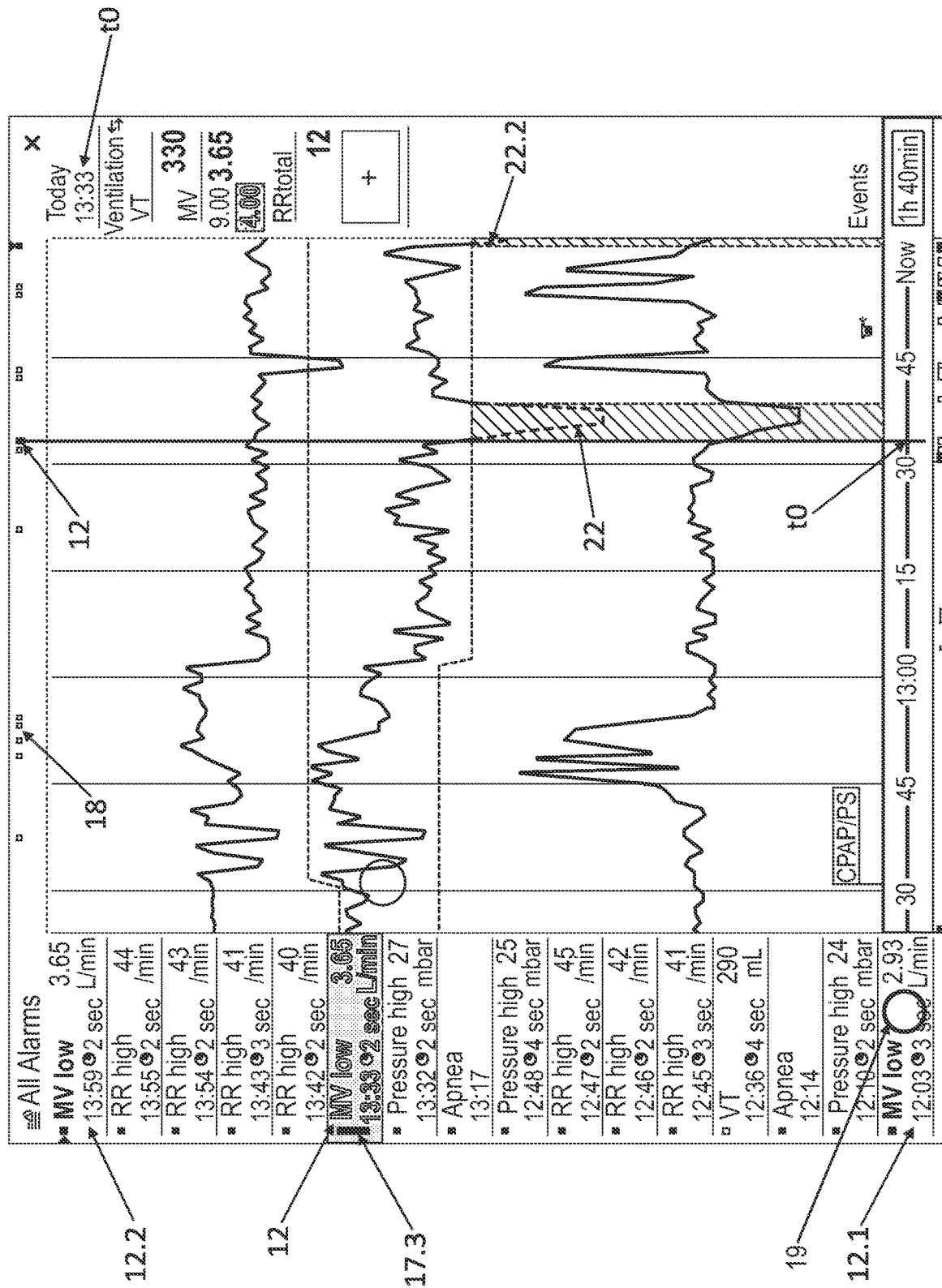
FIG. 18 is a display view showing a response to the selection of an alarm located before the reference time window in the alarm description sequence.
Figure 19:
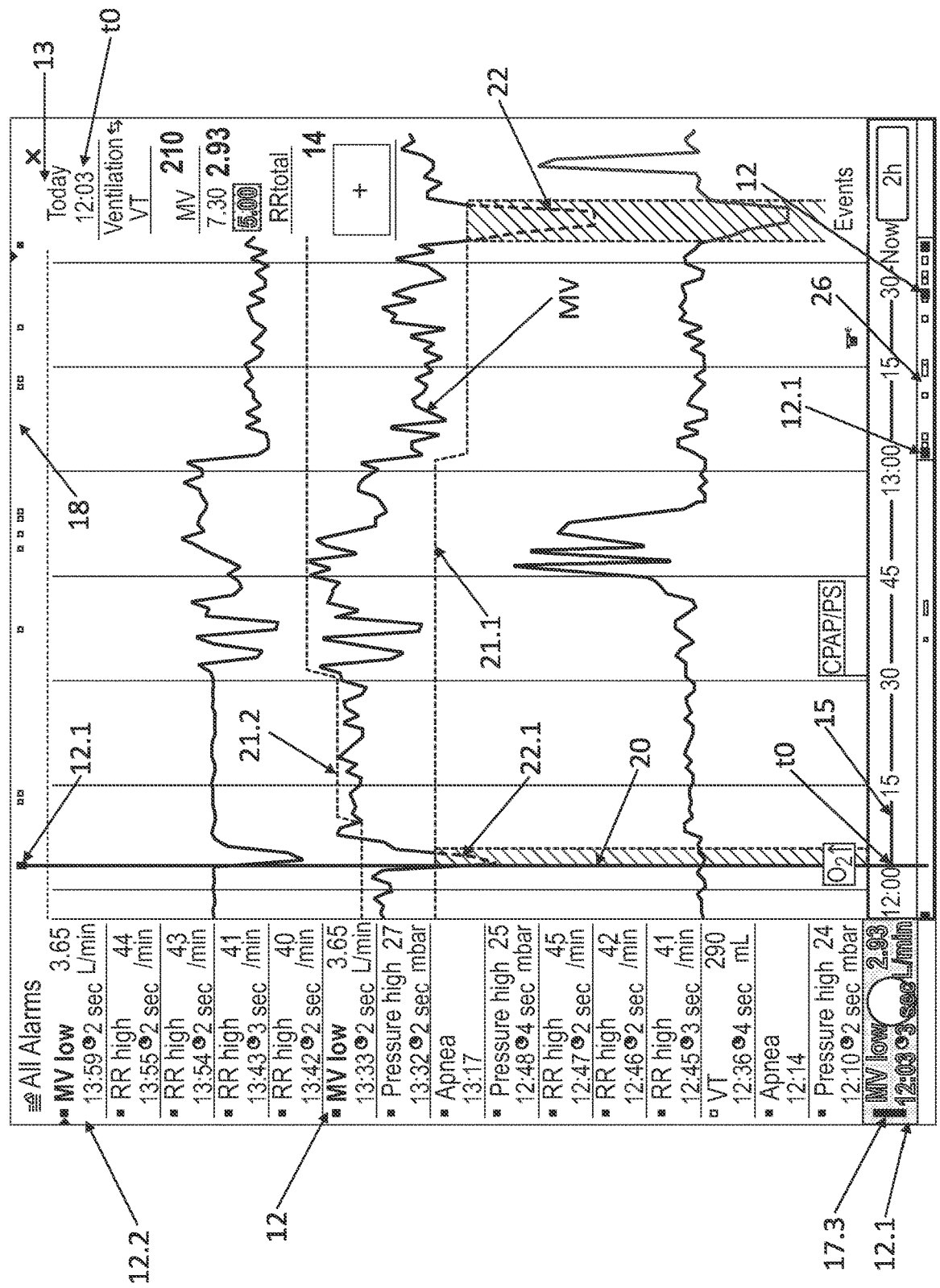
FIG. 19 is a display view showing a response to the selection of an alarm located before the reference time window in the alarm description sequence.

In the example according to FIG. 18, the user selects the alarm 12.1, which was detected at the time 12:03 pm. This alarm 12.1 is located outside the current reference time window T1. FIG. 19 shows the response to this selection:

Another time window T1, namely, the time period from 11:55 am to 01:35 pm, is shown on the reference time axis 15. The selected alarm 12.1 is located in this changed reference time window T1.

The displayed alarms in the alarm reference sequence 18 and in the alarm reference section 26 refer to this changed reference time window T1.

The reference time t0 is now the time 12:03 pm of the selected alarm 12.1. This reference time t0 as well as the signal values at this reference time t0 are displayed in the signal value area 13.

The reference time line 20 jumps to the changed reference time t0.

The selected alarm 12.1 is displayed with highlighting.

The overall time period T and the overall alarm sequence 16 remain unchanged.

Figure 20:
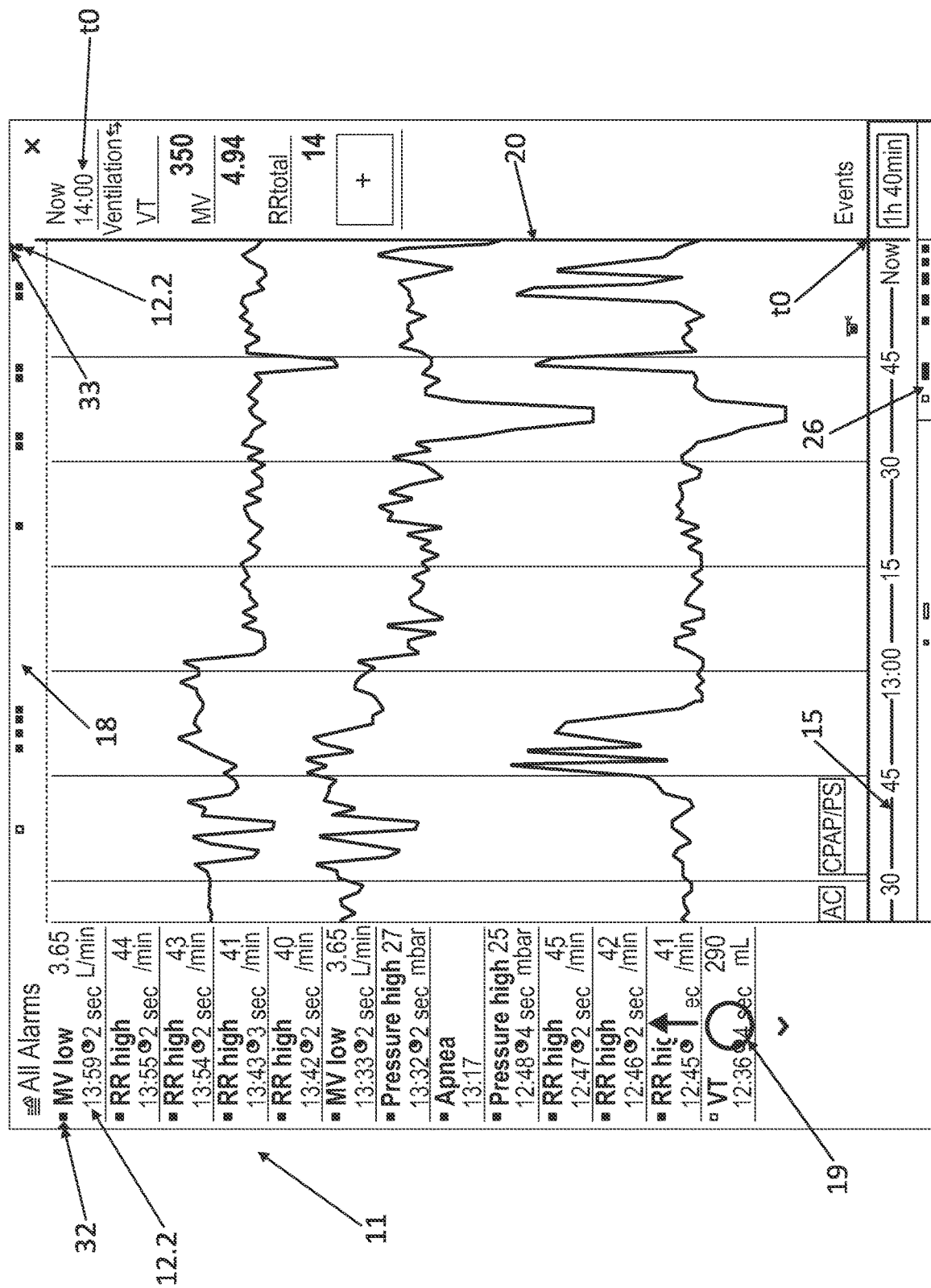
FIG. 20 is a display view showing a correlation indicator is used to display an alarm in the alarm reference sequence.
Figure 21:
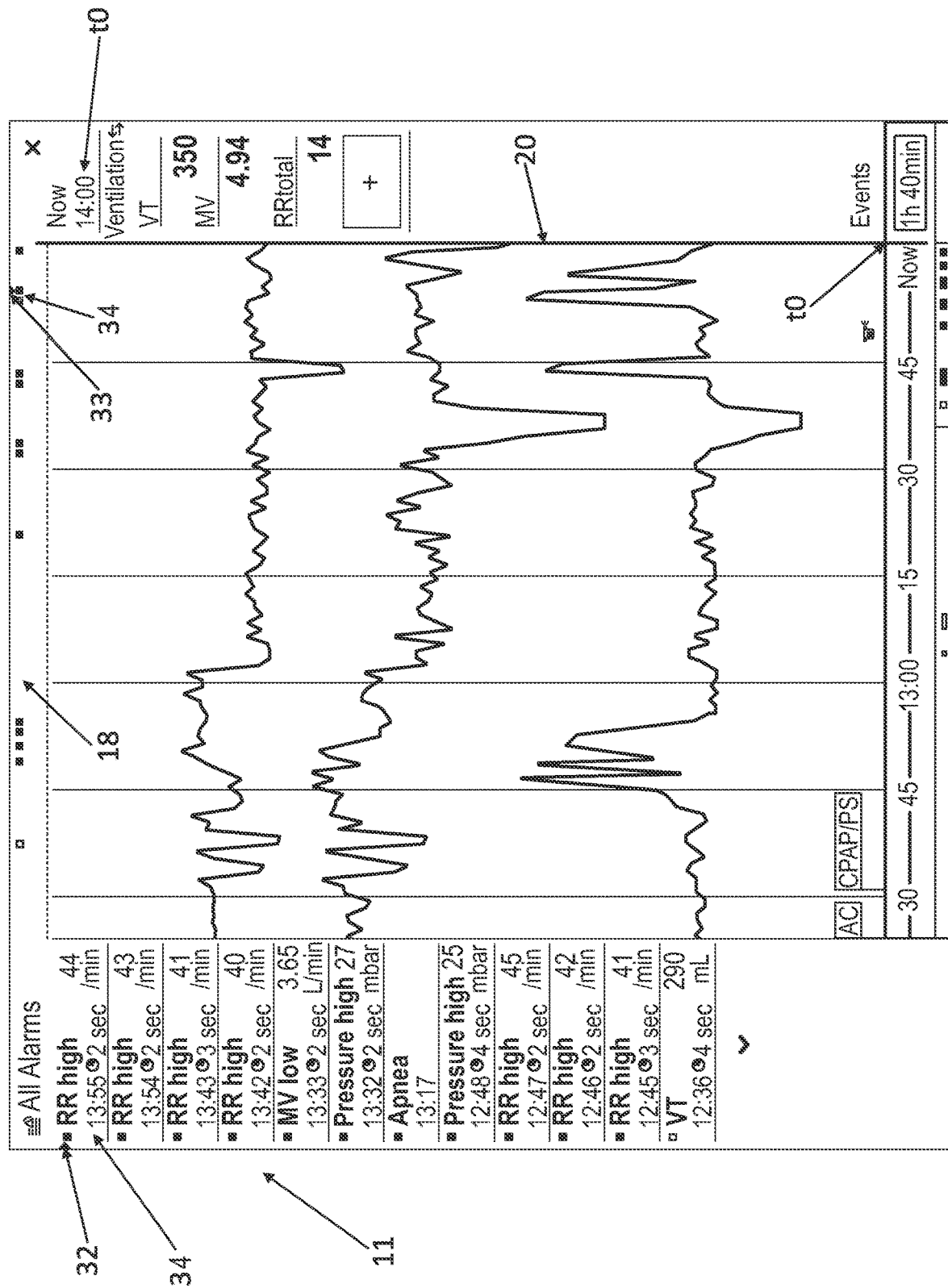
FIG. 21 is a display view showing a correlation indicator is used to display an alarm in the alarm reference sequence.
Figure 22:
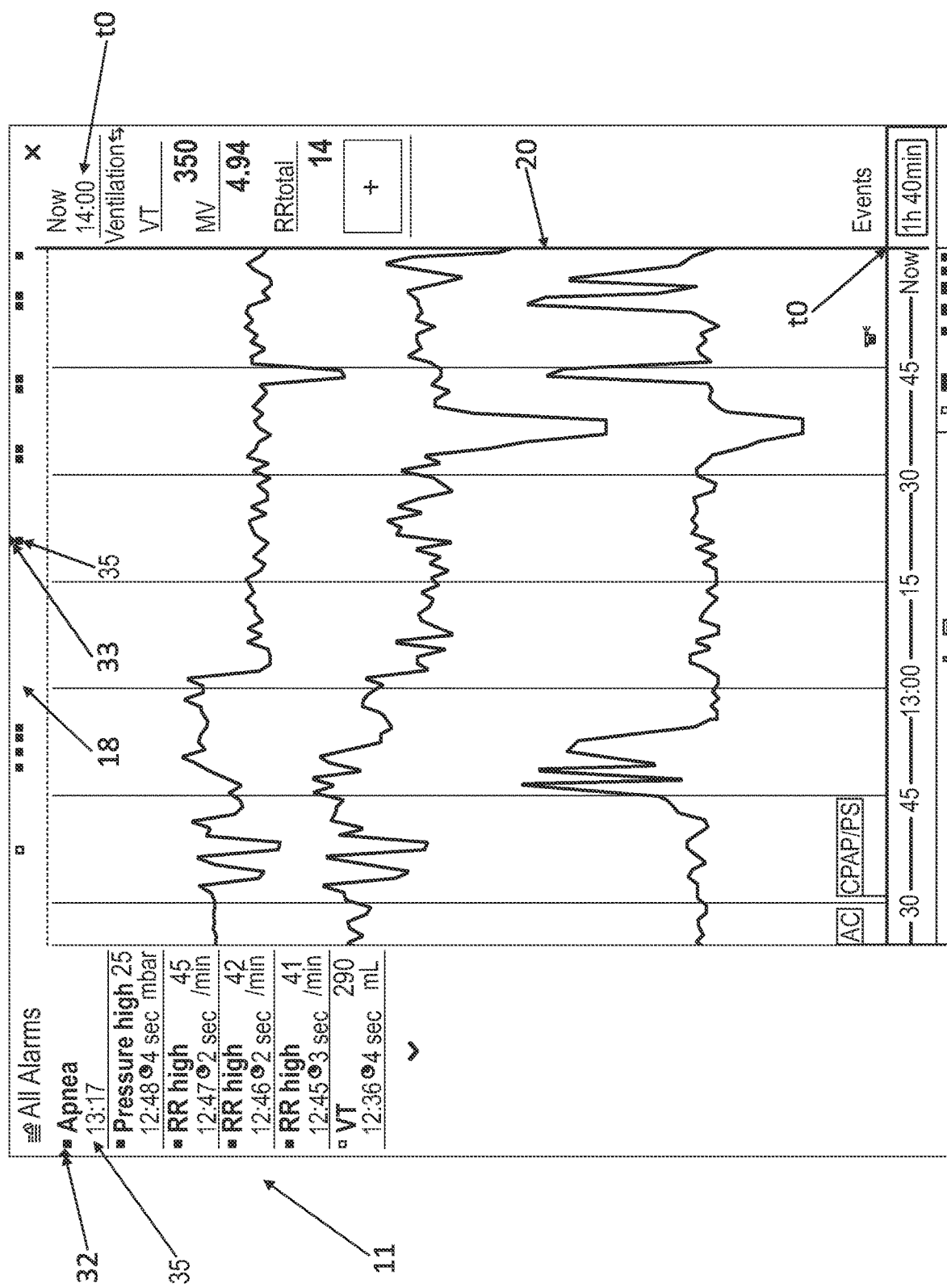
FIG. 22 is a display view showing a correlation indicator is used to display an alarm in the alarm reference sequence.

FIG. 20 through FIG. 22 illustrate how a correlation indicator is used. This correlation indicator makes it easier for a user to find a certain alarm and the time at which this alarm occurred in the alarm reference sequence 18.

The correlation indicator comprises a leading element 32 and a led element 33. In the example shown, the leading element 32 has the shape of a triangle pointing to the right and the lead element 33 has the shape of an upwardly or downwardly pointing triangle. The leading element 32 always points towards the topmost alarm description in the alarm description sequence 11. This alarm description refers to an alarm that may be located in or outside the reference time window T1 and that can currently be selected or cannot currently be selected. The led element 33 points towards the symbol for this topmost alarm in the alarm reference sequence 18. The led element 33 tracks the leading element 32.

In the example according to FIG. 20, the leading element 32 points towards the topmost alarm description, which is the description for the alarm 12.2 (alarm type "MV low," time 01:59 pm). This is also the situation shown in FIG. 11. The led element 33 points towards the symbol in the alarm reference sequence 18 for this alarm 12.2. The user changes the sequence of alarms, whose descriptions are displayed in the alarm description sequence 11. This is suggested by the circle 19 and by the upwardly pointing arrow.

After this user input, the alarm 34 (alarm type "RR high," time 01:55 pm) is the topmost alarm in the alarm description sequence 11, cf. FIG. 21. The leading element 32 points therefore towards the alarm description for the alarm 34. The led element 33 points towards the symbol for this alarm 34 in the alarm reference sequence 18.

FIG. 22 shows the effect of another user input. The leading element 32 points towards the alarm description for the alarm 35 (alarm type "Apnea," time 01:17 pm). The led element 33 points towards the symbol for this alarm 35 in the alarm reference sequence 18.

In the example shown in FIG. 20 through FIG. 22, the leading element 32 always points towards the topmost alarm description in the alarm description sequence 11. It is possible that the user can shift the leading element 32 to another alarm description in the alarm description sequence 11. The led element 33 will then point towards the corresponding alarm in the alarm reference sequence 18. It is also possible that the leading element 32 points towards an alarm in the alarm reference sequence 18 and can be moved by the user. The led element 33 points towards the alarm description for this alarm in the alarm description sequence 11.

Figure 23:
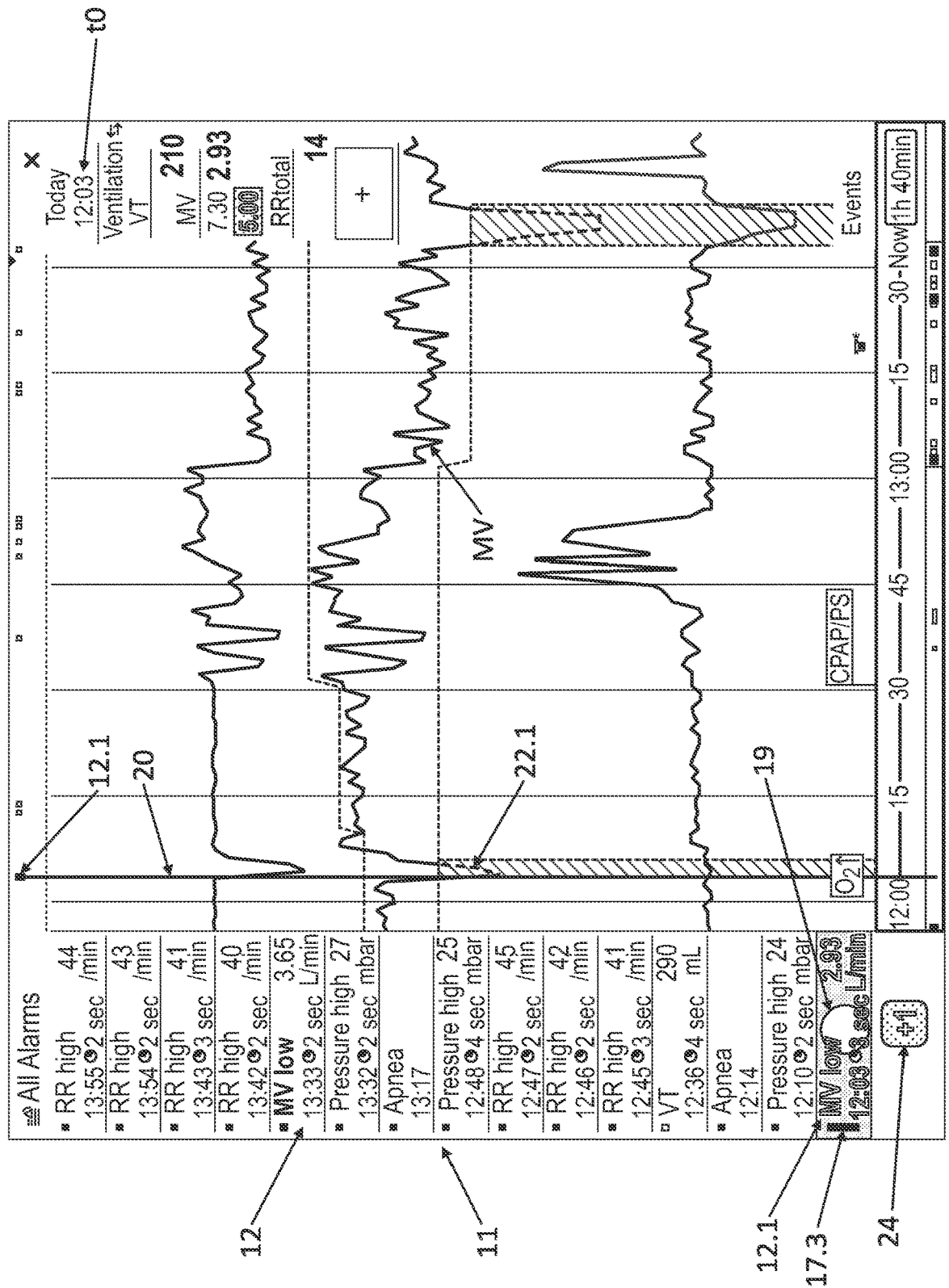
FIG. 23 is a display view showing how a previously selected alarm is displayed.

A user can request a display of the alarms that occurred before the current reference time window T1 that belong to the same alarm type "MV low" as the currently selected alarm 12.1. The user will have the possibility of shifting the reference time window T1. FIG. 23 illustrates that the user is pulling the currently selected alarm 12.1 upward in the alarm description sequence. A place 24 in the alarm description sequence 11, in this case at the lowermost location, becomes free hereby. The number of alarms which were detected in the overall time period T before the reference time window T1 and which likewise belong to the alarm type "MV low" and are not currently displayed in the alarm description sequence 11, in this case "+1," are displayed in this place 24. The position of the place 24 in the far bottom left area indicates that this additional alarm was detected chronologically before the alarms displayed in the alarm description sequence 11.

Figure 24:
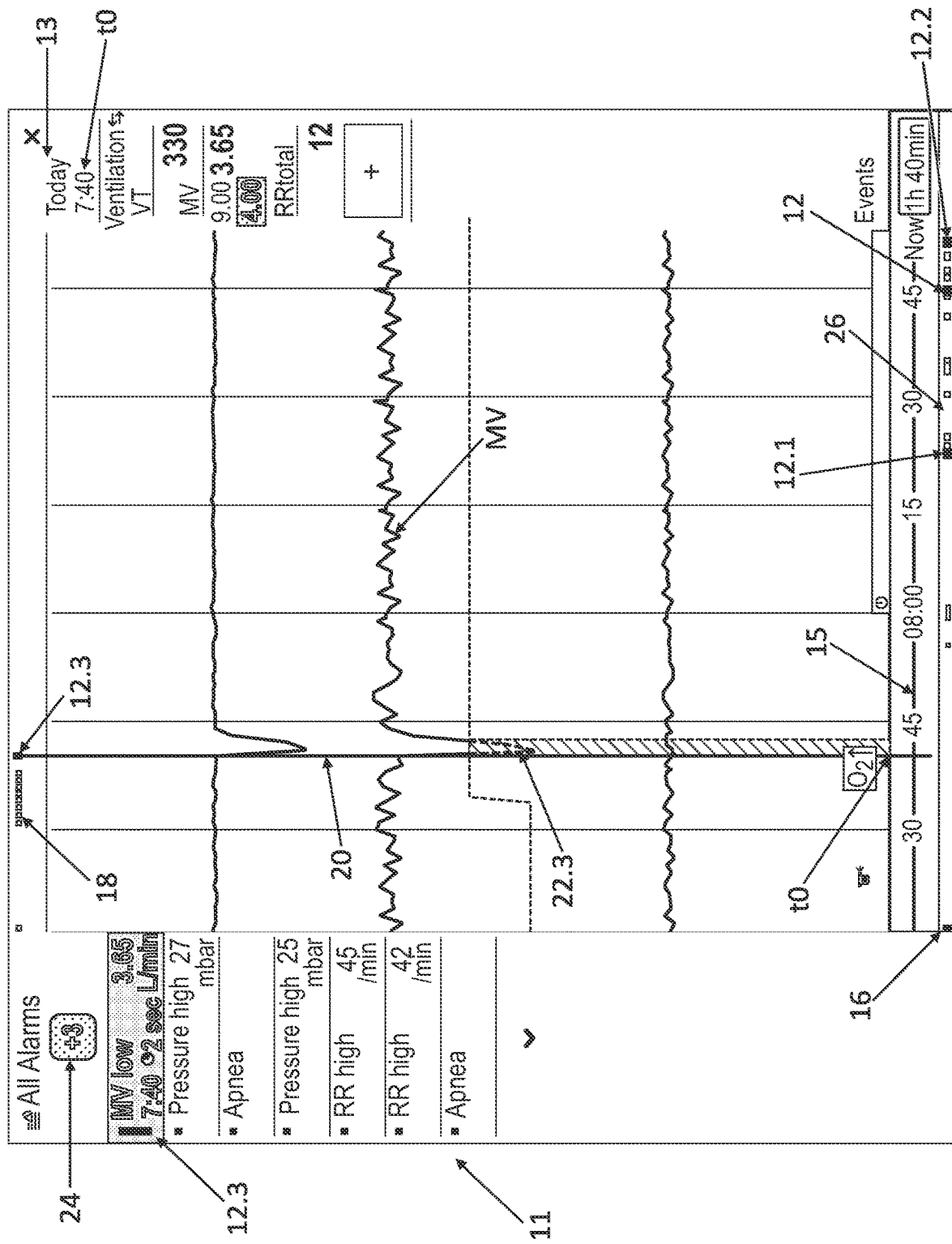
FIG. 24 is a display view showing how a previously selected alarm is displayed.

In the example being shown, the user clicks on the display shown in place 24, cf. FIG. 23. The display "+1" in place 24 refers in this example to the alarm 12.3. FIG. 24 shows the responses:

The alarm description sequence 11 is modified.

The alarm 12.3 is displayed with highlighting in the modified alarm description sequence 11.

It is displayed in place 24 that three additional alarms ("+3") of the same alarm type "MV low" were detected chronologically after the alarm 12.3 displayed now with highlighting. Place 24 is therefore located now above the displayed alarms.

The reference time line 20 jumps to the changed reference time t0, which is the time 07:40 am of the alarm 12.3.

The reference time axis 15 shows a changed reference time window T1, namely, that in which the alarm 12.3 is located. The signal curves in the signal curve area 10, the alarm reference sequence 18 and the alarm reference section 26 refer to this changed reference time window T1 and are changed correspondingly.

The changed reference time t0=0.7:40 am and the signal values at this reference time t0 are displayed in the signal value area 13.

Section 22.3 for the alarm 12.3 is displayed with highlighting.

The overall time period T and the overall alarm sequence 16 remain unchanged.

When the user clicks on the number display "+3," the display according to FIG. 23 will again be shown.

Figure 25:
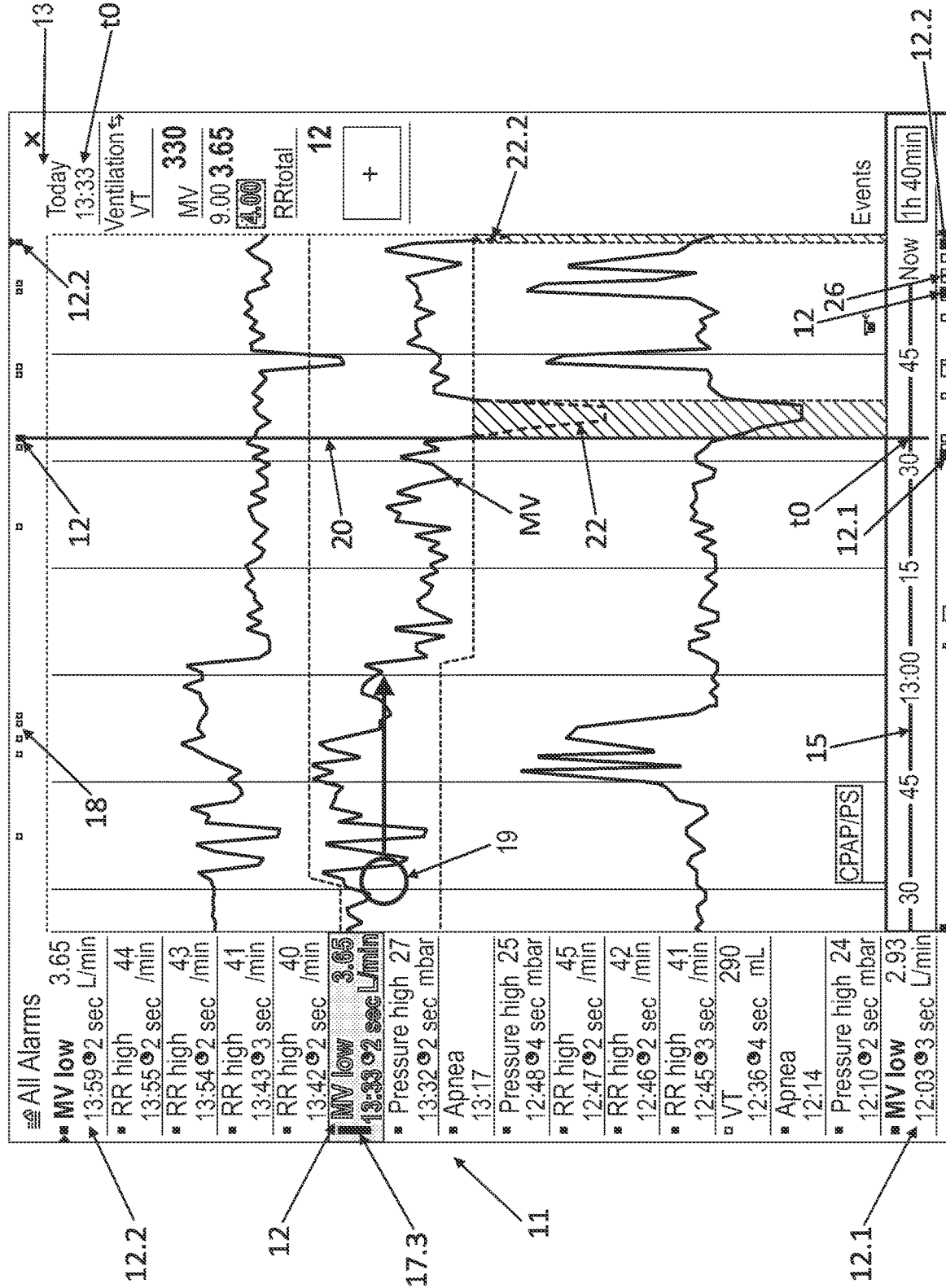
FIG. 25 is a display view showing another type of the user interaction to shift the reference time window.
Figure 26:
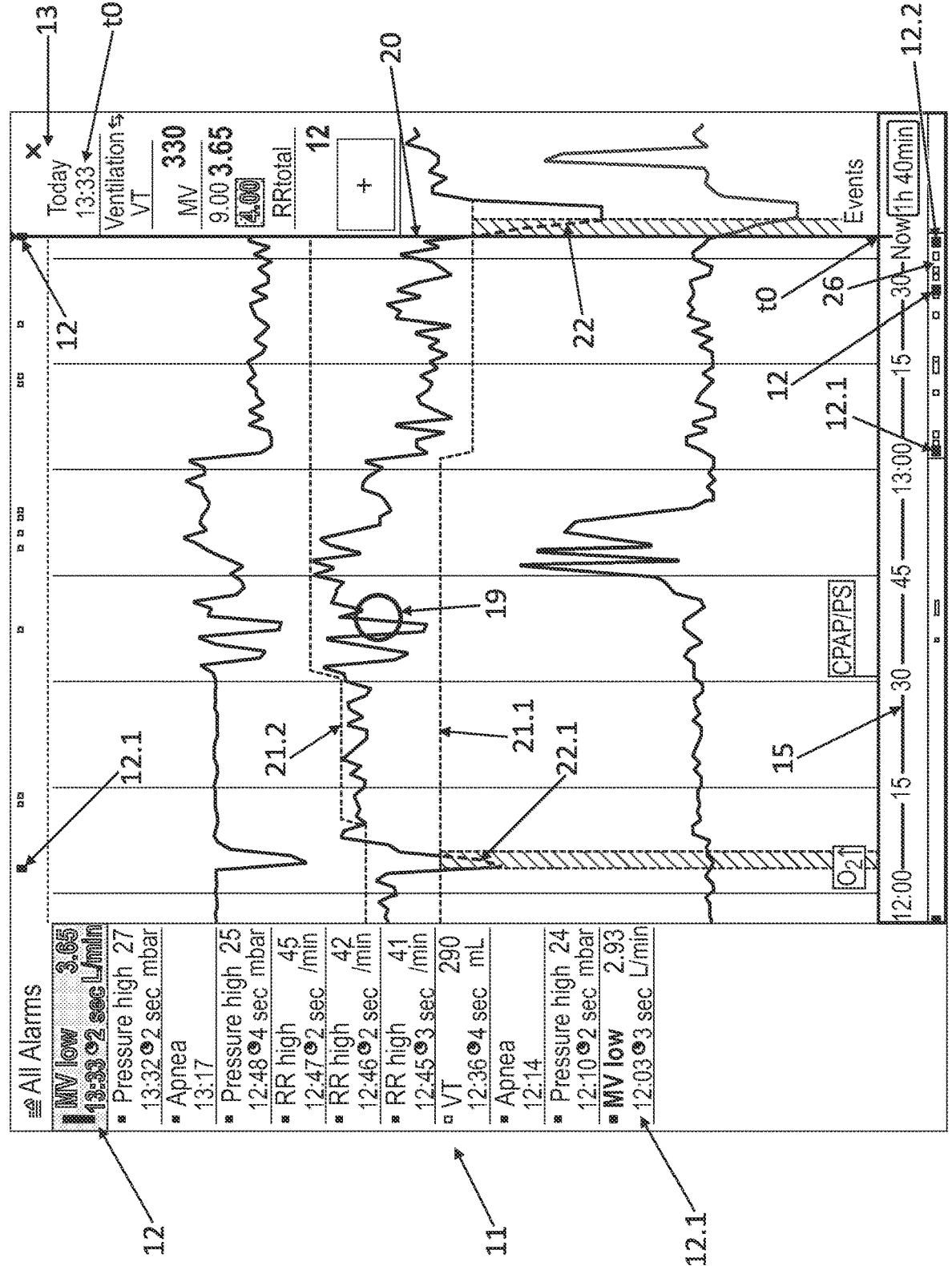
FIG. 26 is a display view showing how previously detected alarms are to be displayed.

FIG. 25 and FIG. 26 show another manner of shifting the displayed reference time window T1. The starting point is again the situation that is shown in FIG. 14. The user touches the display of the signal curve MV in the signal curve area 10 and pulls this to the right, which brings about a shifting of the reference time window T1 to the left, i.e., towards earlier times. The finer time scale remains unchanged. This shifting is suggested in FIG. 25 by the circle 19 and by the arrow.

FIG. 26 illustrates the response to this shifting of the reference time window:

The shifted reference time window T1 is displayed on the reference time axis 15.

The alarm reference sequence 18 and the alarm reference section 26 are modified such that they refer to the shifted reference time window T1 after the modification.

Alarms from the shifted reference time window T1 are displayed in the alarm description sequence 11.

The selection of the alarm 12 and the setting of the reference time t0 remain unchanged.

The reference time line 20 is shifted corresponding to the other position of the reference time t0 on the reference time axis 15.

Figure 27:
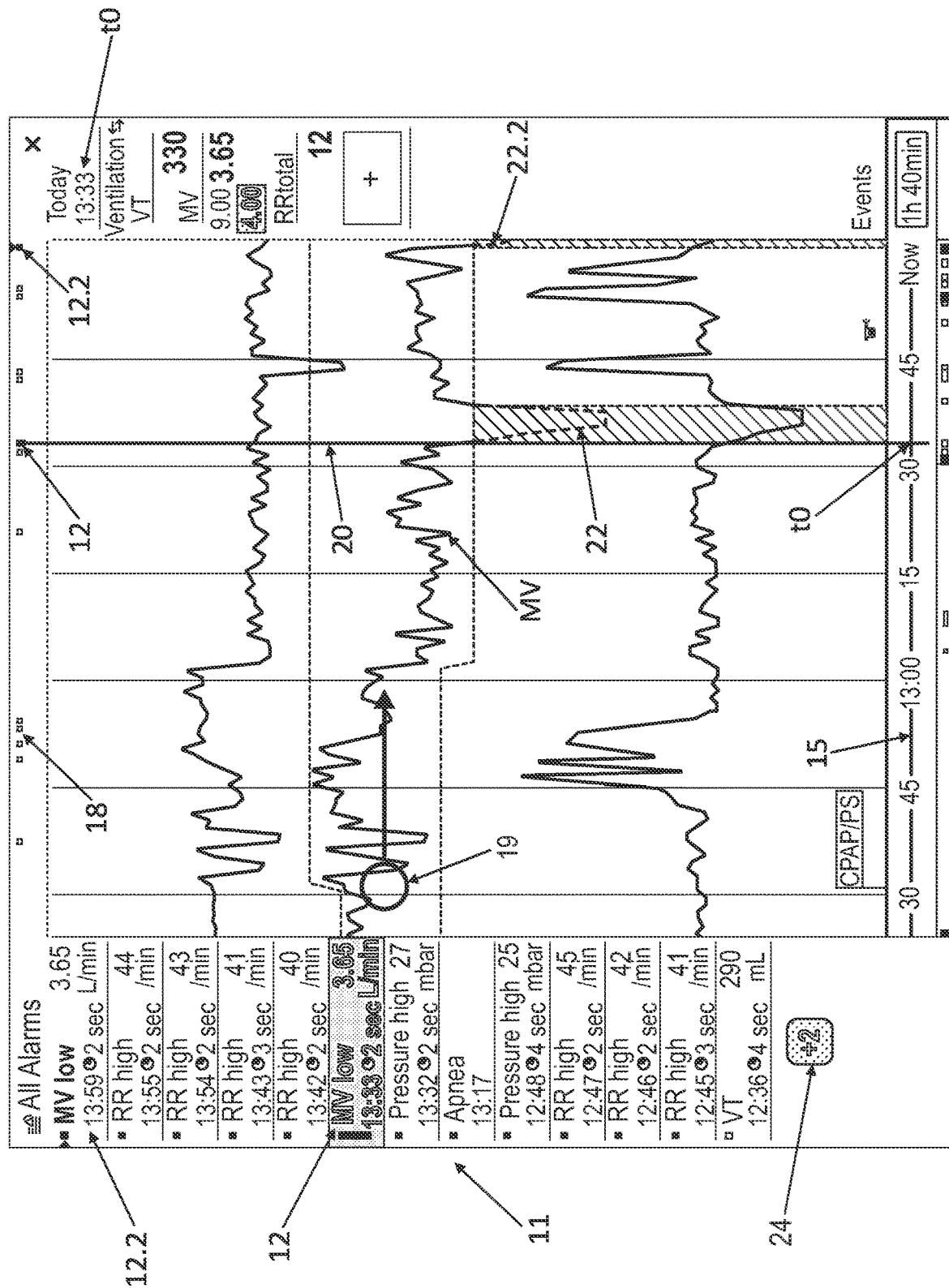
FIG. 27 is a display view showing an alternative embodiment of shifting the reference time window.
Figure 28:
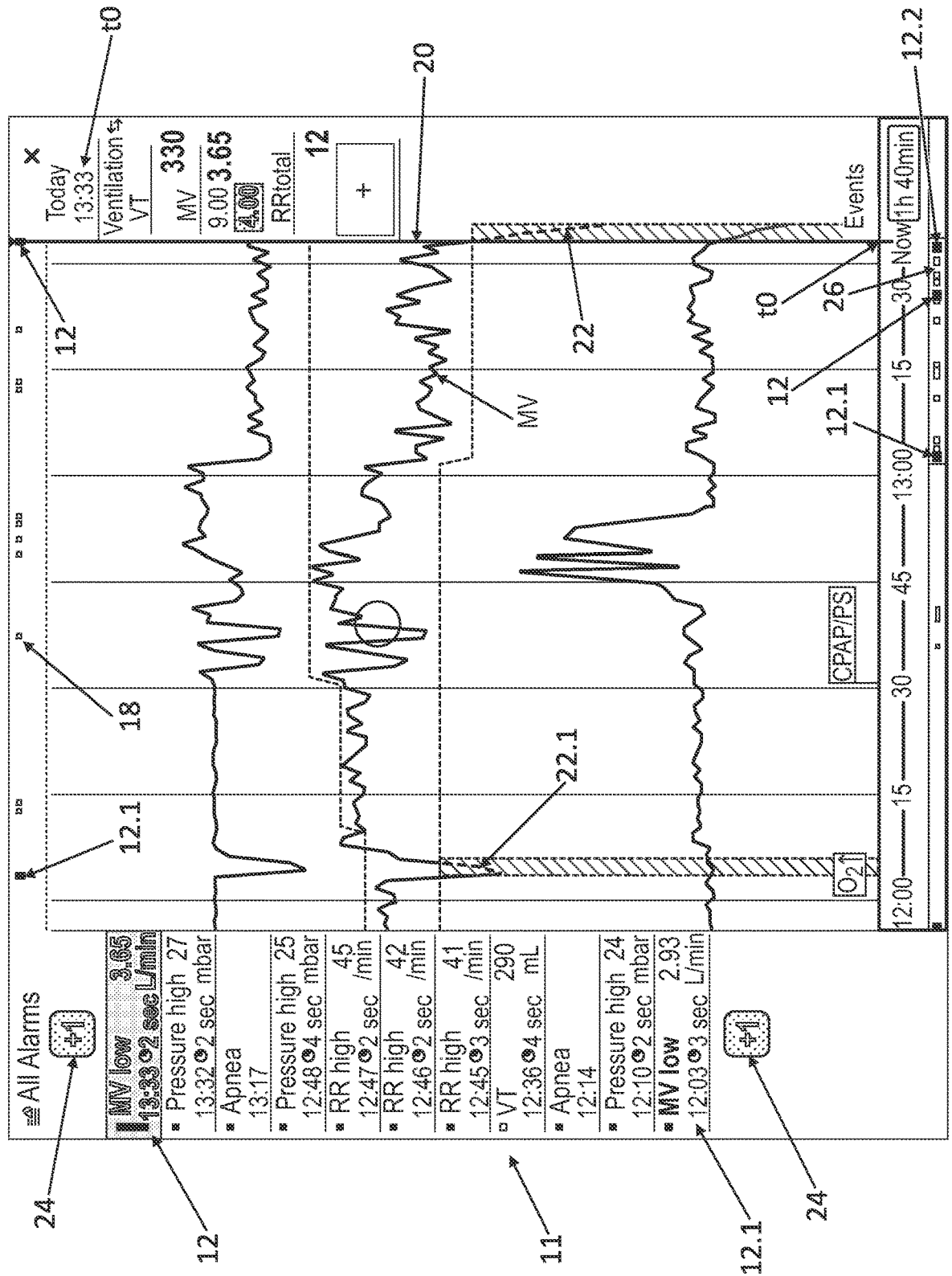
FIG. 28 is a display view showing an alternative embodiment of allowing previously detected alarms to be displayed.

FIG. 27 and FIG. 28 show an alternative embodiment. Only the alarms that are located in the shortened reference time window T1 are displayed in the alarm description sequence 11 in this alternative embodiment. The number of additional alarms of the same alarm type is displayed in place 24.

Figure 29:
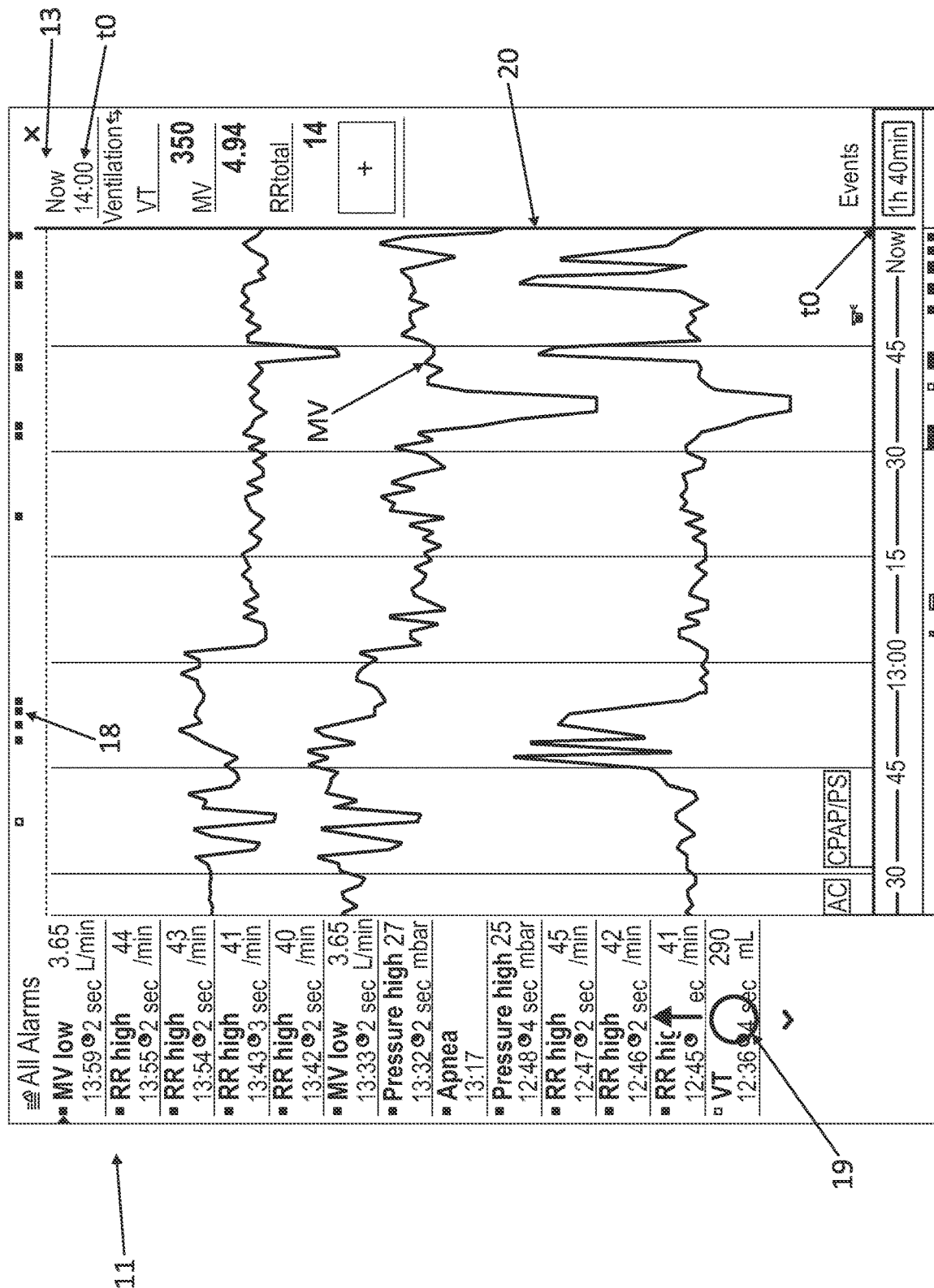
FIG. 29 is a display view showing another type of user interaction for selecting an alarm.

FIG. 29 shows another procedure of how a user can change the alarm sequence, whose alarm descriptions are displayed in the alarm description sequence 11. This makes it possible for the user to select an alarm type, in this case the alarm type "RR high." The starting point is the situation that is shown in FIG. 11. The user selects an alarm, here the alarm of the alarm type "VT" at the time 12:36 pm, in the alarm description sequence 11, and pulls this selected alarm upward in the alarm description sequence 11. This is suggested in FIG. 29 by the circle 19 and by the upwardly pointing arrow.

Figure 30:
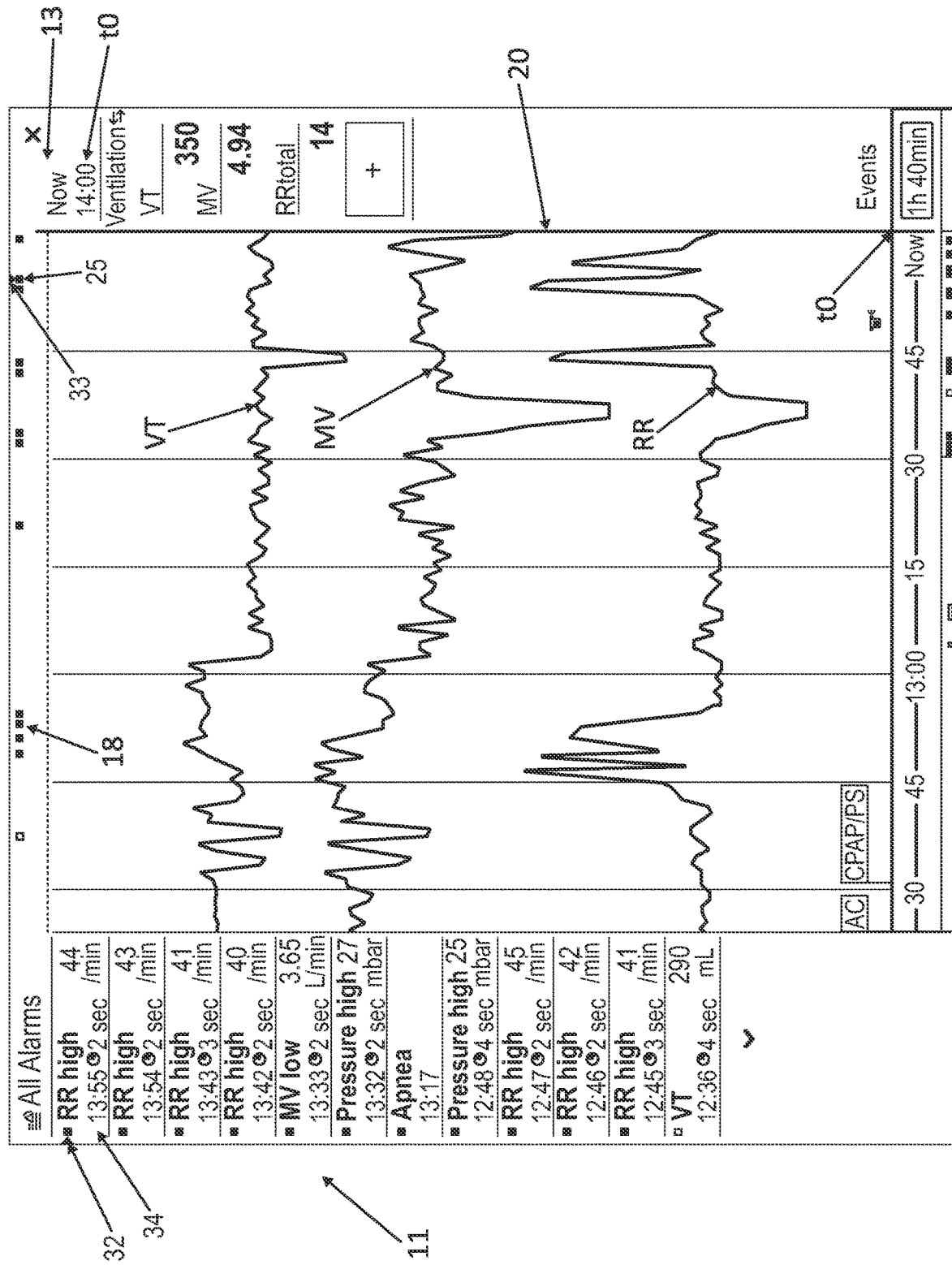
FIG. 30 is a display view showing another type of user interaction for selecting an alarm.

FIG. 30 shows the situation that has developed after the shifting. The alarm 34 of the alarm type "RR high" at the time 01:55 pm is shown as the topmost alarm in the alarm description sequence 11.

In the applications hitherto described, the reference time t0 was the current time (here: 02:00 pm) or the time of an alarm. The user may temporarily also predefine any other desired reference time t0. A selection of an alarm, which was made previously is preferably maintained. Furthermore, the sequence of alarms, whose alarm descriptions are displayed in the alarm description sequence 11, is preferably maintained.

Figure 31:
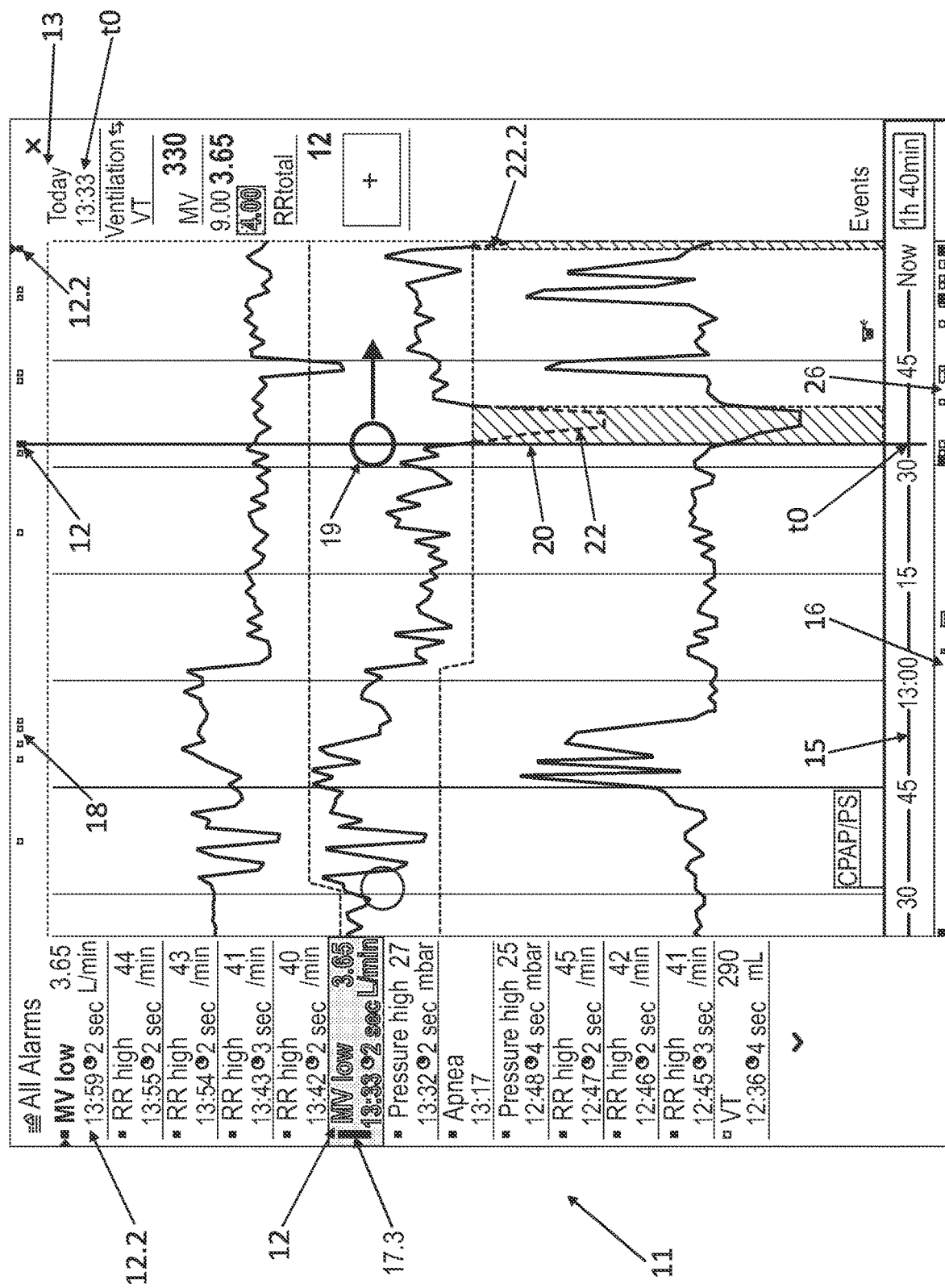
FIG. 31 is a display view showing another type of user interaction for shifting the reference time window.

The setting of a temporary reference time t0 is illustrated in FIG. 31. The preferably vertical reference time line 20 acts as a cursor. The user touches this reference time line 20 and shifts it to the right and holds it at a desired time, which is suggested in FIG. 31 by the circle 19 and by the arrow pointing to the right.

Figure 32:
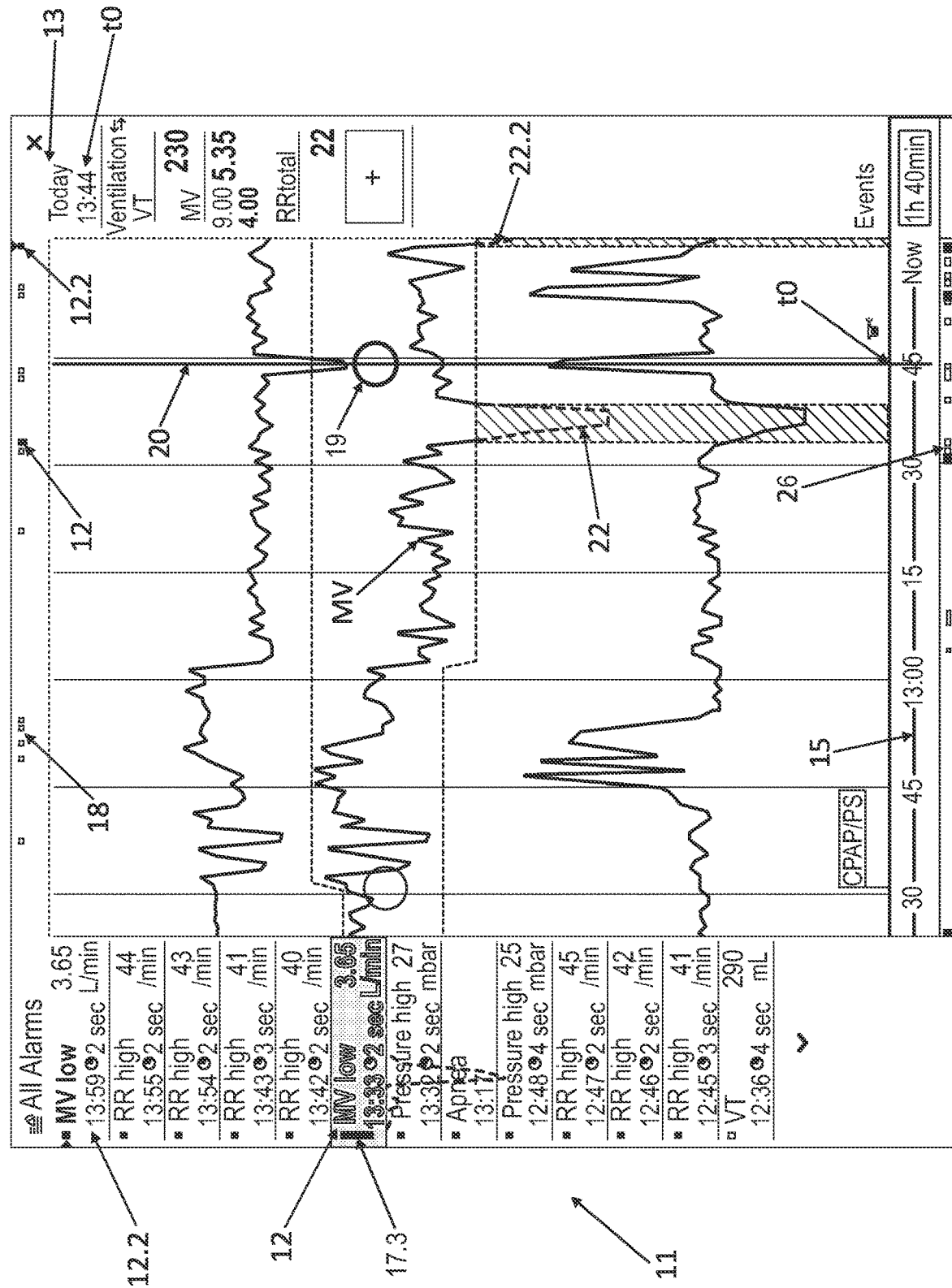
FIG. 32 is a display view showing another type of user interaction for shifting the reference time window.

By the shifting and holding, the user predefines as the temporary reference time t0 the time 01:44 pm, which is not necessarily the time of an alarm. FIG. 32 illustrates with a circle 19 the location at which the user is holding the reference time line 20. In addition, FIG. 32 shows the response. The changed reference time t0 as well as the signal values at this reference time t0 are displayed in the signal value area 13. The reference time window T1 as well as the selection of the alarm type "MV low" and the selection of the alarm 12 remain unchanged.

Figure 33:
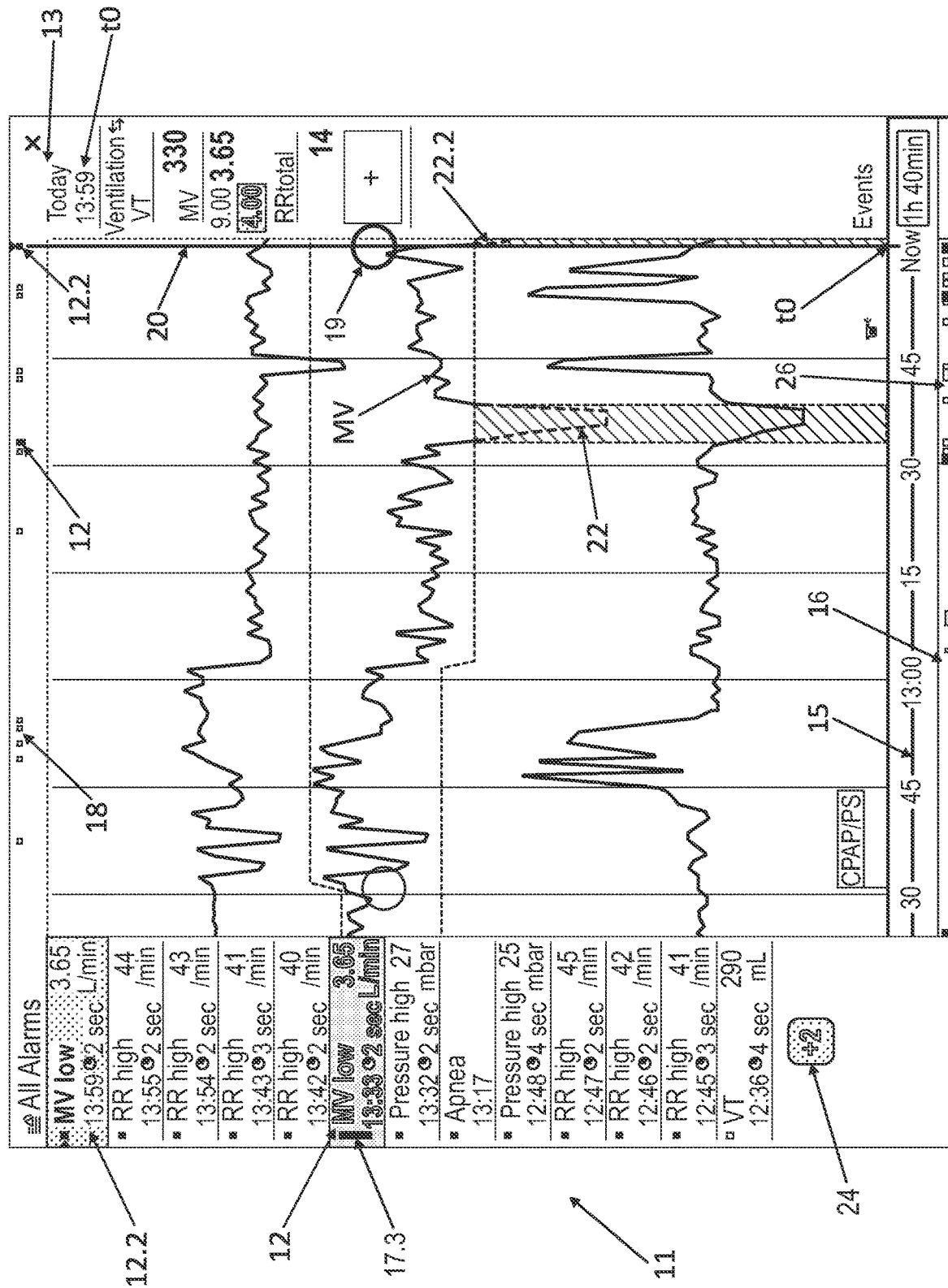
FIG. 33 is a display view showing another type of user interaction for shifting the reference time window.

It is also possible to specify as the reference time t0 the time of an alarm and thereby to select this alarm. FIG. 33 shows an example. The user has shifted the reference time line 20 farther and selected the time 01:59 pm, which is the time of the alarm 12.2, as the reference time t0. The user preferably holds the line 20 for the reference time t0 at the time of the alarm 12.2. This holding is suggested by the circle 19 in FIG. 33.

The following responses are triggered:

The selected alarm 12.2 is additionally displayed with highlighting in the alarm description sequence 11. The selection of the alarm 12, which was made before, is preserved.

The reference time t0 (here: 01:59 pm) as well as the signal values at this reference time t0 are displayed again in the signal value area 13.

The reference time window T1, the reference time axis 15 as well as the displays in the alarm reference sequence 18 and in the alarm reference section 26 remain unchanged.

In one embodiment, this reference time t0 remains selected only as long as the user is holding the reference time line 20 at the corresponding location. The user can, of course, shift and hold the reference time line 20, and the display is correspondingly adapted. As soon as the user ceases to hold the reference time line 20 and lets it go, the time of the alarm selected last will again become the reference time t0. As a result, the situation shown in FIG. 31 with the selected alarm 12 will be established.

Figure 34:
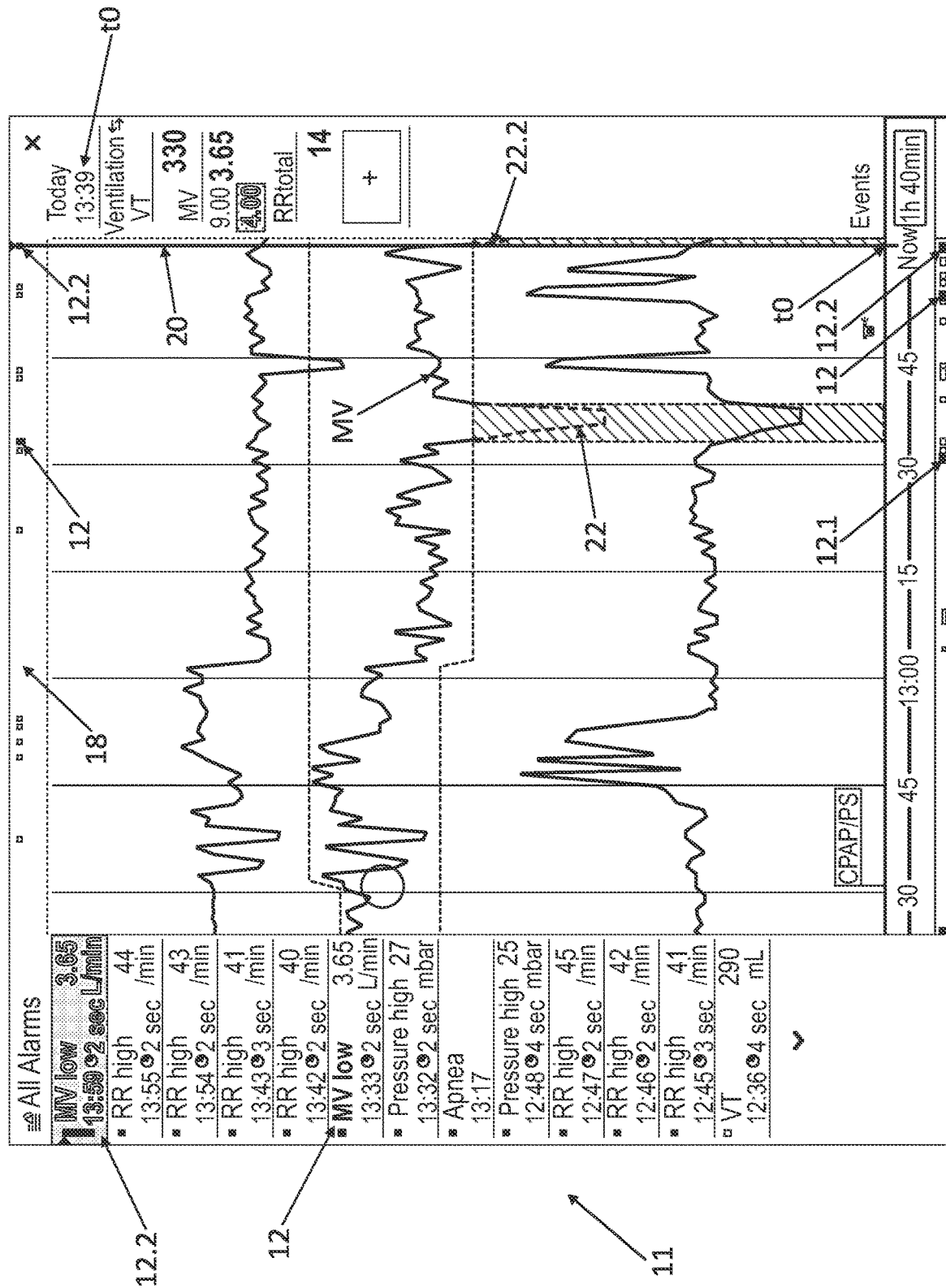
FIG. 34 is a display view showing another type of the user interaction for shifting the reference time window.

The user may also shift the reference time line 20 to the time of the alarm 12.2 and leave it there. FIG. 34 shows the triggered responses:

The time of the alarm 12.2 is the reference time t0.

Instead of the alarm 12, the alarm 12.2 is selected and it is marked as highlighted in the alarm description sequence 11.

The previously selected alarm 12 is not marked by highlighting in the alarm description sequence 11, but it is of the same alarm type as the now selected alarm 12.2 and it is therefore displayed differently than the other types of alarms, namely, in bold letters.

Figure 35:
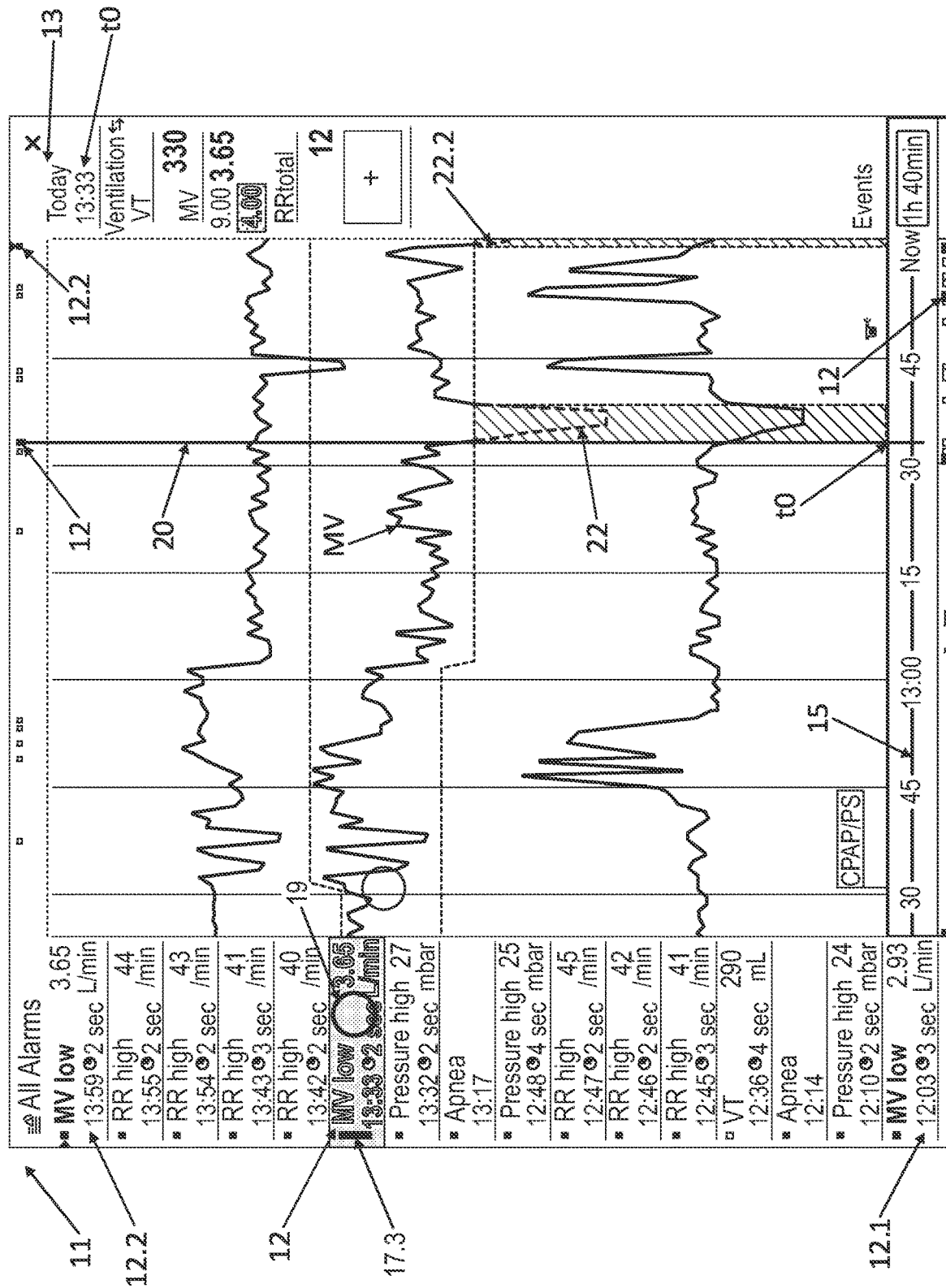
FIG. 35 is a display view showing how explanations for an alarm are displayed.
Figure 36:
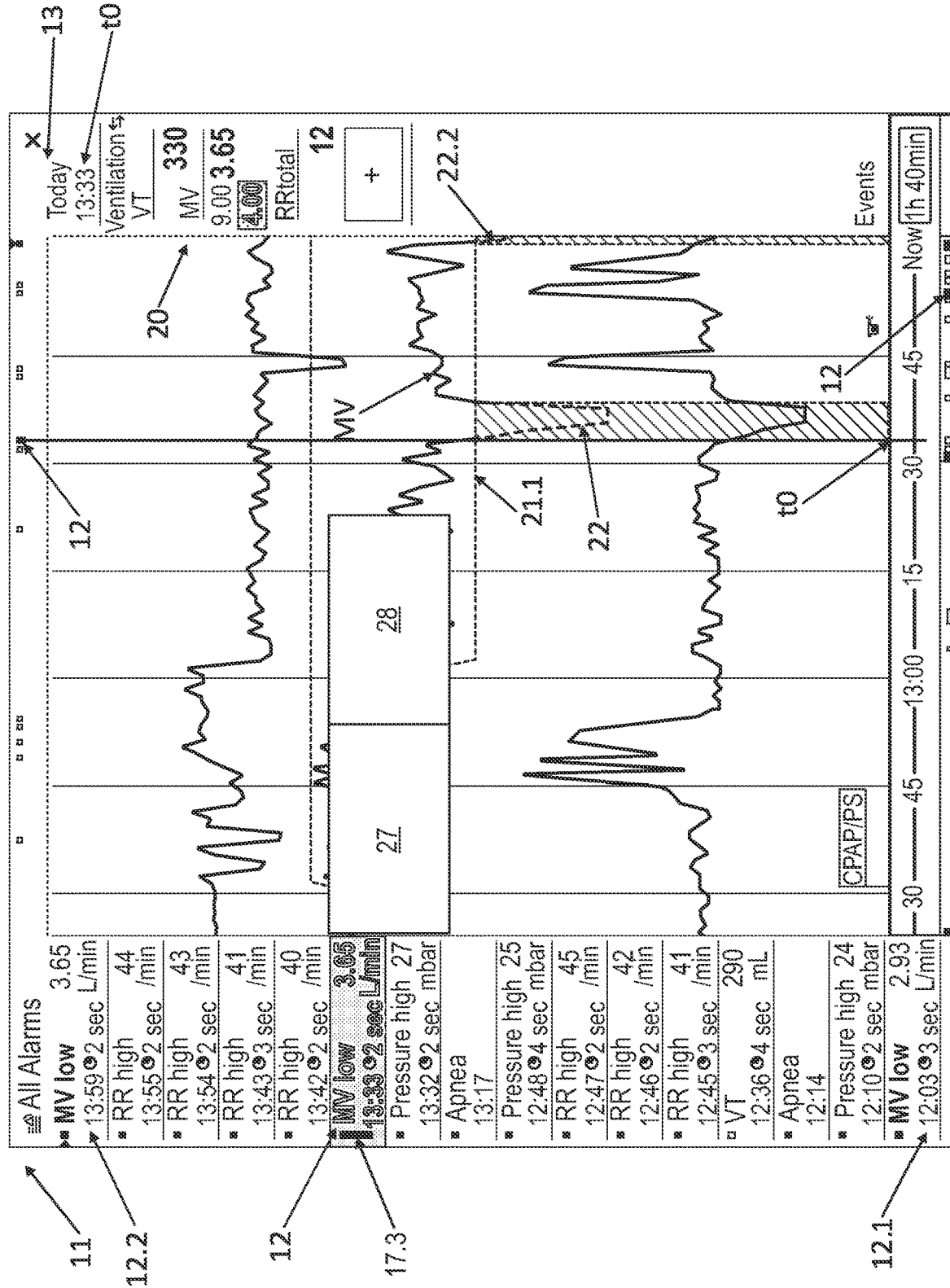
FIG. 36 is a display view showing how explanations for an alarm are displayed.

The user can get explanations for an alarm shown to him. This is shown in FIG. 35 and in FIG. 36. The situation shown in FIG. 35 is the same that is also shown in FIG. 14. The user has selected the alarm 12, and this alarm 12 is marked by highlighting.

The user selects the highlighting of the alarm 12 in the alarm description sequence 11, which is illustrated in FIG. 35 by the circle 19. In response, two text windows 27 and 28 are displayed next to the selected alarm 12. A cause or explanation for the alarm 12, here that the value has dropped below the predefined lower limit 21.1, is displayed in the text window 27. Possible remedies to eliminate the cause are displayed in the text window 28.

Figure 37:
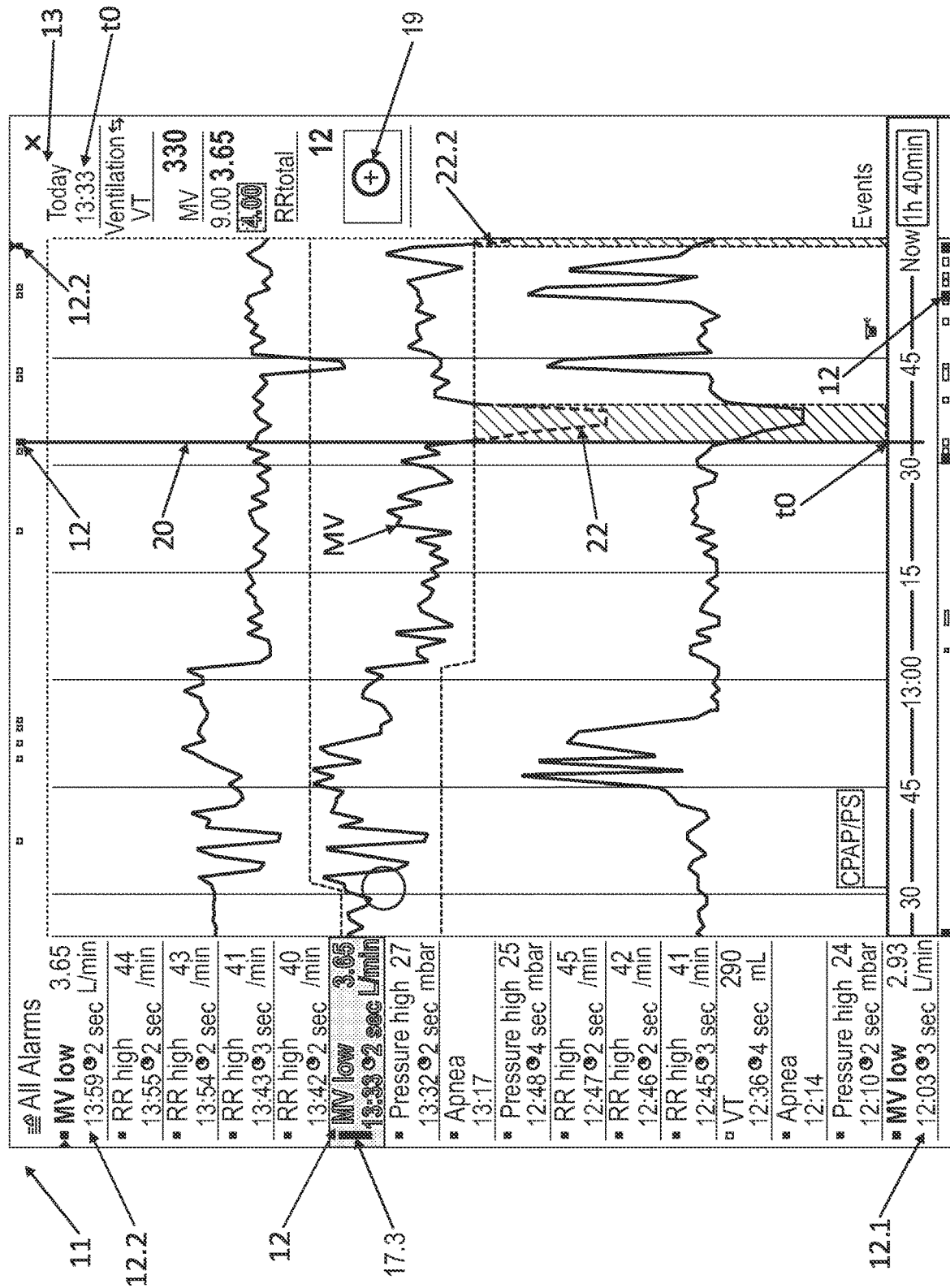
FIG. 37 is a display view showing how another signal is selected and how the time curve of that signal is additionally displayed.
Figure 38:
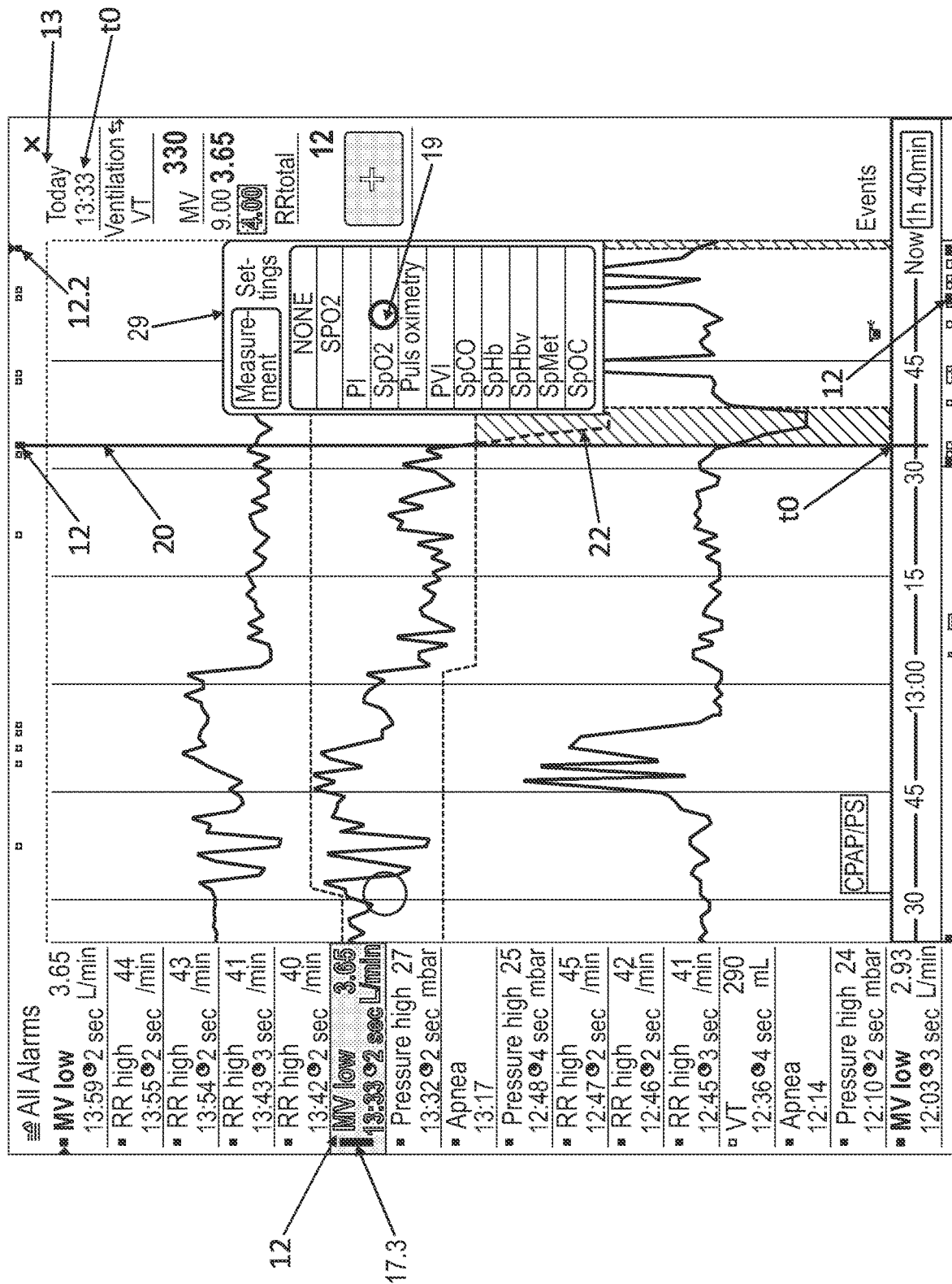
FIG. 38 is a display view showing how another signal is selected and how the time curve of that signal is additionally displayed.

The user can have shown to him/her the time curves of corresponding or other signals or even variables, which can be set on the ventilator 1. This is illustrated by FIG. 37 and FIG. 38.

The starting point is again the situation shown in FIG. 14. The user selects a symbol ("+") in the signal value area 13, which is displayed by the circle 19 in FIG. 37. In response, a selection menu 29 is displayed, which offers two tabs as well as the names of different signals for the selection, cf. FIG. 38. The first tab "Measurement" makes it possible to select a patient-related signal, which shall be additionally displayed. The second tab "Settings" makes it possible for the user to see that value that a previously selected variable, which can be set on the ventilator 1, currently has. However, the user cannot change this value in the user surface shown in the exemplary embodiment, but only in another manner, preferably directly at the ventilator 1.

Figure 39:
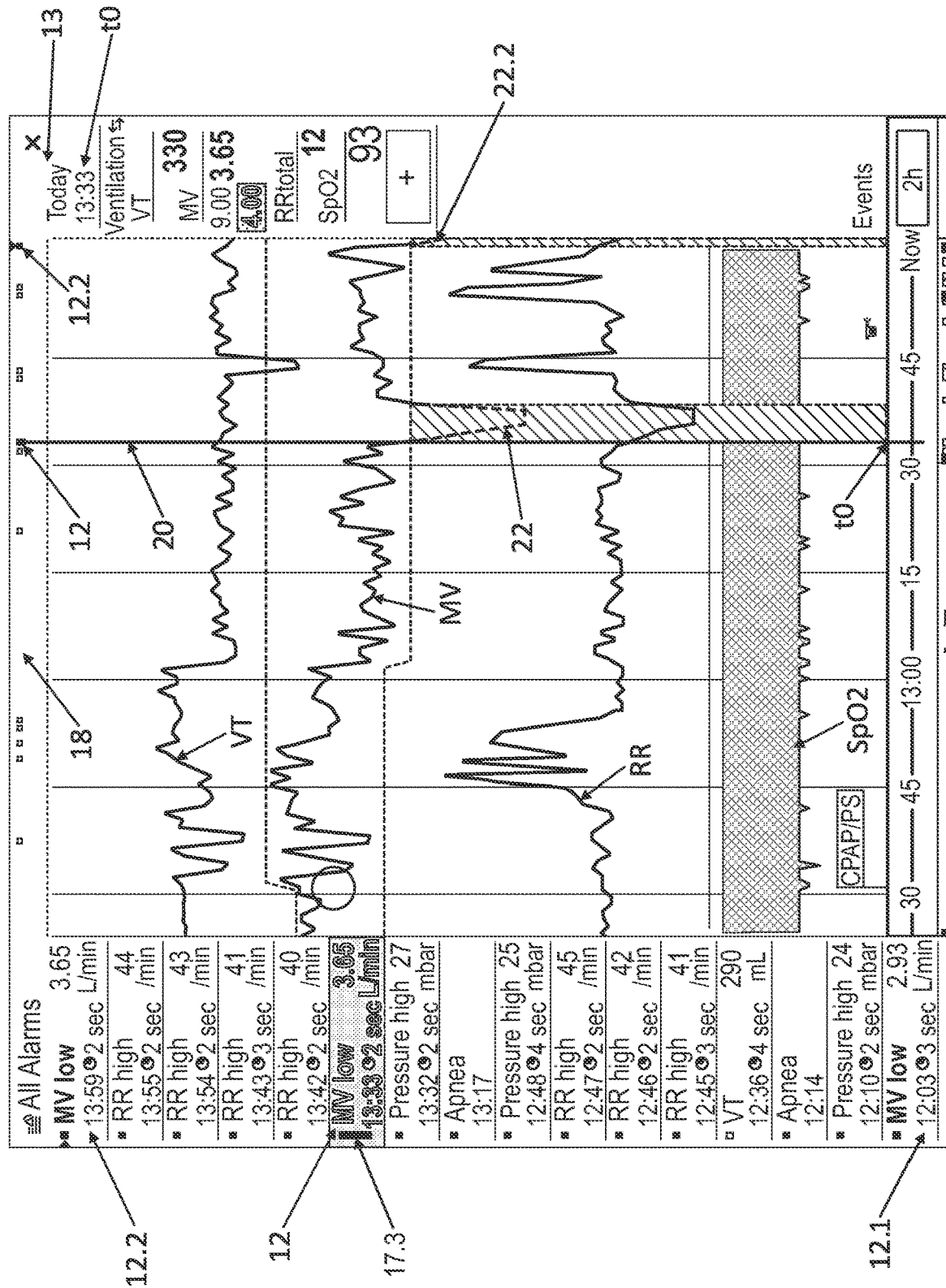
FIG. 39 is a display view showing how another signal is selected and how the time curve of that signal is additionally displayed.

The first tab is activated in the example being shown. The user selects, for example, the signal SpO2, which is displayed by the circle 19 in FIG. 38. The responses to this selection are shown in FIG. 39:

The time curve of the signal SpO2 is displayed in addition to the time curves of the signals VT, MV and RR.

The value 93 of the signal at the reference time t0, here 01:33 pm, is additionally displayed in the signal value area 13.

The selection of the alarm 12, of the reference time window T1 and of the reference time t0 will again remain unchanged.

Figure 40:
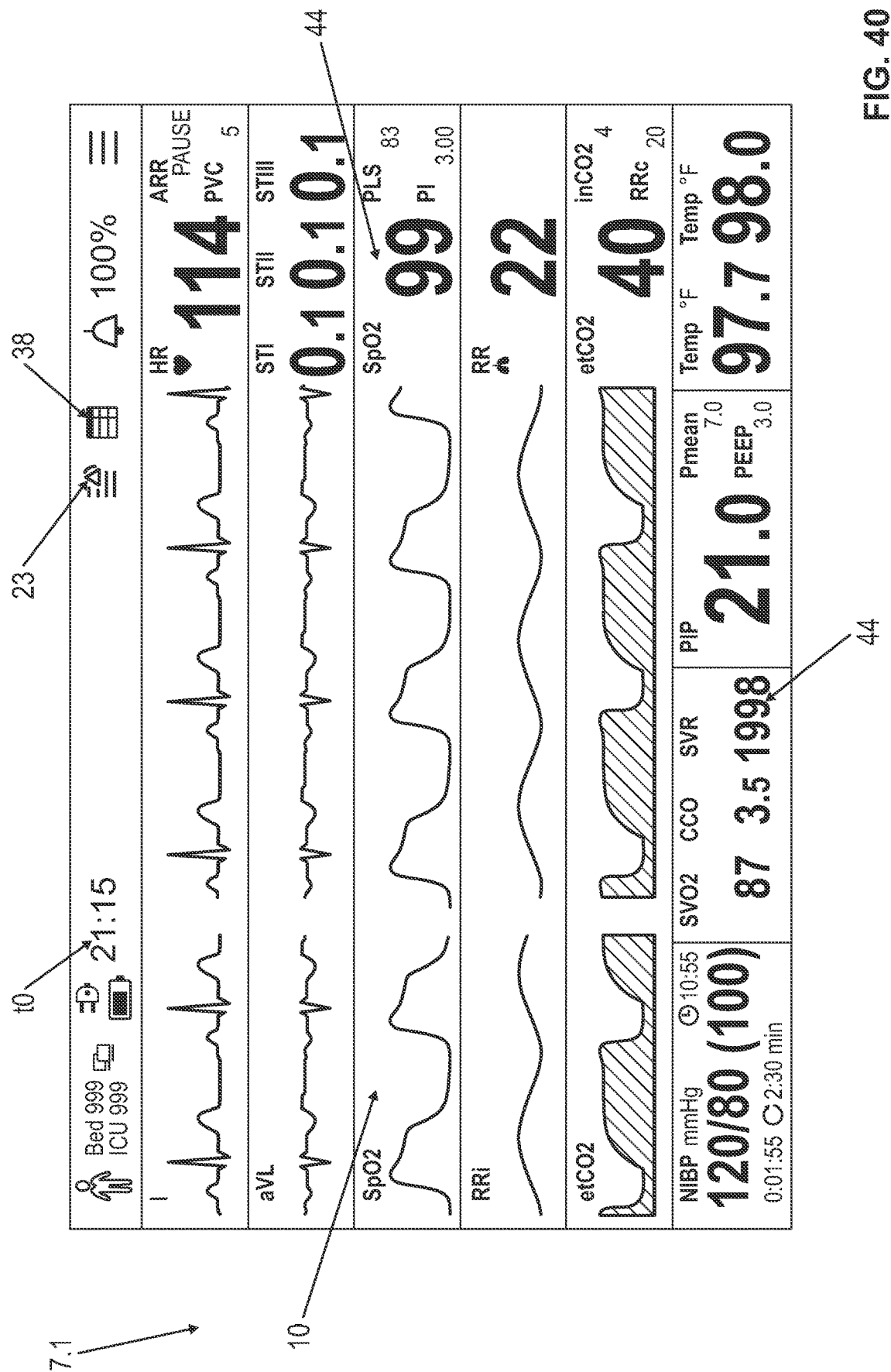
FIG. 40 is a display view showing another embodiment with a smaller display screen: Situation before the selection of an alarm.

FIG. 40 shows another embodiment, which can be embodied on a smaller display screen, specifically in a situation before the selection of an alarm. Identical reference numbers have the same meanings as above. The last 30 minutes until the current time t0 are used as the current reference time window T1. Two operating elements, which can be activated by touching, are shown:

an operating element 23 for fading in or fading out alarm descriptions, and an operating element 38, which makes possible a direct entry, which will be described below.

Figure 41:
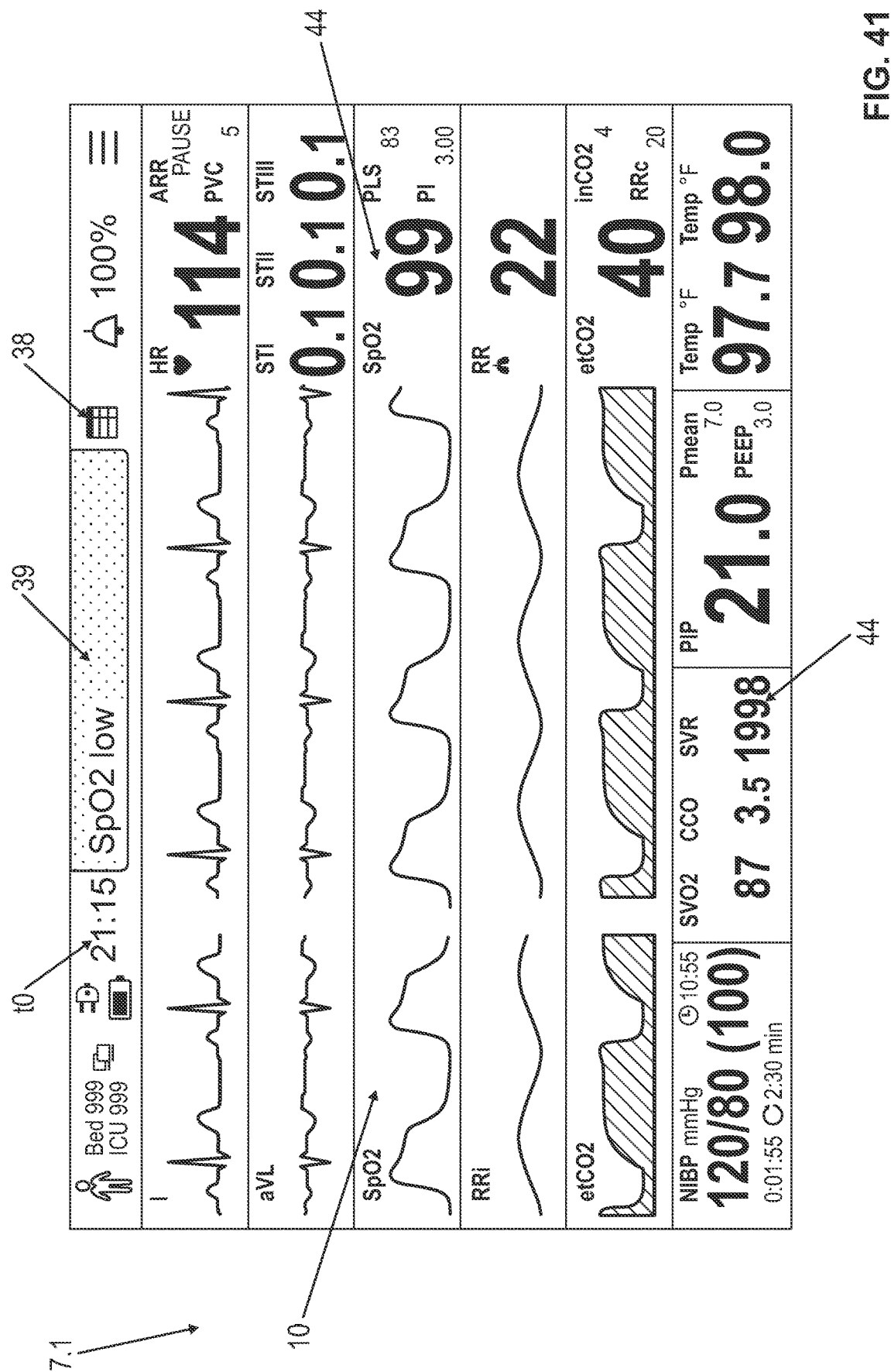
FIG. 41 is a display view showing the embodiment according to FIG. 40: The current alarm is displayed.

In the situation shown in FIG. 41, an alarm, which occurs at the reference time to equaling 09:15 pm, namely, the alarm 40 of the alarm type "SpO2 low," is displayed in field 39. The current signal values of the displayed signal curves are displayed in an area 44.

Figure 42:
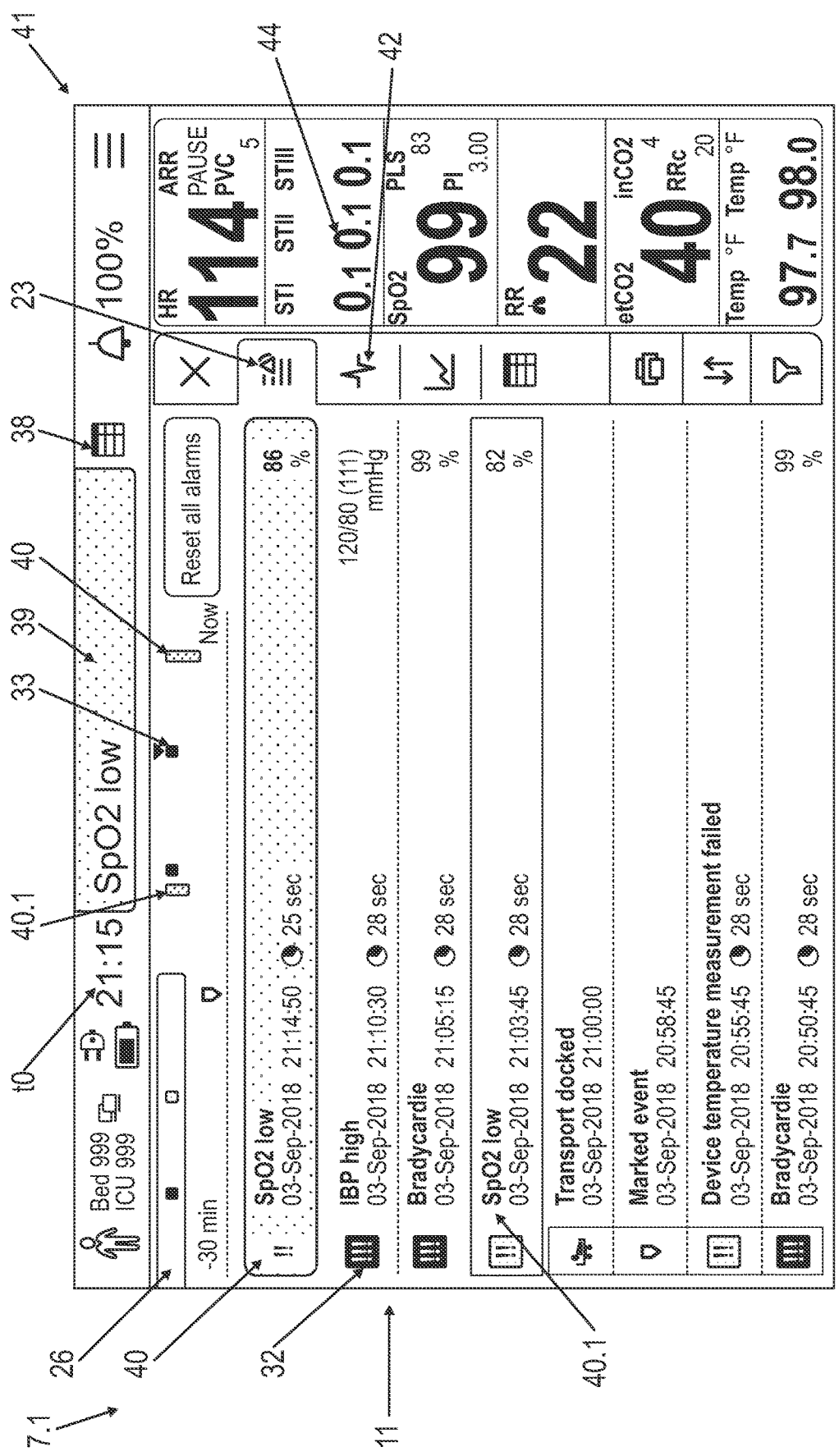
FIG. 42 is a display view showing the embodiment according to FIG. 40: The alarm description sequence is displayed.

The user actuates the operating element 38 or the field 39. FIG. 42 shows the responses to this input. A plurality of operating elements are displayed in a column 41 on the display screen 7.1, which column is faded in now. The alarm reference section 26 is displayed from now on. In addition, an alarm description sequence 11 is displayed in the vertical direction, the most recent alarm 40 being at the topmost location. In order to save space on the display screen 7.1, the alarm description sequence 11 is displayed in the place that was occupied by the signal curve area 10 in the situation shown in FIG. 40. The most recent alarm 40 occurred at 09:14:50 pm.

An alarm 40.1 of the same alarm type "SpO2 low" occurred at 09:03:45 pm. The user has selected this alarm 40.1, which is suggested by the border. In addition, additional alarms are displayed, e.g., "bardycardia" at 09:05:15 pm, an event marking, namely, "Marked Event" at 08:58:45 pm, and a special action, which is performed on the patient P, for example, a transport ("Transport docked," which is ended at 09:00:00 pm). The event marking was set by the user manually in order to record a special situation thereby. The user can later analyze this special situation. In one embodiment, the user can enter a text comment on this special situation (not shown). In addition, a leading element 32 and a led element 33 of the correlation indicator are again shown, cf. also FIG. 20 through FIG. 22.

A user can roll ("scroll") the detail of the alarm description sequence 11 shown on the display screen 7.1 upward and downward. If an alarm not shown in the current alarm reference section 26 reaches now the location of the leading element 32, the reference time window T1 and the alarm reference section 26 are adjusted such that this alarm is located now in the reference time window T1. In one embodiment, the finer time scale remains unchanged in this case as well.

Figure 43:
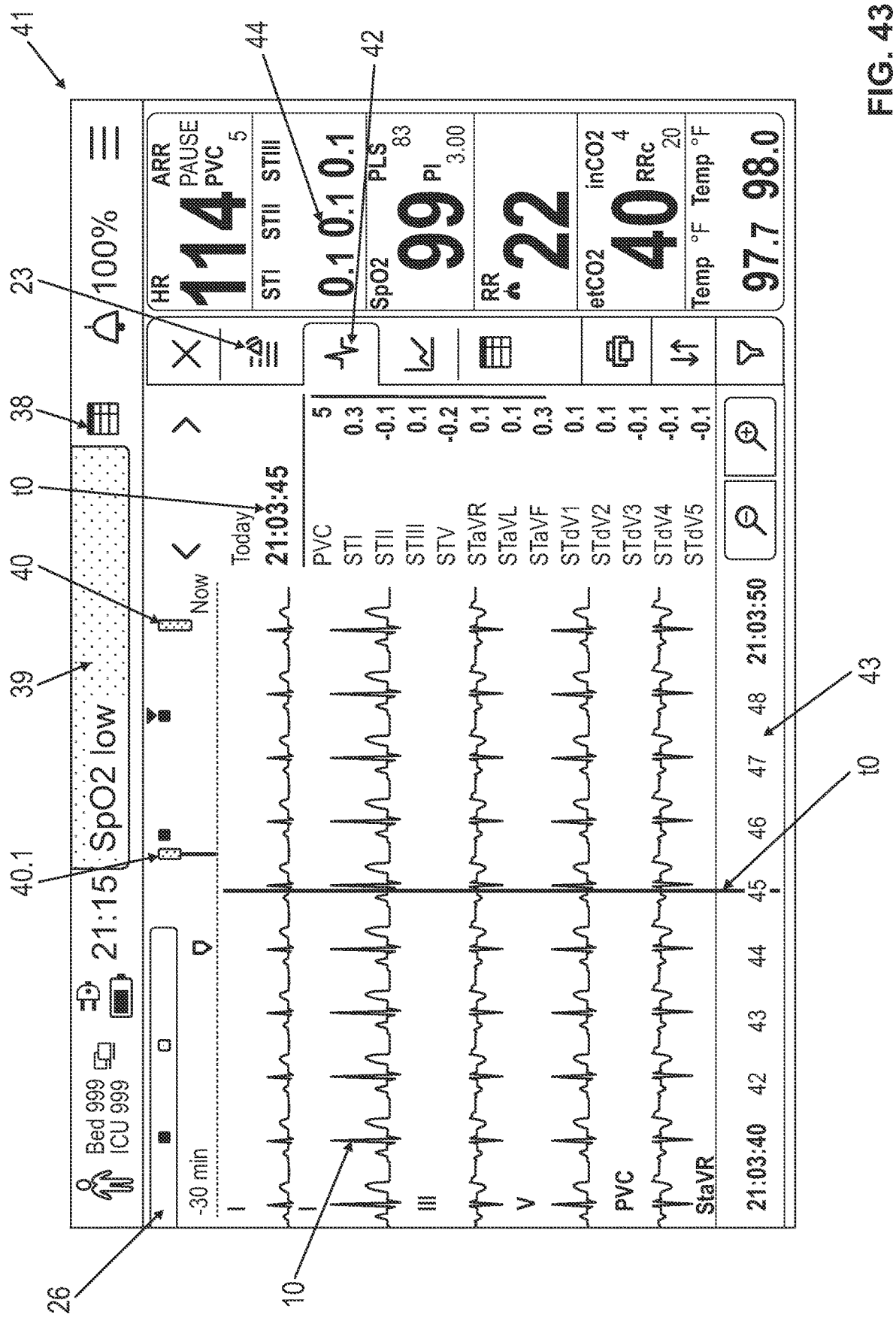
FIG. 43 is a display view showing the embodiment according to FIG. 40: The waveform snippet view is displayed.

In the example according to FIG. 43, the user has selected the description of the alarm 40.1 in the alarm description sequence 11. The reference time t0 jumps as a result to the time of this alarm 40.1, namely, to 09:03:45 pm. In addition, the user has actuated the operating element 42 in column 41. A so-called waveform snippet view is displayed in response to this in the signal curve area. A time axis 43 is displayed under this signal curve area. The reference time t0 is located in the middle of this time axis 43. The user can change the current time resolution of the waveform snippet view by actuating the operating elements marked with "+" and "−" in the two magnifiers shown on the right next to the time axis 43. Using the operating elements "<" and ">" on the right next to the alarm reference section 26, the user can select alarms of the same alarm type that occurred earlier in time and later in time and shift thereby both the reference time t0 and the reference time window T1.

Figure 44:
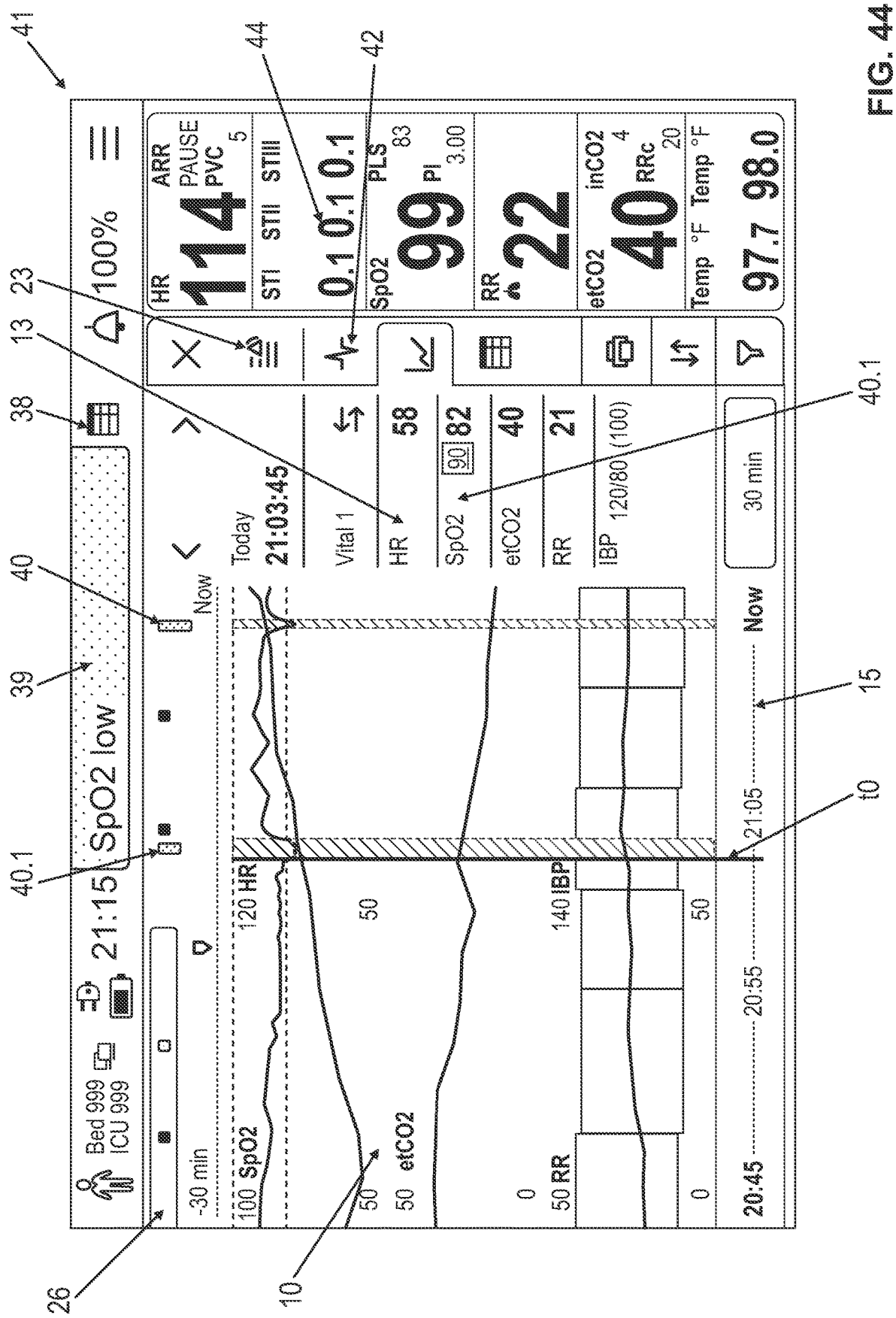
FIG. 44 is a display view showing the embodiment according to FIG. 40: Smoothened signal curves are displayed.

FIG. 44 shows how the curves of different signals are displayed as trend curves, wherein the signals were smoothened before by calculation in one embodiment. The display of the trend curves depends on the selected time resolution, on the scanning frequency and on the number of pixels to be displayed. The signal curves refer to the reference time window T1, which goes back by half an hour. The reference time axis 15 for the reference time window T1 is displayed under the central signal curve area 10.

In addition, the values of the signals shown at the reference time t0 equaling 09:03:45 pm are displayed in an area 13 in the situation that is shown in FIG. 44. The value for SpO2 at the reference time t0 was too low (alarm). Therefore, the lower limit of the desired range for SpO2, here the value 90, is also displayed next to the signal value 82 at the reference time t0 in the display of the alarm 40.1 in the signal value area 13, the number for the lower value being displayed by underlining.

Figure 45:
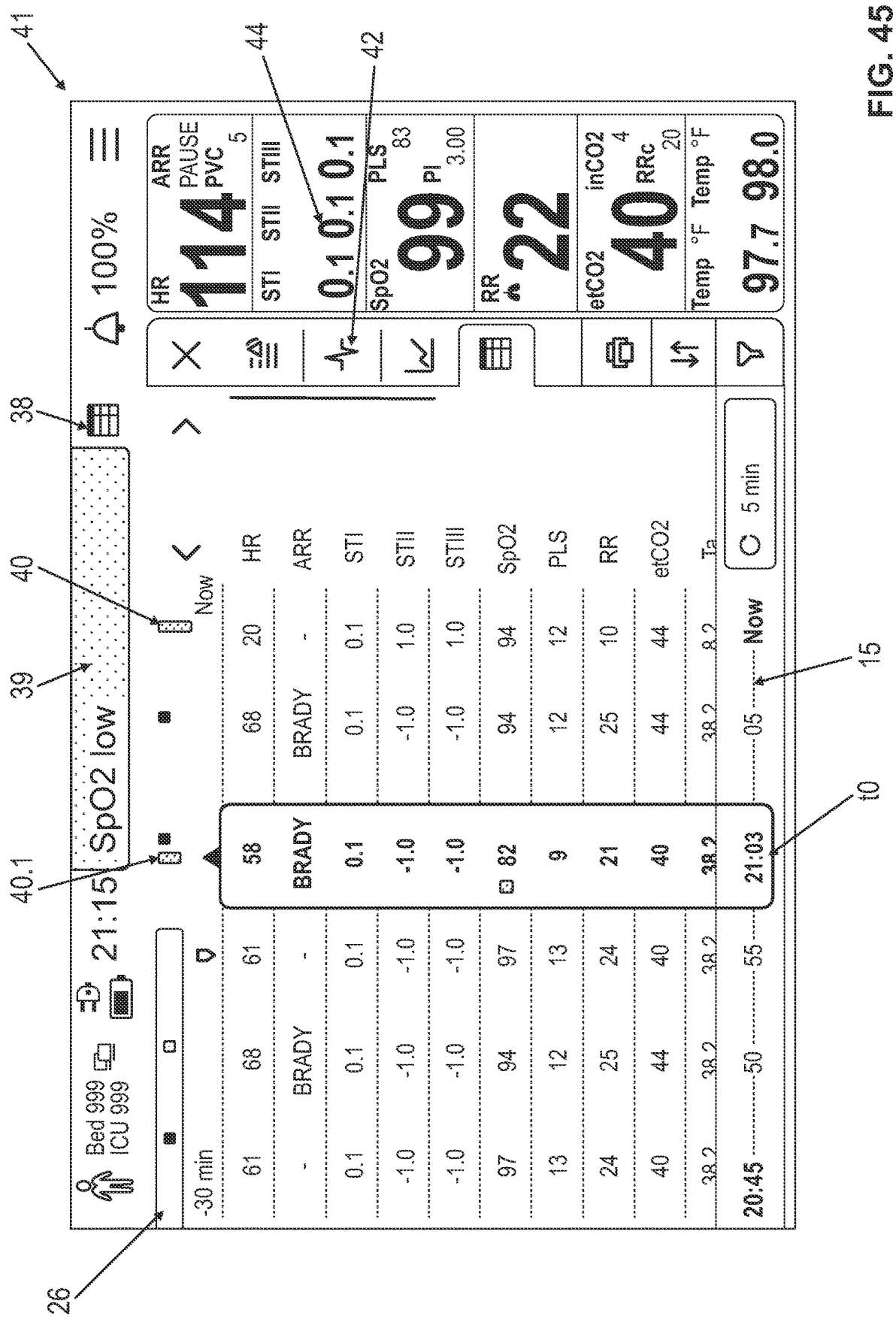
FIG. 45 is a display view showing the embodiment according to FIG. 40: Signal curves are displayed numerically.

In the view that is shown in FIG. 45, the signal curves are displayed by numerical values. The display is again related to the reference time window T1, which comprises the last 30 minutes prior to the current time ("Now"). The reference time t0 is again equal to 09:03:45 pm. Additional signal values are displayed numerically in time increments of 5 minutes. This interval can be changed by the user touching the switch surface with the lettering "5 min."

Figure 46:
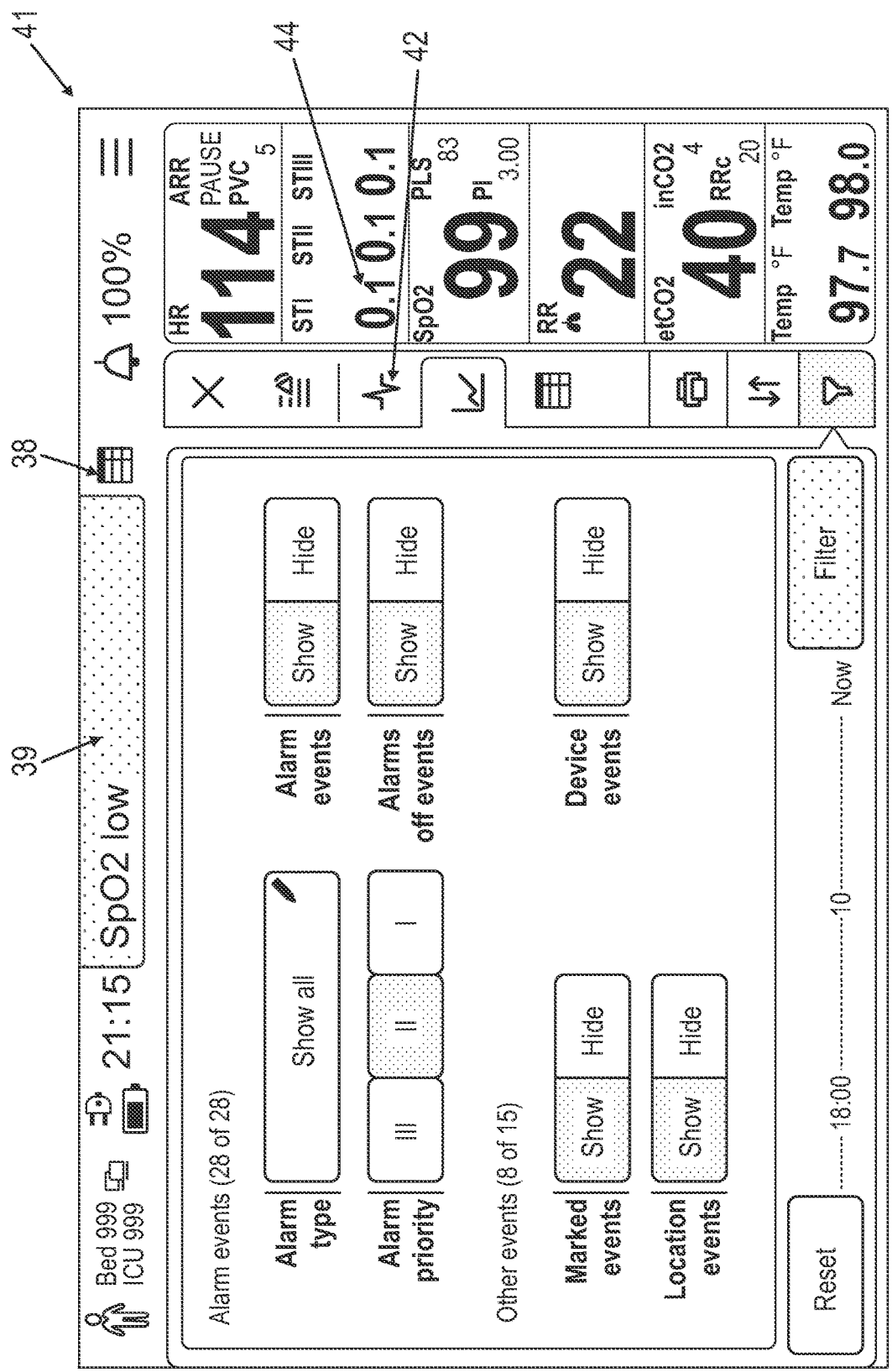
FIG. 46 is a display view showing an embodiment according to FIG. 40: A filter can be set for alarms.

FIG. 46 illustrates how the user can filter which alarms will be displayed. For example, the user can set and then remove the following filters:

Only alarms of a defined alarm type are displayed, for example, only the alarms of the alarm type "SpO2 low."
Only alarms of a certain priority are displayed, for example, only alarms to the alarm type of which the priority "medium" or higher or even only "medium" is assigned.
Alarms are optionally displayed or not displayed.
The monitoring of alarms is switched on or switched off.
Only patient-related alarms or additionally device-side alarms are optionally displayed.
Event markings that are added by the user manually are optionally generated or are not generated. One example of such event marking is the "Marked event" at 08:58: 45 pm in FIG. 42.
Special actions on the patient P are displayed or are not displayed. One example is the patient transport ("Transport docked"), which is ended at 09:00:00 pm, cf. FIG. 42.

The set filter acts both on which alarms are displayed in the alarm reference section 26 and on which alarms are described in the alarm description sequence 11. In addition, it is displayed how many alarms have currently occurred (28 alarms) and which alarm is currently being displayed in field 39 (the chronologically most recent alarm 40 of the alarm type "SpO2 low").

The embodiment described hitherto pertains to a medical device 1, which comprises a signal processing unit 5 of its own and an output unit 7 of its own. The signal processing unit 5 causes the information on the alarms as described above to be displayed on this output unit 7. A data network of a plurality of medical devices will be described below as an example.

Figure 47:
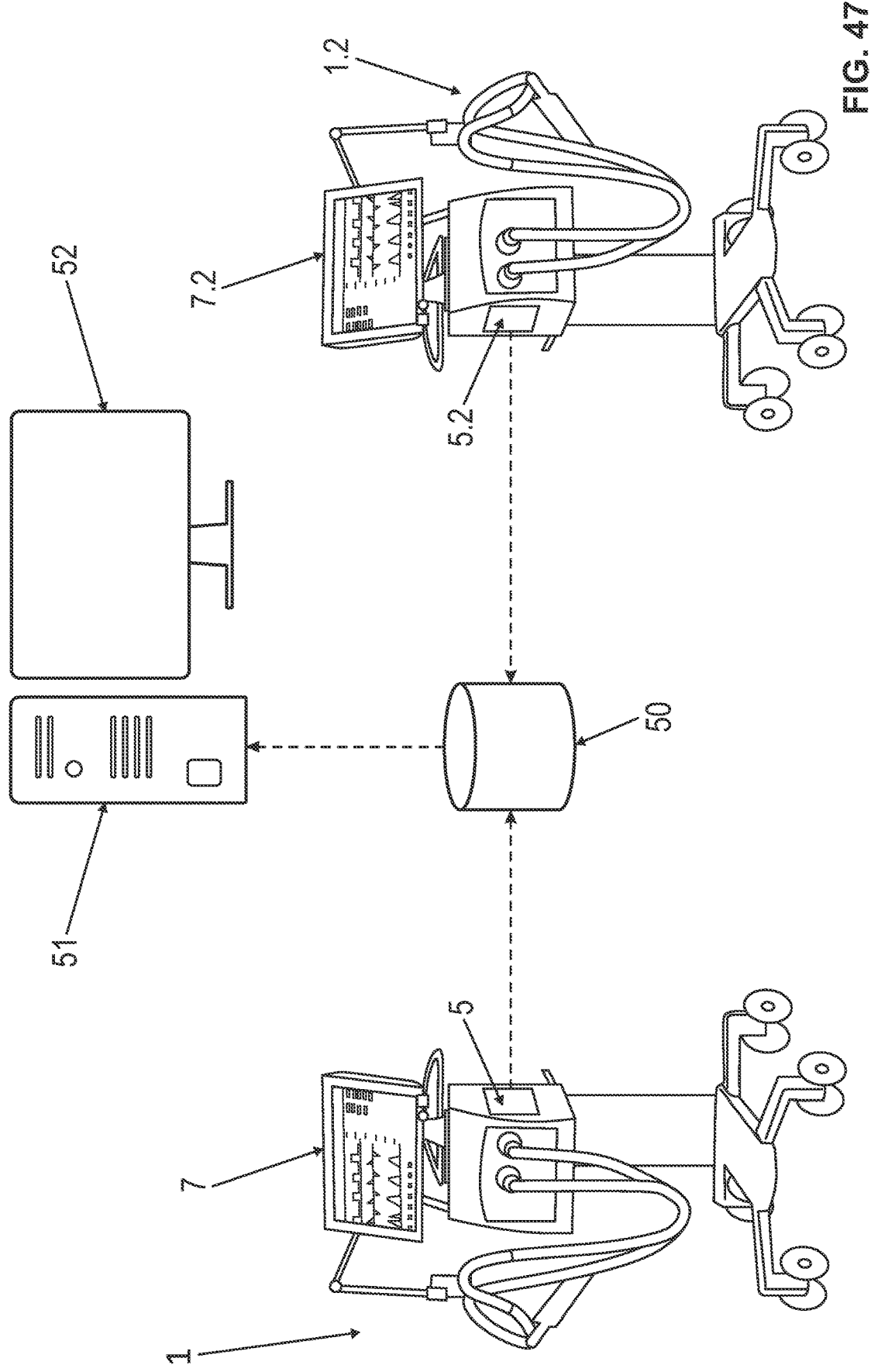
FIG. 47 is a schematic view showing an exemplary system with two medical devices and with a central signal processing unit.

FIG. 47 shows as an example a system which comprises the system according to the present invention. This system comprises the ventilator 1 with the output unit 7 and with the signal processing unit 5 according to FIG. 1,
an additional ventilator 1.2 with an additional output unit 7.2 and with an additional signal processing unit 5.2, wherein said additional ventilator 1.2 may have the same configuration as the ventilator 1 according to FIG. 1,
patient sensors that are capable of transmitting measured values to the ventilator 1 or to the ventilator 1.2
a central memory 50, to which the two signal processing units 5 and 5.2 have write access at least from time t0 time,
a central signal processing unit 51, which has read access to the central memory 50 at least from time t0 time, and
a central output unit 52.

This system may also comprise additional ventilators and/or other medical devices.

The two ventilators 1 and 1.2 as well as the central signal processing unit 51 are consequently connected to one another by a data network. The central signal processing unit 51 actuates the central output unit 52.

Both local signal processing units 5 and 5.2 receive measured values as described above from the patient sensors of the respective ventilators 1 and 1.2, they generate signals, check whether predefined alarm criteria are met, detect alarms and actuate the local output unit 7 and 7.2. These alarms refer to the ventilator 1 and 1.2. The local signal processing units 5 and 5.2 write pieces of information on the detected alarms into the central memory 50. The central signal processing unit 51 reads this central memory 50, for example, at a predefined scanning frequency. The central signal processing unit 51 analyzes the information, which it has read from the central memory 50 and causes alarms of both ventilators 1 and 1.2 to be displayed on the output unit 52 as was described above.

In one embodiment, a user can optionally have alarms of the ventilator 1 or of the ventilator 1.2 displayed. In another embodiment, alarms of both ventilators 1 and 1.2 are displayed simultaneously on the central output unit 52.

While specific embodiments of the invention have been shown and described in detail to illustrate the application of the principles of the invention, it will be understood that the invention may be embodied otherwise without departing from such principles.

LIST OF REFERENCE CHARACTERS

1 Ventilator; it comprises the connection piece 3, the signal processing unit 5 and the output unit 7
1.2 Additional ventilator; it comprises the additional signal processing unit 5.1 and the additional output unit 7.2
2.1.1, . . . , 2.2.2 Measuring electrodes, which are positioned on the skin of the patient P, act as patient sensors
3 Connection piece in front of the mouth of the patient P
4 Optical sensor; it measures the filling level of the lungs of the patient P
5 Signal processing unit of the ventilator 1; it actuates the output unit 7
5.2 Signal processing unit of the additional ventilator 1.2; it actuates the output unit 7.2
6 Pneumatic sensor in the esophagus Sp of the patient P
7 Output unit of ventilator 1; it comprises a display screen; it is actuated by the signal processing unit 5
7.1 Output unit with a smaller display screen
7.2 Output unit of the additional ventilator 1.2; it comprises a display screen; it is actuated by the signal processing unit 5.2
10 Central signal curve area of the display screen 7, in which the time curves of the three signals VT, MV and RR and additional signals are displayed; it refers to the reference time window T1
11 Alarm description sequence of the display screen 7, in which a sequence of alarm descriptions is displayed in the vertical direction, the most recent alarm being located in the topmost location
12 Selected alarm of the alarm type "MV low" at the time 01:33 pm
12.1 Alarm of the alarm type "MV low" at the time 12:03 pm
12.2 Alarm of the alarm type "MV low" at the time 01:59 pm
13 Signal value area of the display screen 7, in which the reference time t0 as well as the values of the signals shown at the reference time t0 are displayed 14 Alarm overview display in the lower area of the display screen 7; it shows the reference time axis 15 and the overall alarm sequence 16 with the alarm reference section 26
15 Displayed time axis for the reference time window T1 in the alarm overview display 14
16 Overall alarm sequence in the alarm overview display 14, in which it displayed at which times alarms of which alarm types were detected; it comprises the alarm reference section 26 for the reference time window T1 of the reference time axis 15
17.1 Symbol for the relevance "high;" it is assigned, e.g., to the alarm type "MV low"
17.2 Symbol for the relevance 37 medium; it is assigned, e.g., to the alarm type "VT"
17.3 Symbol for the relevance "high" of the selected alarm 12
18 Alarm reference sequence on the display screen 7; it shows a sequence of symbols of the alarm types, which have occurred in the reference time window T1
19 Area on the display screen 7, which a user touches and thereby selects an alarm or carries out another user interaction
20 Reference time line, which illustrates the reference time t0 with respect to the reference time axis 15; it acts as a cursor
21.1, 22.2 Lower limit and upper limit of the desired range for the signal MV, which are variable over time
22, 22.1, . . . Sections of the signal MV, which are located below the lower limit 21.1 and have triggered the alarms 12, 12.2, . . .
23 Operating element for fading in or fading out alarm descriptions
24 Display, shows how many additional alarms belong to the same alarm type as the currently selected alarm and are not currently displayed in the alarm description sequence 11
26 Alarm reference section of the overall alarm sequence 16, which refers to the reference time window T1 of the reference time axis 15; it shows the alarms of the overall alarm sequence 16 that have occurred in the reference time window; it provides the positioning display for the reference time window T1
27 Text field, which explains a cause of an alarm
28 Text field, which explains possible remedies to eliminate the cause of an alarm, which cause is described in the text field 27
29 Selection menu for selecting an additional patient-related or equipment-related signal, whose curve shall be displayed
30 Time period window; it shows the duration of the reference time window T1
31 Alarm description for the alarm 12
32 Leading element of the correlation indicator; it points towards the topmost alarm description in the alarm description sequence 11
33 Led element of the correlation indicator; it points towards the corresponding alarm in the alarm reference sequence 18
34 Alarm, of the alarm type "RR high" at the time 01:55 pm
35 Alarm of the alarm type "Apnea" at the time 01:17 pm
37 Computer mouse
38 Operating element, which makes a direct entry possible
41 Column on the display screen 7 with a plurality of operating elements
42 Operating element in column 41 to have the waveform snippet view displayed
43 Time axis for the waveform snippet view
44 Area in which the current signal values of the displayed signal curves are displayed
50 Central memory, into which the local signal processing units 5 and 5.2 of the medical devices 1, 1.2 write pieces of information on the detected alarms and to which the central signal processing unit 51 has read access at least from time t0 time
51 Central signal processing unit; it has read access to the memory 50; actuates the central output unit 52
52 Central output unit; it is actuated by the central signal processing unit 51
HR Signal, which characterizes the heart rate—number of R peaks per minute; displayed in the central signal curve area
LR List direction, in which the alarm description sequence 11 extends; it is at right angles to the time axis display direction ZR
MV Signal ("minute volume")—quantity of breathing air fed into the lungs in [L/minute];
displayed in the central signal curve area 10
RR Respiratory rate of the patient P; displayed in the central signal curve area 10
MV low Alarm type: Value of the signal MV below a lower limit 21.1
P Patient, who is being mechanically ventilated
Sp Esophagus of the patient P
SpO2 Oxygen level in the blood; displayed after a corresponding user input in the central signal curve area 10
SR Writing direction of the alarm description 31; it is at right angles to the list direction LR
T Overall time period to which the overall alarm sequence 16 refers; it comprises the reference time window T1
t0 Variable reference time, which is illustrated by the reference time line 20; it is the current time ("now") or the time of a selected alarm or it is predefined directly by the user
T1 Reference time window, to which the displayed alarms of the alarm reference section 26 as well as of the alarm reference sequence 18 refer; it is a section of the overall time period T
VT "Ventilation" signal—quantity of breathing air in [mL], which flows into the lungs during a single-time breathing; displayed in the central signal curve area 10
Zr Time axis display direction, in which the reference time axis 15 and the overall alarm sequence 16 and the alarm reference section 26 extend; it is at right angles to the list direction LR
Zw Diaphragm of the patient P

What is claimed is:

1. A system comprising:
a medical device;
at least one patient sensor configured to measure a variable occurring at or in a patient in operative connection with the medical device;
an output unit for visually outputting information to a user;
a signal processing unit configured:
to receive measured values from the at least one sensor;
to generate at least one signal by analyzing the received measured values;
to decide whether at least one predefined alarm criterion is met with reference to the at least one signal;
to detect an alarm as well as a time at which the detected alarm occurred, in response to a decision that the at least one predefined alarm criterion is met, wherein the alarm criterion being met indicates the occurrence of the alarm;

to actuate the output unit including to actuate the output
   unit such that the actuated output unit displays
   simultaneously the following:
      an overall alarm sequence comprising a display of an
         alarm sequence over time of alarms that were
         detected during a predefined overall time period,
         wherein the display of the alarm sequence over
         time extends in a time axis display direction;
      an alarm reference section comprising a display of
         alarms, shown in the overall alarm sequence that
         were detected, in a predefined reference time
         window, wherein the reference time window is a
         portion of the overall time period, the display of
         the alarm reference section extends in the time
         axis display direction, and the alarm reference
         section provides a positioning display comprising
         a representation of a temporal position of the
         reference time window relative to the overall time
         period; and
      a signal curve display or an alarm reference sequence
         or both a signal curve display and an alarm
         reference sequence, wherein the signal curve display is a display of a respective time curve of the
         at least one generated signal over a course of the
         reference time window, the alarm reference
         sequence is a display of a sequence of alarms that
         have occurred in the reference time window, the
         signal curve display and the alarm reference
         sequence extend in the time axis display direction,
         and a time scale of the signal curve display and a
         time scale of the alarm reference sequence are
         finer than a time scale of the overall alarm
         sequence and a time scale for the alarm reference
         section.

2. A system in accordance with claim 1, wherein:
   at least two different alarm types are predefined;
   each of the alarm types is defined by a respective predefined alarm criterion;
   the signal processing unit is further configured to detect a selection of an alarm by a user; and
   the signal processing unit is further configured to actuate the output unit after selection of an alarm such that the actuated output unit displays, in the overall alarm sequence and/or in the alarm reference section and/or in the alarm reference sequence, each additional alarm, which belongs to the same alarm type as the selected alarm, with highlighting compared to other displayed alarms.

3. A system in accordance with claim 1, wherein the signal processing unit is configured to actuate the output unit such that the actuated output unit:
   displays the overall alarm sequence and the alarm reference section with the same time scale; and
   displays the alarm reference section as being positioned correctly in time relative to the overall alarm sequence.

4. A system in accordance with claim 1, wherein the signal processing unit is configured to actuate the output unit such that the actuated output unit displays a reference time located in the reference time window in the signal curve display and/or in the alarm reference section and/or in the alarm reference sequence, wherein the signal processing unit is further configured:
   to detect a user input for changing the displayed reference time;
   to change the reference time window or the reference time when the changed reference time is not located in the reference time window such that the changed reference time is located in the reference time window; and
   to display the changed reference time, in the signal curve display and/or in the alarm reference section and/or in the alarm reference sequence, after the detection of the user input for changing the reference time.

5. A system in accordance with claim 4, wherein the signal processing unit is further configured:
   to detect a selection by a user of an alarm, which selection is displayed in the signal curve display and/or in the alarm reference section and/or in the alarm reference sequence;
   to use, after selection of an alarm, the time at which the selected alarm has occurred as a user input for changing the reference time; and
   to use the time at which the selected alarm has occurred as the changed reference time.

6. A system in accordance with claim 1, wherein the signal processing unit is further configured:
   to detect a selection by a user of an alarm, which is displayed in the signal curve display, in the alarm reference section and/or in the alarm reference sequence; and
   to display each additional alarm, which is displayed in the signal curve display and/or in the alarm reference section and/or in the alarm reference sequence and is of a same type as that of the selected alarm, with highlighting after the selection of an alarm.

7. A system in accordance with claim 1, wherein the signal processing unit is further configured:
   to detect a user input for changing the reference time window; and
   to actuate the output unit after the detection of the user input for changing the reference time window, such that the actuated output unit adjusts the alarm reference section and the signal curve display and/or the alarm reference sequence to the change in the reference time window and also leaves the overall alarm sequence unchanged.

8. A system in accordance with claim 1, wherein:
   the signal processing unit is configured to actuate the output unit such that the actuated output unit displays an alarm description sequence;
   the alarm description sequence comprises a textual alarm description for a sequence of alarms that belong to a chronological sequence displayed in the overall alarm sequence;
   a list direction in which the alarm description sequence extends is at right angles to the time axis display direction; and
   the respective writing direction of each alarm description at right angles to the list direction.

9. A system in accordance with claim 8, wherein the signal processing unit is configured to actuate the output unit such that the actuated output unit displays:
   the alarm reference sequence; and
   a correlation indicator with a leading element and with a led element, wherein
      the leading element points towards an alarm description in the alarm description sequence and the led element points towards the alarm to which this alarm description refers in the alarm reference sequence; or
      the leading element points towards an alarm in the alarm reference sequence and the led element points towards the alarm description in the alarm description sequence that refers to the alarm.

10. A system in accordance with claim 1, wherein:
the signal processing unit comprises a first signal processing device and a second signal processing device, which are separated from one another in space; and
the first signal processing device is assigned to the medical device and is configured:
to receive the measured values;
to generate the signal or at least one signal;
to decide whether the alarm criterion or an alarm criterion is met;
to detect an alarm as well as the time at which this alarm occurred; and
to transmit a message to the second signal processing device, which message comprises information on the alarm and on a time; and
the second signal processing device is configured to actuate the output unit such that the actuated output unit displays the overall alarm sequence, the alarm reference section, the display of the position of over time and the signal curve display and/or the alarm reference sequence.

11. A process for generating alarms and for displaying the alarms, the process comprising the steps of:
providing an output unit for a visual output of information to a user, wherein the output unit is a part of a system comprising a medical device, at least one patient sensor and a signal processing unit and the at least one patient sensor is configured to measure at least one variable occurring at or in a patient connected to the medical device;
with the signal processing unit, automatically receiving measured values from the patient sensor;
with the signal processing unit, automatically generating a signal by analyzing received measured values;
with the signal processing unit, automatically deciding whether at least one predefined alarm criterion is met, wherein the predefined alarm criterion or each predefined alarm criterion is in reference to the signal generated by the signal processing unit;
with the signal processing unit, automatically detecting, in response to a decision that the alarm criterion or an alarm criterion is met, an alarm as well as a time at which the detected alarm has occurred, wherein a meeting of the alarm criterion indicates the occurrence of the alarm; and
with the signal processing unit, actuating the output unit such that the output unit, at some point in time displays simultaneously the following:
an overall alarm sequence, which is a display of an overall alarm sequence comprising a display of a sequence over time of alarms that were detected during a predefined overall time period, wherein the display of the overall alarm sequence extends in a time axis display direction;
an alarm reference section comprising a display of the alarms displayed in the overall alarm sequence that were detected during a predefined reference time window, wherein the reference time window is a detail of the overall time period, the display of the alarm reference section extends in the time axis display direction and the alarm reference section comprises a representation of a temporal position of the reference time window relative to the overall time period; and
a signal curve display or an alarm reference sequence or both a signal curve display and an alarm reference sequence, wherein the signal curve display is a display of the respective time curve of the generated signal or of the at least one generated signal over a course of the reference time window and the alarm reference sequence comprises a display of a sequence of alarms, which occurred in the reference time window and the signal curve display and the alarm reference sequence extend in the time axis display direction and a time scale for the signal curve display and a time scale for the alarm reference sequence are finer than a time scale for the overall alarm sequence and a time scale for the alarm reference section.

12. A process according to claim 11, wherein the process steps executed by the signal processing unit are executed with a computer.

13. A process according to claim 11, wherein the process steps provide a signal sequence, comprising commands, which can be executed on the signal processing unit and the signal sequence prompts the signal processing unit to carry out the process.

* * * * *